(12) United States Patent
Schmidt et al.

(10) Patent No.: US 6,207,671 B1
(45) Date of Patent: *Mar. 27, 2001

(54) CYCLOALKANO-PYRIDINES

(75) Inventors: Gunter Schmidt; Arndt Brandes; Rolf Angerbauer; Michael Lögers, all of Wuppertal; Matthias Müller-Gliemann, Solingen; Carsten Schmeck, Wuppertal; Klaus-Dieter Bremm, Recklinghausen; Hilmar Bischoff, Wuppertal; Delf Schmidt, Wuppertal; Joachim Schuhmacher, Wuppertal; Henry Giera, Grosskitzighofen; Holger Paulsen, Wuppertal; Paul Naab, Wuppertal; Michael Conrad, Wuppertal; Jürgen Stoltefuss, Haan, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,648

(22) Filed: Mar. 8, 2000

Related U.S. Application Data

(63) Continuation-in-part of application No. 08/889,530, filed on Jul. 8, 1997, now Pat. No. 6,069,148.

(30) Foreign Application Priority Data

Jul. 8, 1996 (DE) .............................. 196 27 419
Feb. 24, 1997 (DE) .............................. 197 07 199

(51) Int. Cl.[7] .................. A61K 31/438; A61K 31/47; C07D 215/00; C07D 217/00
(52) U.S. Cl. .................. 514/277; 514/261; 514/305; 514/311; 514/256; 514/334; 514/335; 514/336; 514/337; 514/338; 514/339; 514/340; 514/341; 514/342; 544/245; 544/333; 546/139; 546/148; 546/152; 546/176; 546/255; 546/270.1; 546/271.7; 546/273.4; 546/279.7; 546/281.7
(58) Field of Search .................. 514/261, 277, 514/305, 311, 256, 334, 335, 336, 337, 338, 339, 340, 341, 342; 544/245, 333; 546/139, 148, 152, 176, 255, 270.1, 271.7, 273.4, 279.7, 281.7

(56) References Cited

U.S. PATENT DOCUMENTS 4,814,346 * 3/1989 Albert .
5,006,530 * 4/1991 Angerbauer .
5,169,857 * 12/1992 Angerbauer .

* cited by examiner

Primary Examiner—D. Margaret Seaman
(74) Attorney, Agent, or Firm—Norris McLaughlin & Marcus

(57) ABSTRACT

The cycloalkano-pyridines are prepared by reacting corresponding cycloalkano-pyridine-aldehydes with suitable organometallic compounds or Wittig or Grignard reagents or reacting compounds of the cycloalkano-pyridine alcohols type with suitable bromine compounds, and optionally varying the functional groups accordingly. The cycloalkanopyridines are suitable as active compounds in medicaments, in particular in medicaments for the treatment of hypertipoproteinaemia and arteriosclerosis.

8 Claims, No Drawings

CYCLOALKANO-PYRIDINES

This application is a CIP of 08/889,530, filed Jul. 8, 1997, now U.S. Pat. No. 6,069,148.

The present invention relates to cycloalkano-pyridines, processes for their preparation and their use in medicaments.

U.S. Pat. No. 5,169,857 A2 discloses 7-(polysubstituted pyridyl)-6-heptenoates for the treatment of arteriosclerosis, lipoproteinaemia and hyperlipoproteinaemia. The preparation of 7-(4-aryl-3-pyridyl)-3,5-dihydroxy-6-heptenoates is additionally described in the publication EP 325 130 A2. The compound 5(6H)-quinolone, 3-benzyl-7,8-dihydro-2,7,7-trimethyl-4-phenyl- is furthermore known from the publication Khim. Geterotsikl. Soedin. (1967), (6), 1118–1120.

The present invention relates to cycloalkano-pyridines of the general formula (I)

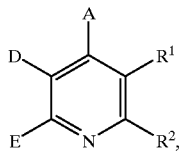

in which

A represents aryl having 6 to 10 carbon atoms, which is optionally substituted up to 5 times in an identical or different manner by halogen, nitro, hydroxyl, trifluoromethyl, trifluoromethoxy or by straight-chain or branched alkyl, acyl, hydroxyalkyl or alkoxy each having up to 7 carbon atoms, or by a group of the formula $-NR^3R^4$, in which $R^3$ and $R^4$ are identical or different and denote hydrogen, phenyl or straight-chain or branched alkyl having up to 6 carbon atoms, D represents aryl having 6 to 10 carbon atoms, which is optionally substituted by phenyl, nitro, halogen, trifluoromethyl or trifluoromethoxy, or represents a radical of the formula

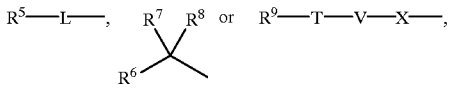

in which $R^5$ and $R^6$ and $R^9$ independently of one another denote cycloalkyl having 3 to 6 carbon atoms, or denote aryl having 6 to 10 carbon atoms, or a 5- to 7-membered, optionally benzo-fused, saturated or unsaturated, mono-, bi- or tricyclic heterocycle having up to 4 heteroatoms from the series S, N and/or O, where the cycles are substituted, if appropriate, in the case of the nitrogen-containing rings also via the N function, up to 5 times in an identical or different manner by halogen, trifluoromethyl, nitro, hydroxyl, cyano, carboxyl, trifluoromethoxy, straight-chain or branched acyl, alkyl, alkylthio, alkylalkoxy, alkoxy or alkoxycarbonyl each having up to 6 carbon atoms, by aryl- or trifluoromethyl-substituted aryl each having 6 to 10 carbon atoms or by an optionally benzo-fused, aromatic 5- to 7-membered heterocycle having up to 3 heteroatoms from the series S, N and/or O, and/or are substituted by a group of the formula $-OR^{10}$, $-SR^{11}$, $-SO_2R^{12}$ or $-NR^{13}R^{14}$, in which $R^{10}$, $R^{11}$ and $R^{12}$ independently of one another denote aryl having 6 to 10 carbon atoms, which for its part is substituted up to 2 times in an identical or different manner by phenyl, halogen or by straight-chain or branched alkyl having up to 6 carbon atoms, $R^{13}$ and $R^{14}$ are identical or different and have the meaning of $R^3$ and $R^4$ indicated above, or $R^5$ and/or $R^6$ denote a radical of the formula

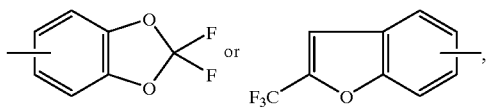

$R^7$ denotes hydrogen or halogen and $R^8$ denotes hydrogen, halogen, azido, trifluoromethyl, hydroxyl, trifluoromethoxy, straight-chain or branched alkoxy or alkyl each having up to 6 carbon atoms or a radical of the formula $-NR^{15}R^{16}$, in which $R^{15}$ and $R^{16}$ are identical or different and have the meaning of $R^3$ and $R^4$ indicated above, or $R^7$ and $R^8$ together form a radical of the formula $=O$ or $=NR^{17}$, in which $R^{17}$ denotes hydrogen or straight-chain or branched alkyl, alkoxy or acyl each having up to 6 carbon atoms, L denotes a straight-chain or branched alkylene or alkenylene chain each having up to 8 carbon atoms, each of which is optionally substituted up to 2 times by hydroxyl, T and X are identical or different and denote a straight-chain or branched alkylene chain having up to 8 carbon atoms, or T or X denotes a bond, V represents an oxygen or sulphur atom or an $-NR^{18}$ group, in which $R^{18}$ denotes hydrogen or straight-chain or branched alkyl having up to 6 carbon atoms or phenyl, E represents cycloalkyl having 3 to 8 carbon atoms, or represents straight-chain or branched alkyl having up to 8 carbon atoms, which is optionally substituted by cycloalkyl having 3 to 8 carbon atoms or hydroxyl, or represents phenyl which is optionally substituted by halogen or trifluoromethyl, $R^1$ and $R^2$ together form a straight-chain or branched alkylene chain having up to 7 carbon atoms, which must be substituted by a carbonyl group and/or by a radical of the formula

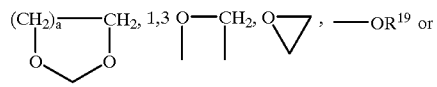

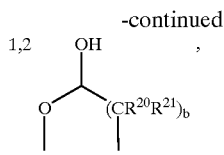

in which a and b are identical or different and denote a number 1, 2 or 3, $R^{19}$ denotes hydrogen, cycloalkyl having 3 to 7 carbon atoms, straight-chain or branched silylalkyl having up to 8 carbon atoms or straight-chain or branched alkyl having up to 8 carbon atoms, which is optionally substituted by hydroxyl, straight-chain or branched alkoxy having up to 6 carbon atoms or by phenyl, which for its part can be substituted by halogen, nitro, trifluoromethyl, trifluoromethoxy or by phenyl- or tetrazole-substituted phenyl, and alkyl is optionally substituted by a group of the formula —$OR^{22}$, in which $R^{22}$ denotes straight-chain or branched acyl having up to 4 carbon atoms or benzyl, or $R^{19}$ denotes straight-chain or branched acyl having up to 20 carbon atoms or benzoyl which is optionally substituted by halogen, trifluoromethyl, nitro or trifluoromethoxy, or denotes straight-chain or branched fluoroacyl having up to 8 carbon atoms and 9 fluorine atoms, $R^{20}$ and $R^{21}$ are identical or different, and denote hydrogen, phenyl or straight-chain or branched alkyl having up to 6 carbon atoms, or $R^{20}$ and $R^{21}$ together form a 3 to 6-membered carbocycle, and, if appropriate also geminally, the carbocycles formed are optionally substituted up to 6 times in an identical or different manner by trifluoromethyl, hydroxyl, halogen, carboxyl, nitro, azido, cyano, cycloalkyl or cycloalkyloxy each having 3 to 7 carbon atoms, by straight-chain or branched alkoxycarbonyl, alkoxy or alkylthio each having up to 6 carbon atoms or by straight-chain or branched alkyl having up to 6 carbon atoms, which for its part is substituted up to 2 times in an identical or different manner by hydroxyl, benzyloxy, trifluoromethyl, benzoyl, straight-chain or branched alkoxy, oxyacyl or carboxyl each having up to 4 carbon atoms and/or phenyl, which for its part can be substituted by halogen, trifluoromethyl or trifluoromethoxy, and/or the carbocycles formed, also geminally, are optionally substituted up to 5 times in an identical or different manner by phenyl, benzoyl, thiophenyl or sulphonylbenzyl, which for their part are optionally substituted by halogen, trifluoromethyl, trifluoromethoxy or nitro, and/or are optionally substituted by a radical of the formula

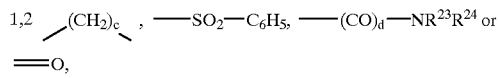

in which c denotes a number 1, 2, 3 or 4, d denotes a number 0 or 1, $R^{23}$ and $R^{24}$ are identical or different and denote hydrogen, cycloalkyl having 3 to 6 carbon atoms, straight-chain or branched alkyl having up to 6 carbon atoms, benzyl or phenyl, which is optionally substituted up to 2 times in an identical or different manner by halogen, trifluoromethyl, cyano, phenyl or nitro, and/or the carbocycles formed are optionally substituted by a spiro-linked radical of the formula

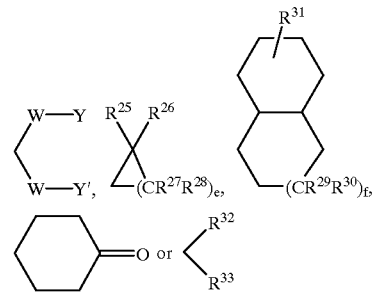

in which

W either denotes an oxygen or a sulphur atom,

Y and Y' together form a 2- to 6-membered straight-chain or branched alkylene chain, e denotes a number 1, 2, 3, 4, 5, 6 or 7, f denotes a number 1 or 2, $R^{25}$, $R^{26}$, $R^{27}$, $R^{28}$, $R^{29}$, $R^{30}$ and $R^{31}$ are identical or different and denote hydrogen, trifluoromethyl, phenyl, halogen or straight-chain or branched alkyl or alkoxy each having up to 6 carbon atoms, or $R^{25}$ and $R^{26}$ or $R^{27}$ and $R^{28}$ in each case together form a straight-chain or branched alkyl chain having up to 6 carbon atoms, or $R^{25}$ and $R^{26}$ or $R^{27}$ and $R^{28}$ in each case together form a radical of the

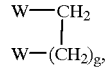

in which

W has the meaning indicated above, g denotes a number 1, 2, 3, 4, 5, 6 or 7, $R^{32}$ and $R^{33}$ together form a 3- to 7-membered heterocycle which contains an oxygen or sulphur atom or a group of the formula SO, $SO_2$ or —$NR^{34}$, in which $R^{34}$ denotes hydrogen, phenyl, benzyl or straight-chain or branched alkyl having up to 4 carbon atoms, and their salts and N-oxides, with the exception of 5(6H)-quinolone, 3-benzoyl-7,8-dihydro-2,7,7-trimethyl-4-phenyl-.

The alkanopyridines according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, if appropriate benzo-fused, in the context of the invention in general represents a saturated or unsaturated 5- to 7-membered, preferably 5- to 6-membered, heterocycle, which can contain up to 3 heteroatoms from the series consisting of S, N and/or O. Examples which may be mentioned are: indolyl, isoquinolyl, quinolyl, benzo[b]thiophenyl, benzo[b]furanyl, pyridyl, thienyl, furyl, pyrrolyl, thiazolyl, oxazolyl, imidazolyl, morpholinyl or piperidyl. Quinolyl, thienyl, pyridyl and furyl are preferred.

Preferred compounds of the general formula (I) according to the invention are those
in which
A represents naphthyl or phenyl, each of which is optionally substituted up to 2 times in an identical or different manner by fluorine, chlorine, bromine, amino, hydroxyl, trifluoromethyl, trifluoromethoxy or by straight-chain or branched alkyl or alkoxy each having up to 6 carbon atoms.
D represents phenyl which is optionally substituted by nitro, fluorine, chlorine, bromine, phenyl, trifluoromethyl or trifluoromethoxy, or represents a radical of the formula

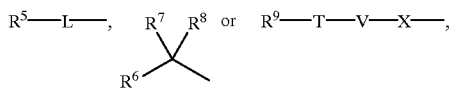

in which
$R^5$, $R^6$ and $R^9$ independently of one another denote cyclopropyl, cyclopentyl or cyclohexyl, or denote phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl, where the cycles are also substituted via the N function, optionally up to 3 times in the case of the nitrogen-containing rings, in an identical or different manner by fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl each having up to 4 carbon atoms, triazolyl, tetrazolyl, benzoxathiazolyl, or trifluoromethyl-substituted phenyl or phenyl,
and/or are substitued by a group of the formula —$OR^{10}$, —$SR^{11}$ or —$SO_2R^{12}$,
in which
$R^{10}$, $R^{11}$ and $R^{12}$ are identical or different and denote phenyl, which for its part is substitued up to 2 times in an identical or different manner by phenyl, fluorine, chlorine or by straight-chain or branched alkyl having up to 4 carbon atoms,
or
$R^5$ and/or $R^6$ denotes a radical of the formula

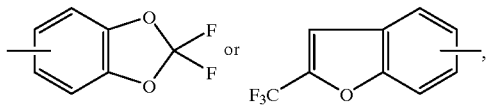

$R^7$ denotes hydrogen, fluorine, chlorine or bromine
and
$R^8$ denotes hydrogen, fluorine, chlorine, bromine, azido, trifluoromethyl, hydroxyl, trifluoromethoxy, straight-chain or branched alkoxy or alkyl having up to 5 carbon atoms in each case or a radical of the formula —$NR^{15}R^{16}$,
in which
$R^{15}$ and $R^{16}$ are identical or different and denote hydrogen, phenyl or straight-chain or branched alkyl having up to 4 carbon atoms,
or
$R^7$ and $R^8$ together form a radical of the formula =O or =$NR^{17}$,
in which
$R^{17}$ denotes hydrogen or straight-chain or branched alkyl, alkoxy or acyl each having up to 4 carbon atoms,
L denotes a straight-chain or branched alkylene or alkenylene chain each having up to 6 carbon atoms, each of which is optionally substituted up to 2 times by hydroxyl,
T and X are identical or different and denote a straight-chain or branched alkylene chain having up to 6 carbon atoms,
or
T or X denotes a bond,
V represents an oxygen or sulphur atom or a group of the formula —$NR^{18}$—,
in which
$R^{18}$ denotes hydrogen or straight-chain or branched alkyl having up to 4 carbon atoms or phenyl,
E represents cyclopropyl, -butyl, -pentyl, -hexyl or -heptyl, or represents straight-chain or branched alkyl having up to 6 carbon atoms, which is optionally substituted by cyclopropyl, -butyl, -hexyl, -pentyl, -heptyl or by hydroxyl,
or represents phenyl which is optionally substituted by fluorine, chlorine or trifluoromethyl,
$R^1$ and $R^2$ together form a straight-chain or branched alkylene chain having up to 6 carbon atoms, which must be substituted by a carboxyl group and/or by a radical of the formula $-(CH_2)_a-CH_2$, 1,3

[structure: 1,3-dioxolane with (CH₂)ₐ]

$-CH_2-O$

[structure with CH₂O]

[cyclopropyl structure], $-OR^{19}$ or 1,2

[structure: OH, O, (CR²⁰R²¹)_b]

in which
a and b are identical or different and denote a number 1, 2 or 3,
$R^{19}$ denotes hydrogen, cyclopropyl, cyclopentyl, cyclohexyl, straight-chain or branched silylalkyl having up to 7 carbon atoms or straight-chain or branched alkyl having up to 6 carbon atoms, which is optionally substituted by hydroxyl, straight-chain or branched alkoxy having up to 4 carbon atoms or by phenyl which for its part can be substituted by fluorine, chlorine, bromine, nitro, trifluoromethyl, trifluoromethoxy or by phenyl- or tetrazole-substituted phenyl,
and alkyl is optionally substituted by a group of the formula $-OR^{22}$,
in which
$R^{22}$ denotes straight-chain or branched acyl having up to 3 carbon atoms or benzyl,
or
$R^{19}$ denotes straight-chain or branched acyl having up to 18 carbon atoms or benzoyl which is optionally substituted by fluorine, chlorine, bromine, trifluoromethyl, nitro or trifluoromethoxy, or denotes straight-chain or branched fluoroacyl having up to 6 carbon atoms,
$R^{20}$ and $R^{21}$ are identical or different, and denote hydrogen, phenyl or straight-chain or branched alkyl having up to 4 carbon atoms,
or
$R^{20}$ and $R^{21}$ together form a cyclopropyl, cyclobutyl, cyclopentyl, cyclohexyl or cycloheptyl ring,
and the carbocycles formed are optionally substituted up to 5 times in an identical or different manner, optionally also geminally, by trifluoromethyl, hydroxyl, carboxyl, azido, fluorine, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio each having up to about 5 carbon atoms or straight-chain or branched alkyl having up to 5 carbon atoms, which for its part is substituted up to 2 times in an identical or different manner by hydroxyl, benzyloxy, benzoyl, straight-chain or branched alkoxy or oxyacyl each having up to 3 carbon atoms, trifluoromethyl and/or phenyl, which for its part can be substituted by fluorine, chlorine, bromine, trifluoromethyl or trifluoromethoxy,
and/or the carbocycles formed, also geminally, are optionally substituted up to 4 times in an identical or different manner by phenyl, benzoyl, thiophenyl or sulphonylbenzyl, which for their part are optionally substituted by fluorine, chlorine, bromine, trifluoromethyl, trifluoromethoxy or nitro,
and/or are optionally substituted by a radical of the formula 1,2 [(CH₂)_c structure], $-SO_2-C_6H_5$, $-(CO)_d-NR^{23}R^{24}$ or
$=O$, in which
c denotes a number 1, 2, 3 or 4,
d denotes a number 0 or 1,
$R^{23}$ and $R^{24}$ are identical or different and denote hydrogen, cyclopropyl, cyclobutyl, cyclopentyl, cyclohexyl, straight-chain or branched alkyl having up to 5 carbon atoms, benzyl or phenyl, which is optionally substituted by fluorine, chlorine, bromine, phenyl or trifluoromethyl,
and/or the carbocycles formed are optionally substituted by a spiro-linked radical of the formula

[spiro structures with W—Y, W—Y', $R^{25}$, $R^{26}$, $(CR^{27}R^{28})_e$, $R^{31}$, $(CR^{29}R^{30})_f$, or cyclohexyl=O]

in which
W denotes either an oxygen or a sulphur atom,
Y and Y' together form a 2- to 5-membered straight-chain or branched alkyl chain,
e denotes a number 1, 2, 3, 4, 5 or 6,
f denotes a number 1 or 2,
$R^{25}$, $R^{26}$, $R^{27}$, $R^{28}$, $R^{29}$, $R^{30}$ and $R^{31}$ are identical or different and denote hydrogen, trifluoromethyl, phenyl, fluorine, chlorine, bromine or straight-chain or branched alkyl or alkoxy each having up to 5 carbon atoms,
or
$R^{25}$ and $R^{26}$ or $R^{27}$ and $R^{28}$ in each case together form a straight-chain or branched alkyl chain having up to 5 carbon atoms or
$R^{25}$ and $R^{26}$ or $R^{27}$ and $R^{28}$ in each case together form a radical of the formula W—CH₂
 |
W—(CH₂)_g, in which
W has the meaning indicated above,
g denotes a number 1, 2, 3, 4, 5 or 6,
and their salts and N-oxides with the exception of 5(6H)-quinolone, 3-benzoyl-7,8-dihydro-2,7,7-trimethyl-4-phenyl-.

Particularly preferred compounds of the general formula (I) according to the invention are those
in which
A represents phenyl which is optionally substituted up to 2 times in an identical or different manner by fluorine, chlorine, bromine, hydroxyl, trifluoromethyl, trifluoromethoxy or by straight-chain or branched alkyl or alkoxy each having up to 5 carbon atoms, D represents phenyl which is optionally substituted by nitro, trifluoromethyl, phenyl, fluorine, chlorine or bromine, or represents a radical of the formula

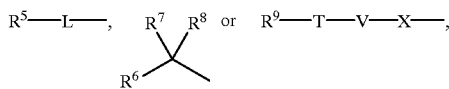

in which
R$^5$, R$^6$ and R$^9$ independently of one another denote cyclopropyl, cyclopentyl or cyclohexyl, or denote phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl, where the cycles are substituted, optionally up to 3 times, in the case of the nitrogen-containing rings also via the N function, in an identical or different manner by fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl each having up to 4 carbon atoms, triazolyl, tetrazolyl, benzothiazolyl, trifluoromethyl-substituted phenyl or phenyl and/or are substituted by a group of the formula —OR$^{10}$, —SR$^{11}$ or —SO$_2$R$^{12}$,
in which
R$^{10}$, R$^{11}$ and R$^{12}$ are identical or different and denote phenyl, which for its part is substituted up to 2 times in an identical or different manner by phenyl, fluorine, chlorine or by straight-chain or branched alkyl having up to 3 carbon atoms,
or
R$^5$ and/or R$^6$ denotes a radical of the formula

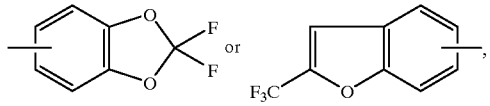

R$^7$ denotes hydrogen or fluorine
and
R$^8$ denotes hydrogen, fluorine, chlorine, bromine, azido, trifluoromethyl, hydroxyl, trifluoromethoxy, or straight-chain or branched alkoxy or alkyl each having up to 4 carbon atoms or a radical of the formula —NR$^{15}$R$^{16}$,
in which
R$^{15}$ and R$^{16}$ are identical or different and denote hydrogen or straight-chain or branched alkyl having up to 3 carbon atoms,
or
R$^7$ and R$^8$ together form a radical of the formula =O or =NR$^{17}$,
in which
R$^{17}$ denotes hydrogen or straight-chain or branched alkyl, alkoxy or acyl each having up to 4 carbon atoms,
L denotes a straight-chain or branched alkylene or alkenylene chain each having up to 5 carbon atoms, each of which is optionally substituted up to 2 times by hydroxyl,
T and X are identical or different and denote a straight-chain or branched alkylene chain having up to 3 carbon atoms,
or
T or X denotes a bond,
V represents an oxygen or sulphur atom or a group of the formula —NR$^{15}$,
in which
R$^{15}$ denotes hydrogen or straight-chain or branched alkyl having up to 3 carbon atoms,
E represents cyclopropyl, cyclopentyl or cyclohexyl or phenyl, which is optionally substituted by fluorine or trifluoromethyl, or represents straight-chain or branched alkyl having up to 4 carbon atoms, which is optionally substituted by hydroxyl,
R$^1$ and R$^2$ together form a straight-chain or branched alkylene chain having up to 5 carbon atoms, which must be substituted by a carbonyl group and/or a radical of the formula

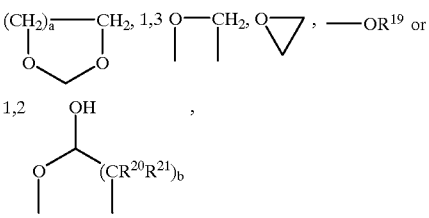

in which
a and b are identical or different and denote a number 1, 2 or 3,
R$^{19}$ denotes hydrogen, cyclopropyl, cyclopentyl, cyclohexyl, straight-chain or branched silylalkyl having up to 6 carbon atoms or straight-chain or branched alkyl having up to 4 carbon atoms, which is optionally substituted by hydroxyl, straight-chain or branched alkoxy having up to 3 carbon atoms or by phenyl, which for its part can be substituted by fluorine, chlorine, bromine, nitro, trifluoromethyl, trifluoromethoxy or by phenyl- or tetrazole-substituted phenyl,
and alkyl is optionally substituted by a group of the formula —OR$^{22}$,
in which
R$^{22}$ denotes straight-chain or branched acyl having up to 3 carbon atoms or benzyl,
or
R$^{19}$ denotes straight-chain or branched acyl having up to 15 carbon atoms or benzoyl, which is optionally substituted by fluorine, chlorine, bromine, trifluoromethyl, nitro or trifluoromethoxy, or denotes straight-chain or branched fluoroacyl having up to 4 carbon atoms,
R$^{20}$ and R$^{21}$ are identical or different, and denote hydrogen, phenyl or straight-chain or branched alkyl having up to 3 carbon atoms
or
R$^{20}$ and R$^{21}$ together form a cyclopropyl, cyclopentyl or cyclohexyl ring,
and the carbocycles formed are optionally substituted up to 4 times in an identical or different manner, optionally also geminally, by fluorine, hydroxyl, trifluoromethyl, nitrile, carboxyl, azido, chlorine, bromine, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio each having up to 4 carbon atoms or straight-chain or branched alkyl having up to 4 carbon atoms, which for its part is substituted up to 2 times in an identical or different manner by hydroxyl, benzyloxy, trifluoromethyl, benzoyl, methoxy, oxyacetyl and/or phenyl, which for its part can be substituted by fluorine, chlorine, bromine, trifluoromethyl or trifluoromethoxy, and/or the carbocycles formed, are optionally substituted, also geminally; up to 4 times in an identical or different manner by phenyl, benzoyl, thiophenyl or sulphonylbenzoyl, which for their part are optionally substituted by fluorine, trifluoromethyl, trifluoromethoxy or nitro, and/or are optionally substituted by a radical of the formula $$1,2 \diagup(CH_2)_c\diagdown, \quad -SO_2-C_6H_5, \quad -(CO)_d-NR^{23}R^{24} \text{ or}$$
$$=O,$$

in which c denotes a number 1, 2, 3 or 4, d denotes a number 0 or 1, $R^{23}$ and $R^{24}$ are identical or different and denote hydrogen, cyclopropyl, cyclopentyl, benzyl, straight-chain or branched alkyl having up to 4 carbon atoms or phenyl which is optionally substituted by fluorine, chlorine or bromine, and/or the carbocycles formed are optionally substituted by a spiro-linked radical of the formula in which w denotes either an oxygen or a sulphur atom, Y and Y' together form a 2- to 6-membered straight-chain or branched alkyl chain, e denotes a number 1, 2, 3, 4 or 5, f denotes a number 1 or 2, $R^{25}$, $R^{26}$, $R^{27}$, $R^{28}$, $R^{29}$, $R^{30}$ and $R^{31}$ are identical or different and denote hydrogen, trifluoromethyl, phenyl, fluorine, chlorine, bromine or straight-chain or branched alkyl or alkoxy each having up to 4 carbon atoms, or $R^{25}$ and $R^{26}$ or $R^{27}$ and $R^{28}$ each together form a straight-chain or branched alkylene chain having up to 4 carbon atoms, or $R^{25}$ and $R^{26}$ or $R^{27}$ and $R^{28}$ each together form a radical of the formula $$W-CH_2$$
$$\quad |$$
$$W-(CH_2)_g,$$

in which

W has the meaning indicated above, g denotes a number 1, 2, 3, 4, 5, 6 or 7, and their salts and N-oxides, with the exception of 5(6H)-quinolone, 3-benzoyl-7,8-dihydro-2,7,7-trimethyl-4-phenyl-.

Very particularly preferred compounds of the formula (I) are those in which

A represents 4-fluoro-phenyl.

Also those compounds in which

E represents isopropyl or cyclopentyl.

A process for the preparation of the compounds of the general formula (I) according to the invention has additionally been found, characterized in that

[A] if D≠aryl, in compounds of the general formula (II)

(II)

in which

A, E, $R^1$ and $R^2$ have the meaning indicated above, the substituent D is synthesized in inert solvents using organometallic reagents in the sense of a Grignard, Wittig or organolithium reaction, or if D represents the radical of the formula $R^9$—T—V—X, in which V denotes an oxygen atom,

[B] either compounds of the general formula (III)

(III)

in which

A, E, X, $R^1$ and $R^2$ have the meaning indicated above, are reacted with compounds of the general formula (IV)

$$R^9-T-Z \qquad (IV),$$

in which $R^9$ and T have the meaning indicated above and z represents halogen, preferably chlorine or bromine, in inert solvents, if appropriate in the presence of a base and/or auxiliary, or

[C] compounds of the general formula (III) are first converted by reaction with compounds of the general formula (V)

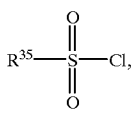

in which
R$^{35}$ represents straight-chain alkyl having up to 4 carbon atoms,
into the compounds of the general formula (VI)

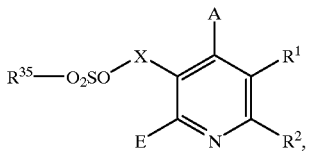

(VI)

in which
A, E, X, R$^1$, R$^2$ and R$^{35}$ have the meaning indicated above,
and then reacted with compounds of the general formula (VII)

$$R^9\text{—T—V—H} \quad (VII),$$

in which
R$^9$, T and V have the meaning indicated above,
and, if appropriate, protective groups are removed,
or
[D] in the case of the compounds of the general formula (Ia)

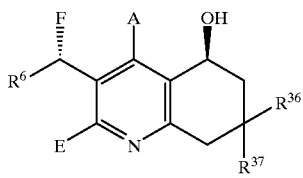

(Ia)

in which
A and R$^6$ have the meaning indicated above,
R$^{36}$ and R$^{37}$ are identical or different and represent trifluoromethyl, halogen, nitro, azido, cyano, cycloalkyl or cycloalkyloxy each having 3 to 7 carbon atoms, or
represent straight-chain or branched alkoxycarbonyl, alkoxy or alkylthio each having up to 6 carbon atoms or straight-chain or branched alkyl having up to 6 carbon atoms, or represent phenyl, benzoyl, thiophenyl or sulphonylbenzyl, which for their part are optionally substituted by halogen, trifluoromethyl, trifluoromethoxy or nitro, or
R$^{36}$ and R$^{37}$ represent one of the abovementioned spiro-linked radicals of the formula

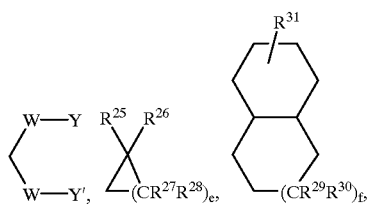

-continued

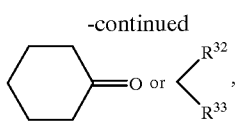

in which
W, Y, Y', R$^{25}$, R$^{26}$, R$^{27}$, R$^{28}$, e, R$^{29}$, R$^{30}$, R$^{31}$, R$^{32}$ and R$^{33}$ have the meaning indicated above,
compounds of the general formula (VIII)

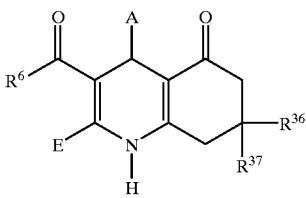

(VIII)

in which
R$^6$, R$^{36}$, R$^{37}$, A and E have the meaning indicated above,
are first oxidized to the compounds of the general formula (IX)

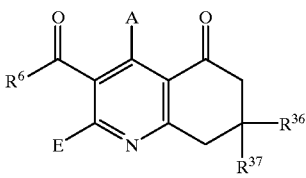

(IX)

in which
R$^6$, R$^{36}$, R$^{37}$, A and E have the meaning indicated above,
these are reacted in a next step by means of an asymmetric reduction to give the compounds of the general formula (X)

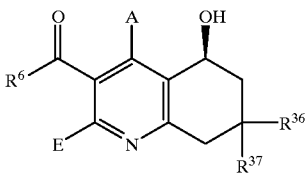

(X)

in which
R$^6$, R$^{36}$, R$^{37}$, A and E have the meaning indicated above,
these are then converted by the introduction of a hydroxyl protective group into the compounds of the general formula (XI)

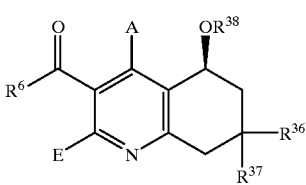

(XI)

in which
R$^6$, R$^{36}$, R$^{37}$, A and E have the meaning indicated above
and $R^{38}$ represents a hydroxyl protective group, preferably a radical of the formula $—SiR^{39}R^{40}R^{41}$, in which $R^{39}$, $R^{40}$ and $R^{41}$ are identical or different and denote $C_1$–$C_4$-alkyl, the compounds of the general formula (XII)

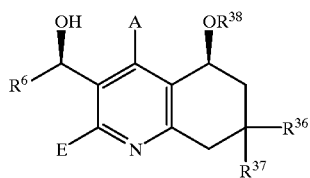

(XII)

in which $R^6$, $R^{36}$, $R^{37}$, $R^{38}$, A and E have the meaning indicated above, are prepared from these in a subsequent step by diastereoselective reduction, and then by introduction of the fluorine substituent using for example fluorinating reagents $SF_4$ derivatives, the DAST, Morph-DAST etc. compounds of the general formula (XIII)

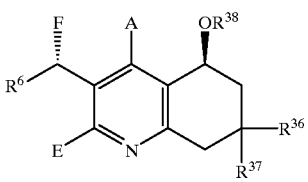

(XIII)

in which $R^6$, $R^{36}$, $R^{37}$, $R^{38}$, A and E have the meaning indicated above, are prepared, and then the hydroxyl protective group is removed according to customary methods, and if appropriate the substituents mentioned under D, E and/or $R^1$ and $R^2$ are varied or introduced according to customary methods.

The processes according to the invention can be illustrated by way of example by the following reaction schemes:

[A]

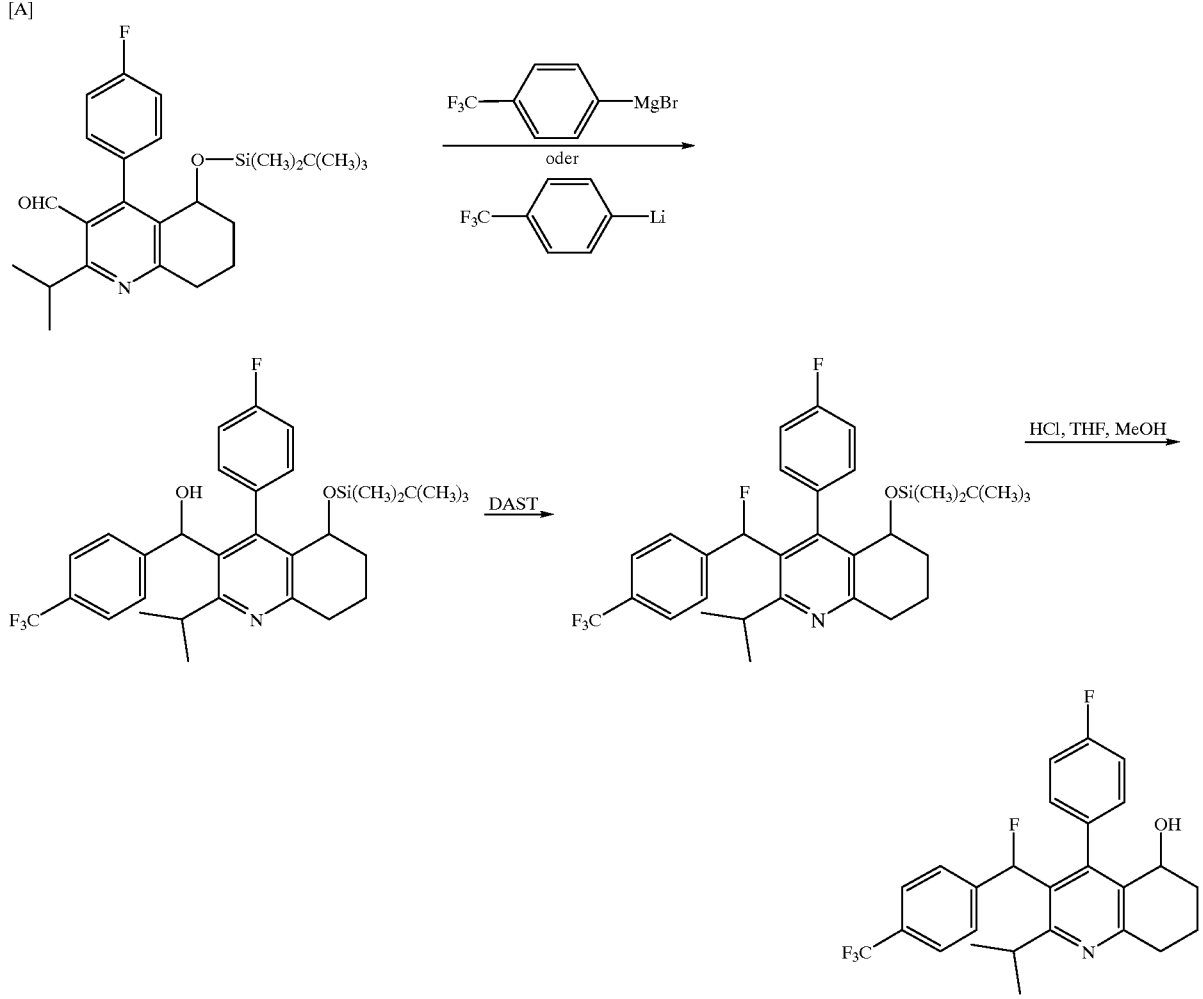

-continued
[B]
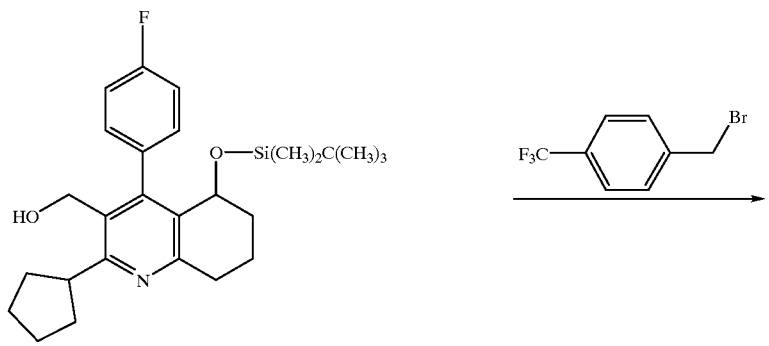
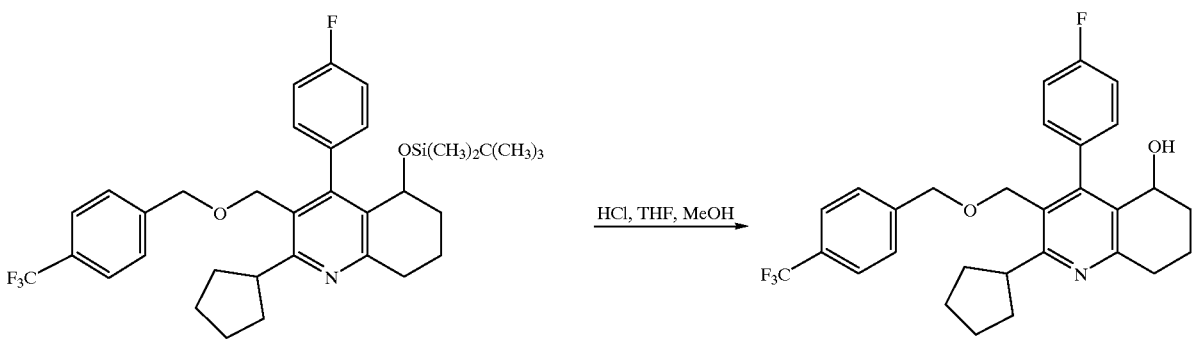
[C]
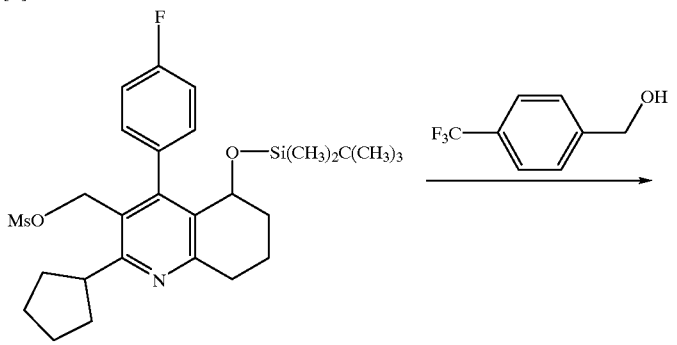
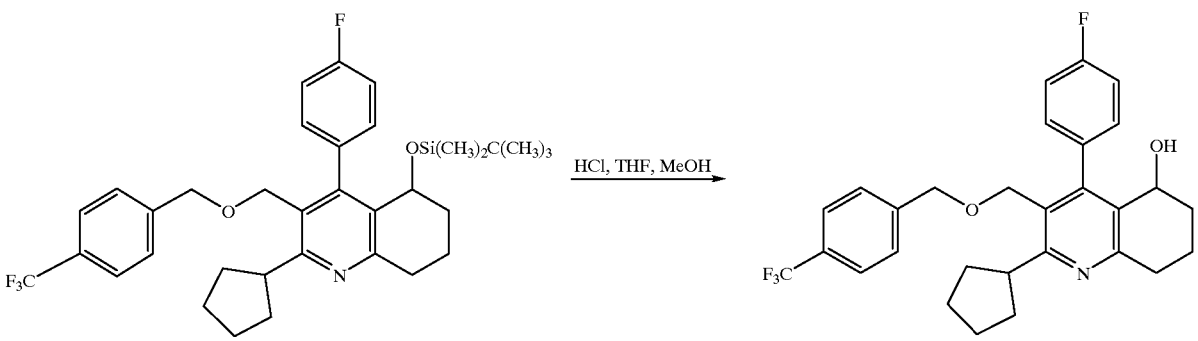
Ms = mesylate

[D]
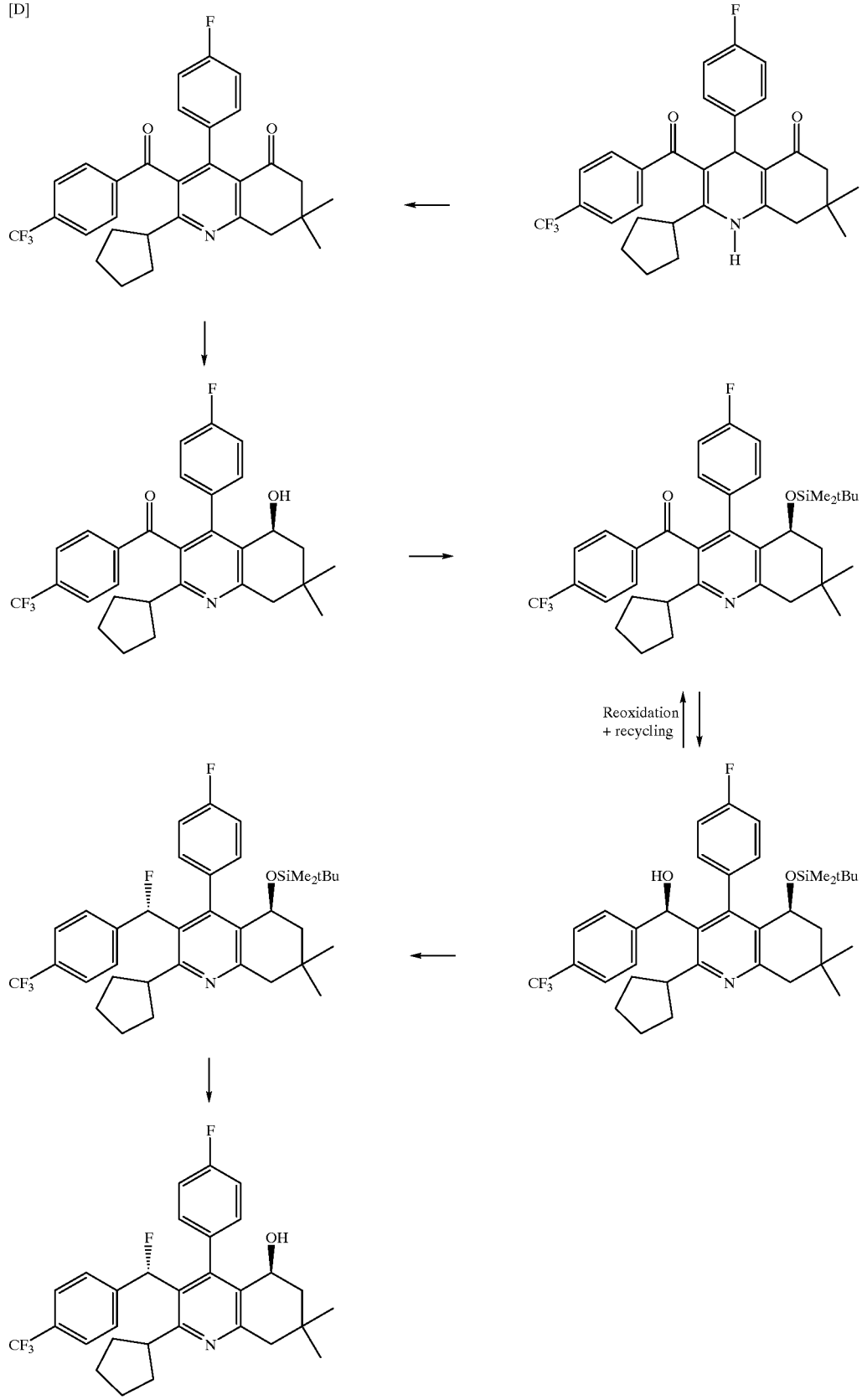

Suitable solvents for all processes are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Dichloromethane is preferred.

Possible bases for the individual steps are the customary strongly basic compounds. These preferably include organolithium compounds such as, for example, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. n-Butyllithium, sodium hydride or lithium diisopropylamide is particularly preferably employed.

The customary inorganic bases are additionally suitable for processes [B] and [C]. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydride or potassium hydroxide is particularly preferably employed.

Suitable organometallic reagents are, for example, systems such as Mg/bromobenzotrifluoride and p-trifluoromethylphenyllithium.

The reductions are in general carried out using reducing agents, preferably using those which are suitable for the reduction of ketones to hydroxyl compounds. Particularly suitable in this context is reduction with metal hydrides or complex metal hydrides in inert solvents, if appropriate in the presence of a trialkylborane. The reduction is preferably carried out using complex metal hydrides such as, for example, lithium borohydride, sodium borohydride, potassium borohydride, zinc borohydride, lithium trialkylborohydride or lithium aluminium hydride or diisobutylaluminium hydride. The reduction is very particularly preferably carried out using diisobutylaluminium hydride and sodium borohydride.

The reducing agent is in general employed in an amount from 1 mol to 6 mol, preferably from 1 mol to 4 mol, relative to 1 mol of the compounds to be reduced.

The reduction in general proceeds in a temperature range from −78° C. to +50° C., preferably from −78° C. to 0° C. in the case of DIBAH, 0° C. to room temperature in the case of NaBH$_4$, particularly preferably at −78° C., in each case depending on the choice of the reducing agent and solvent.

The reduction in general proceeds at normal pressure, but it is also possible to work at elevated or reduced pressure.

The hydrogenation is carried out according to customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range from −20° C. to +100° C., preferably from 0° C. to +50° C., at normal pressure or elevated pressure.

Preferably, the process in case [A] is first carried out using compounds of the general formula (II) in which the carbocycle $R^1/R^2$ is first only substituted by a group —OSiR$^I$R$^{II}$R$^{III}$, in which R$^I$, R$^{II}$ and R$^{III}$ are identical or different and denote phenyl or straight-chain or branched alkyl having up to 5 carbon atoms, and after removal of the protective group the substituent indicated above under R$^{19}$/R$^{20}$ is introduced according to customary methods.

The removal of the protective group is in general carried out in one of the abovementioned alcohols and THF, preferably methanol/THF in the presence of hyrochloric acid in a temperature range from 0° C. to 50° C., preferably at room temperature, and at normal pressure. In particular cases, the removal of the protective group with tetrabutylammonium fluoride (TBAF) in THF is preferred.

Hydroxyl protective groups in the context of the definition indicated above in general represents a protective group from the series: trimethylsilyl, triisopropylsilyl, tert-butyldimethylsilyl, benzyl, benzyloxycarbonyl, 2-nitrobenzyl, 4-nitrobenzyl, tert-butyloxycarbonyl, allyloxycarbonyl, 4-methoxy-benzyl, 4-methoxybenzyloxycarbonyl, tetrahydropyranyl, formyl, acetyl, trichloroacetyl, 2,2,2-trichloroethoxycarbonyl, methoxyethoxymethyl, [2-(tri-methylsilyl)ethoxy]-methyl, benzoyl, 4-methylbenzoyl, 4-nitrobenzoyl, 4-fluorobenzoyl, 4-chlorobenzoyl or 4-methoxybenzoyl. Tetrahydropyranyl, tert-butyldimethylsilyl and triisopropylsilyl are preferred. tert-Butyldimethylsilyl is particularly preferred.

Suitable solvents for the individual steps are ethers such as diethyl ether, dioxane, tetrahydrofuran, glycol dimethyl ether, diisopropyl ether or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene. It is also possible to use mixtures of the solvents mentioned.

Suitable oxidizing agents for the preparation of the compounds of the general formula (IX) are, for example, nitric acid, cerium(IV) ammonium nitrate, 2,3-dichloro-5,6-dicyano-benzoquinone, pyridinium chlorochromate (PCC), pyridinium chlorochromate on basic alumina, osmium tetroxide and manganese dioxide. Manganese dioxide and nitric acid are preferred.

The oxidation is carried out in one of the abovementioned chlorinated hydrocarbons and water. Dichloromethane and water are preferred.

The oxidizing agent is employed in an amount from 1 mol to 10 mol, preferably from 2 mol to 5 mol, relative to 1 mol of the compounds of the general formula (VIII).

The oxidation in general proceeds at a temperature from −50° C. to +100° C., preferably from 0° C. to room temperature.

The oxidation in general proceeds at normal pressure. However, it is also possible to carry out the oxidation at elevated or reduced pressure.

The asymmetric reduction to give the compounds of the general formula (X) is in general carried out in one of the abovementioned ethers or toluene, preferably tertrahydrofuran and toluene.

The reduction is in general carried out using enantiomerically pure 1R,2S-aminoindanol and borane complexes such as BH$_3$×THF, BH$_3$×DMS and BH$_3$×(C$_2$H$_5$)$_2$NC$_6$H$_5$. The system borane diethylaniline/1R,2S-aminoindanol is preferred.

The reducing agent is in general employed in an amount from 1 mol to 6 mol, preferably from 1 mol to 4 mol, relative to 1 mol of the compounds to be reduced.

The reduction in general proceeds at a temperature from −78° C. to +50° C., preferably from 0° C. to 30° C.

The reduction in general proceeds at normal pressure, but it is also possible to work at elevated or reduced pressure.

The introduction of the hydroxyl protective group is carried out in one of the abovementioned hydrocarbons, dimethylformamide or THF, preferably in toluene in the presence of lutidine in a temperature range from −20° C. to +50° C., preferably from −5° C. to room temperature, and at normal pressure.

Reagents for the introduction of the silyl protective group are in general tert-butyldimethylsilyl chloride or tert-butyldimethylsilyltrifluoromethanesulphonate. tert-Butyldimethylsilyltrifluoromethanesulphonate is preferred.

The reduction to the compounds of the general formula (XI) proceeds in one of the abovementioned hydrocarbons, preferably toluene.

The reduction for the preparation of the compounds of the general formula (XII) is in general carried out using customary reducing agents, preferably using those which are suitable for the reduction of ketones to hydroxy compounds. Reduction with metal hydrides or complex metal hydrides in inert solvents, if appropriate in the presence of a trialkylborane, is particularly suitable here. Preferably, the reduction is carried out using complex metal hydrides such as, for example, lithium borohydride, sodium borohydride, potassium borohydride, zinc borohydride, lithium trialkylborohydride, diisobutylaluminium hydride, sodium bis-(2-methoxyethoxy)-dihydroaluminate or lithium aluminium hydride. The reduction is very particularly preferably carried out using sodium bis-(2-methoxyethoxy)-dihydroaluminate.

The reducing agent is in general employed in an amount from 1 mol to 6 mol. preferably from 1 mol ot 3 mol, relative to 1 mol of the compounds to be reduced.

The reduction in general proceeds at a temperature from −20° C. to +110° C., preferably from 0° C. to room temperature.

The reduction in general proceeds at normal pressure, but it is also possible to work at elevated or reduced pressure.

In the reduction to the compounds of the general formula (XII), small residues of the wrong diastereomer remain in the mother liquor. These residues can be reoxidized using customary oxidizing agents such as, for example, pyridinium chlorochromate (PCC) or activated manganese dioxide, in particular using activated manganese dioxide, to protected (XI) and thus subjected to the synthesis cycle without loss of yield.

The introduction of the fluorine substituent is in general carried out in one of the abovementioned hydrocarbons or methylene chloride, preferably in toluene and under a protected gas atmosphere.

Under $SF_4$ derivatives, in general diethylaminosulphur trifluoride (DAST) or 2,2'-bisfluoro-substituted amines such as, for example, diethyl-1,2,3,3,3-hexafluoropropylamine, are prepared.

The reaction in general proceeds at a temperature from −78° C. to 100° C., preferably in the case of dimethylaminosulphur trifluoride at −78° C. to RT and in the case of diethyl-1,1,2,3,3,3-hexafluoropropylamine at room temperature to 80° C.

The removal of the protective group is in general carried out in one of the abovementioned alcohols and THF, preferably methanol/THF in the presence of hydrochloric acid in a temperature range from 0° C. to 50° C., preferably at room temperature, and at normal pressure. In particular cases, the removal of the protective group with tetrabutylammonium fluoride (TBAF) in THF at room temperature is preferred.

Derivatizations which may be mentioned by way of example are the following types of reactions: oxidations, reductions, hydrogenations, halogenation, Wittig/Grignard reactions and amidations/sulphoamidations.

Possible bases for the individual steps are the customary strongly basic compounds. These preferably include organolithium compounds such as, for example, n-butyllithium, sec-butyllithium, tert-butyllithium or phenyllithium, or amides such as, for example, lithium diisopropylamide, sodium amide or potassium amide, or lithium hexamethylsilylamide, or alkali metal hydrides such as sodium hydride or potassium hydride. n-Butyllithium, sodium hydride or lithium diisopropylamide is particularly preferably employed.

Suitable bases are additionally the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen-carbonate. Sodium hydroxide or potassium hydroxide particularly preferably employed.

Suitable solvents for the individual reaction steps are also alcohols such as methanol, ethanol, propanol, butanol or tert-butanol. tert-Butanol is preferred.

It may be necessary to carry out some reaction steps under a protective gas atmosphere.

The halogenations are in general carried out in one of the abovementioned chlorinated hydrocarbons, methylene chloride being preferred.

Suitable halogenating agents are, for example, diethylaminosulphur trifluoride (DAST), morpholino-sulphur trifluoride or $SOCl_2$.

The halogenation in general proceeds in a temperature range from −78° C. to +50° C., preferably from −78° C. to 0° C., in each case depending on the choice of the halogenating agent and solvent.

The halogenation in general proceeds at normal pressure, but it is also possible to work at elevated or reduced pressure.

The compounds of the general formula (II) and (III) are new and can be prepared by a process in which by reaction of the compounds of the general formula (XIV)

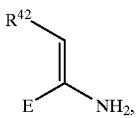

(XIV)

in which

E has the meaning indicated above and $R^{42}$ represents $C_1$–$C_4$-alkoxycarbonyl or aryl (D=aryl), with aldehydes of the general formula (XV)

A—CHO (XV), in which

A has the meaning indicated above, and compounds of the general formula (XVI)

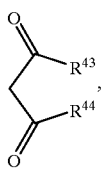
(XVI)

in which
R$^{43}$ and R$^{44}$, including a carbonyl group, encompass the scope of meaning of R$^1$ and R$^2$ indicated above,
the compounds of the general formula (XVII)

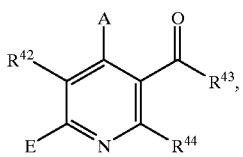
(XVII)

in which
A, E, R$^{42}$, R$^{43}$ and R$^{44}$ have the meaning indicated above,
are prepared
and in the case of the compounds of the general formula (III) a reduction, as described above, to the hydroxymethyl function follows,
and in a last step the alkoxycarbonyl group (R$^{42}$) is converted to an aldehyde group by a reduction/oxidation sequence.

Suitable solvents for the oxidation are ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoramide, acetonitrile, acetone or nitromethane. It is also possible to use mixtures of the solvents mentioned. Methylene chloride is preferred.

Suitable oxidizing agents are, for example, cerium(IV) ammonium nitrate, 2,3-dichloro-5,6-dicyano-benzoquinone, pyridinium chlorochromate (PCC), pyridinium chlorochromate on basic alumina, osmium tetroxide and manganese dioxide.

Sulphur trioxide-pyridine complex in DMSO/methylene chloride and pyridinium chlorochromate on basic alumina are preferred.

The oxidizing agent is employed in an amount from 1 mol to 10 mol, preferably from 2 mol to 5 mol, relative to 1 mol of the compounds of the general formula (XVII).

The oxidation in general proceeds in a temperature range from −50° C. to +100° C., preferably from 0° C. to room temperature.

The oxidation in general proceeds at normal pressure. However, it is also possible to carry out the oxidation at elevated or reduced pressure.

The compounds of the general formulae (IV), (V), (VII), (MV), (XV) and (XVI) are known per se or can be prepared according to customary methods.

The compounds of the general formulae (VI) and (XV) are known in some cases or are new and can then be prepared as described above.

The compounds of the general formulae (IX) and (X) are new as a species and can be prepared as described above.

The compounds of the general formula (VIII) are new and can be prepared by a process in which compounds of the general formulae (XVa), (XVIII) and (XIX)

A—CHO, (XVa)

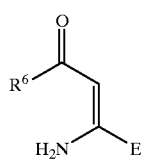 and (XVIII)

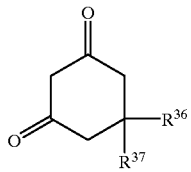
(XIX)

in which
A, E, R$^6$, R$^{36}$ and R$^{37}$ have the meaning indicated above,
are reacted with an acid.

Suitable solvents for the preparation of the compounds of the general formula (VIII) are the abovementioned ethers or alcohols. Diisopropyl ether is preferred.

Suitable acids for the preparation of the compounds of the general formula (VIII) are in general organic carboxylic acids and inorganic acids, such as, for example, oxalic acid, maleic acid, phosphoric acid, fumaric acid and trifluoroacetic acid. Trifluoroacetic acid is preferred.

The acid is in general employed in an amount from 0.1 to 5 mol, preferably 1 mol, relative to 1 mol of the compounds of the general formula (XIX).

The reaction is in general carried out at normal pressure. However, it is also possible to carry out the reaction at elevated or reduced pressure.

The reaction is in general carried out at the reflux temperature of the respective solvent.

The compounds of the general formulae (XV) and (XIX) are known per se or can be prepared by customary methods.

The compounds of the general formula (XVIII) are new and can be prepared by a process in which first, by reaction of the compounds of the general formula (XX)

E—CO$_2$—R$^{45}$ (XX)

in which
E has the meaning indicated above
and
R$^{45}$ represents C$_1$–C$_4$-alkyl, with compounds of the general formula (XXI)

(XXI)

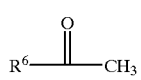

in which
R$^6$ has the meaning indicated above,
in a solvent in the presence of 18-crown-6 ether the compounds of the general formula (XXII)

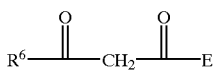

(XXII)

in which

R[6] and E have the meaning indicated above, are prepared and then reacted with ammonium acetate in inert solvents.

Suitable solvents for the first step of the process are the abovementioned ethers and hydrocarbons, tetrahydrofuran being preferred.

Suitable solvents for the reaction with the compounds of the general formula (XXII) are alcohols, such as, for example, methanol, ethanol, propanol or isopropanol. Ethanol is preferred.

All steps of the process are carried out at the respective reflux temperature of the corresponding solvent and at normal pressure.

The compounds of the general formulae (XX) and (XXI) are known in some cases or can be prepared according to known methods.

The compounds of the general formula (XXI) are partially new as a species and can be prepared as described above.

The compounds of the general formulae (I) and (Ia) according to the invention have an unforeseeable spectrum of pharmacological action.

The compounds of the general formulae (I) and (Ia) according to the invention have useful pharmacological properties which are superior in comparison with those of the prior art; in particular they are highly effective inhibitors of the cholesterol ester transfer protein (CETP) and stimulate reverse cholesterol transport. The active compounds according to the invention bring about a lowering of the LDL cholesterol level in the blood with a simultaneous increase in the HDL cholesterol level. They can therefore be used for the treatment and prevention of hyperlipoproteinaemia, dyslipidaemias, hypertriglyceridaemias, hyperlipidaemias or arteriosclerosis.

The pharmacological action of the substances according to the invention was determined in the following test:

CETP Inhibition Testing

Obtainment of CETP

CETP is obtained from human plasma in partially purified form by differential centrifugation and column chromatography and used for the test. To this end, human plasma is adjusted to a density of 1.21 g per ml using NaBr and centrifuged at 4° C. for 18 h at 50,000 rpm. The bottom fraction (d>1.21 g/ml) is applied to a Sephadex®phenyl-sepharose 4B (Pharmacia) column, washed with 0.15 M NaCl/0.001 M trisHCl pH 7.4 and then eluted with distilled water. The CETP-active fractions are pooled, dialysed against 50 mM Na acetate pH 4.5 and applied to a CM-Sepharose® (Pharmacia) column. The column is then eluted using a linear gradient (0–1 M NaCl). The pooled CETP fractions are dialysed against 10 mM trisHCl pH 7.4 and then further purified by chromatography on a Mono Q® column (Pharmacia).

Obtainment of Radiolabelled HDL 50 ml of fresh human EDTA plasma are adjusted to a density of 1.12 using NaBr and centrifuged at 50,000 rpm for 18 h at 4° C. in a Ty 65 rotor. The upper phase is used to obtain cold LDL. The lower phase is dialysed against 3×4 l of PDB buffer (10 mM tris/HCl pH 7.4, 0.15 mM NaCl, 1 mM EDTA, 0.02% $NaN_3$). 20 μl of $^3$H-cholesterol (Dupont NET-725; 1 μC/μl dissolved in ethanol) are then added per 10 ml of retentate volume and the mixture is incubated under $N_2$ at 37° C. for 72 h.

The mixture is then adjusted to the density 1.21 using NaBr and centrifuged at 20° C. for 18 h at 50,000 rpm in the Ty 65 rotor. The upper phase is recovered and the lipoprotein fractions are purified by gradient centrifugation. To this end, the isolated, labelled lipoprotein fraction is adjusted to a density of 1.26 using NaBr. Each 4 ml of this solution are covered with a layer of 4 ml of a solution of density 1.21 and 4.5 ml of a solution of 1.063 (density solutions from PDB buffer and NaBr) in centrifuge tubes (SW 40 rotor) and then centrifuged in the SW 40 rotor for 24 h at 38,000 rpm and 20° C. The intermediate layer lying between the densities 1.063 and 1.21 and containing the labelled HDL is dialysed at 4° C. against 3×100 volumes of PDB buffer.

The retentate contains radiolabelled $^3$H-CE-HDL which, adjusted to about $5×10^6$ cmp per ml, is used for the test.

CETP Test

To test the CETP activity, the transfer of $^3$H-cholesterol ester from human HD lipoproteins to biotinylated LD lipoproteins is measured.

The reaction is ended by addition of streptavidin-SPA®beads (Amersham) and the transferred radioactivity is determined directly in a liquid scintillation counter.

In the test mixture, 10 μl of HDL-$^3$H-cholesterol ester (~50,000 cpm) are incubated at 37° C. for 18 h with 10 μl of biotin-LDL (Amersham) in 50 mM Hepes/0.15 M NaCl/0.1% bovine serum albumin/0.05% $NaN_3$ pH 7.4 with 10 μl of CETP (1 mg/ml) and 3 μl of solution of the substance to be tested (dissolved in 10% DMSO/1% RSA). 200 μl of the SPA-streptavidin bead solution (TRKQ 7005) are then added, the mixture is incubated further for 1 h with shaking and then measured in the scintillation counter. As controls, corresponding incubations with 10 μl of buffer, 10 μl of CETP at 4° C. and 10 μl of CETP at 37° C. are used.

The activity transferred into the control mixtures with CETP at 37° C. is rated as 100% transfer. The substance concentration at which this transfer is reduced by half is indicated as the $IC_{50}$ value.

In Table A which follows, the $IC_{50}$ values (mol/l) are indicated for CETP inhibitors:

Table A

| EXAMPLE | $IC_{50}$ value (mol/l) | EXAMPLE | $IC_{50}$ value (mol/l) |
|---|---|---|---|
| 76 | $6 × 10^{-9}$ | 291 | $3 × 10^{-8}$ |
| 90 | $6 × 10^{-8}$ | 300 | $2 × 10^{-10}$ |
| 166 | $1 – 1.8 × 10^{-8}$ | 312 | $6 × 10^{-8}$ |
| 195 | $7.5 × 10^{-7}$ | 313 | $2 × 10^{-10}$ |
| 237 | $8 × 10^{-7}$ | 319 | $5 × 10^{-8}$ |
| 244 | $6 × 10^{-8}$ | 329 | $1.5 × 10^{-9}$ |

Ex vivo Activity of the Compounds According to the Invention

Syrian golden hamsters from in-house breeding are anaesthetized after fasting for 24 hours (0.8 mg/kg of atropine, 0.8 mg/kg of Ketavet® s.c., 30'later 50 mg/kg of Nembutal i.p.). The jugular vein is then exposed and cannulated. The test substance is dissolved in a suitable solvent (as a rule Adalat placebo solution: 60 g of glycerol, 100 ml of $H_2O$, PEG-400 to 1000 ml) and administered to the animals via a PE catheter inserted in the jugular vein. The control animals receive the same volume of solvent without test substance. The vein is then tied off and the wound is closed. The administration of the test substances can also be carried out p.o., by orally administering the substances dissolved in DMSO and suspended in 0.5% Tylose by means of a stomach tube. The control animals receive identical volumes of solvent without test substance.

After various times—up to 24 hours after administration—blood (about 250 µl) is taken from the animals by puncture of the retro-orbital venous plexus. Clotting is ended by incubation at 4° C. overnight, then centrifugation is carried out at 6000×g for 10 minutes. In the serum thus obtained, CETP activity is determined by the modified CETP test. As for the CETP test described above, the transfer of $^3H$-cholesterol ester from HD lipoproteins to biotinylated LD lipoproteins is measured.

The reaction is ended by addition of Streptavidin-SPA®beads (Amersham) and the transferred radioactivity is determined directly in the liquid scintillation counter.

The test mixture is carried out as described under "CETP test". For the testing of the serum, only 10 µl of CETP are replaced by 10 µl of the corresponding serum samples. As controls, corresponding incubations with sera of untreated animals are used.

The activity transferred in the control mixtures with control sera is rated as 100% transfer. The substance concentration at which this transfer is reduced to a half is indicated as the $ED_{50}$ value.

TABLE B $ED_{50}$ values for ex vivo activity

| Example No. | $ED_{50}$ | % Inhibition at 30 mg/kg |
|---|---|---|
| 115 | <30 mg/kg | 61.9 |
| 117 | <30 mg/kg | 86.0 |
| 170 | <30 mg/kg | 60.1 |
| 181 | >30 mg/kg | 46.4 |
| 184 | <30 mg/kg | 53.5 |

In vivo Activity of the Compounds According to the Invention

In experiments to determine the oral action on lipoproteins and triglycerides, test substance dissolved in DMSO and 0.5% Tylose suspended by means of a stomach tube are administered orally to Syrian golden hamsters from in-house breeding. To determine the CETP activity, blood (about 250 µl) is taken by retro-orbital puncture before the start of the experiment. The test substances are then administered orally by means of a stomach tube. The control animals receive identical volumes of solvents without test substance. The feed is then withdrawn from the animals and blood is taken at various times—up to 24 hours after substance administration—by puncture of the retro-orbital venous plexus. Clotting is ended by incubation at 4° C. overnight, then centrifugation at 6000×g is carried out for 10 minutes. In the serum thus obtained, the content of cholesterol and triglycerides is determined with the aid of modified commercially available enzyme tests (cholesterol enzymatic 14366 Merck, triglycerides 14364 Merck). Serum is suitably diluted using physiological saline solution.

100 µl of serum dilution are mixed with 100 µl of test substance in 96-hole plates and incubated at room temperature for 10 minutes. The optical density is then determined at a wavelength of 492 nm using an automatic plate-reading apparatus. The triglyceride or cholesterol concentration contained in the samples is determined with the aid of a standard curve measured in parallel.

The determination of the content of HDL cholesterol is carried out according to the manufacturer's instructions after precipitation of the ApoB-containing lipoproteins by means of a reagent mixture (Sigma 352-4 HDL cholesterol reagent).

TABLE C

HDL rise in in vivo experiments

| Example No. | Dose (mg/kg) | % HDL rise |
|---|---|---|
| 76 | 2 × 3 | +15.81 |
| 91 | 2 × 3 | +12.58 |
| 209 | 2 × 3 | +25.94 |
| 211 | 2 × 3 | +7.54 |
| 237 | 2 × 3 | +21.03 |

In vivo Activity in Transgenic hCETP Mice

Transgenic mice from in-house breeding (Dinchuck, Hart, Gonzalez, Karmann, Schmidt, Wirak; BBA (1995), 1295, 301) were administered the substances to be tested in the feed. Before the start of the experiment, blood was taken retro-orbitally from the mice in order to determine cholesterol and triglycerides in the serum. The serum was obtained as described above for hamsters by incubation at 4° C. overnight and subsequent centrifugation at 6000×g. After one week, blood was again taken from the mice in order to determine lipoproteins and triglycerides. The change in the parameters measured is expressed as a percentage change compared with the starting value.

TABLE D

| Example No. | HDL | LDL | Triglycerides |
|---|---|---|---|
| 76 (400 ppm) | +31.25% | −15.3% | −11.7% |

The invention additionally relates to the combination of cycloalkano-pyridines of the general formulae (I) and (Ia) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formulae (I) and (Ia) according to the invention is preferred.

The compounds according to the invention can furthermore be used in combination with cholesterol-lowering vastatins or ApoB-lowering principles in order to treat dyslipidaemias, combined hyperlipidaemias, hypercholesterolaemias or hypertriglyceridaemias.

The combinations mentioned can also be employed for the primary or secondary prevention of coronary heart disease (e.g. myocardial infarct).

Vastatins in the context of the invention are, for example, lovastatin, simvastatin, pravastatin, fluvastatin, atorvastatin and cerivastatin. ApoB-lowering agents are, for example, MTP inhibitors.

The combination of cerivastatin or ApoB inhibitors with one of the abovementioned compounds of the general formulae (I) and (Ia) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of approximately 0.5 to 90% by weight of the total mixture, i.e. in amounts which are adequate in order to achieve the dosage range indicated.

The formulations are prepared, for example, by extending the active compounds with solvents and/or excipients, if appropriate using emulsifiers and/or dispersants, it being possible, for example, when water is used as a diluent, optionally to use organic solvents as auxiliary solvents.

Administration is carried out intravenously, parenterally, perlingually or preferably orally in a customary manner.

In the case of parenteral administration, solutions of the active compound can be employed using suitable liquid excipient materials.

In general, it has proved advantageous in the case of intravenous administration to administer amounts of approximately 0.001 to 1 mg/kg, preferably of approximately 0.01 to 0.5 mg/kg of body weight to achieve effective results, and in the case of oral administration the dose is approximately 0.01 to 20 mg/kg, preferably 0.1 to 10 mg/kg of body weight.

In spite of this, if appropriate it may be necessary to deviate from the amounts mentioned, mainly depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

Abbreviations Used

Cy=cyclohexane
EA=ethyl acetate
PE=petroleum ether
THF=tetrahydrofuran
DAST=diethylamino-sulphur trifluoride
PTS=para-toluenesulphonic acid
PDC=pyridinium dichromate
PE/EA=petroleum ether/ethyl acetate
Tol=toluene Starting Compounds

EXAMPLE I

Methyl 4-(4-fluorophenyl)-2-isopropyl-5-oxo-1,4,5,6,7,8-hexahydroquinoline-3-carboxylate

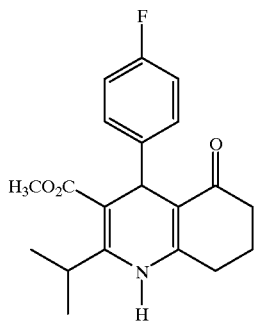

50.14 g (0.404 mol) of p-fluorobenzaldehyde, 45.3 g (0.404 mol) of 1,3-cyclohexanedione and 57.89 g (0.404 mol) of methyl 3-amino-4-methyl-pent-2-en-oate are boiled under reflux for 60 hours in 1000 ml of ethanol. The mixture is cooled to room temperature and concentrated to dryness. The residue is dissolved hot in 500 ml of toluene, the solution is treated with cooling with 1 l of petroleum ether and the product which crystallizes out is filtered off with suction.

Yield: 100.8 g (72.6% of theory)

$R_f$=0.15 (toluene/EA 8:1)

EXAMPLE II

Methyl 4-(4-fluorophenyl)-2-isopropyl-5-oxo-5,6,7,8-tetrahydroquinoline-3-carboxylate

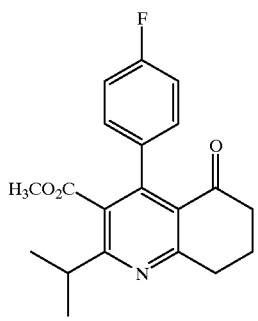

30.44 g (0.1341 mol) of 2,3-dichloro-5,6-dicyano-p-benzoquinone (DDQ) are added to a solution of 46.04 g (0.1341 mol) of the compound from Example I in 645 g of dichloromethane p.a. and the mixture is stirred overnight at room temperature. The solid is then filtered off with suction through 500 ml of silica gel 60 and washed with 700 ml of dichloromethane, and the combined filtrates are concentrated to dryness.

Yield: 24.2 g (52.87% of theory)

$R_f$=0.54 (toluene/EA 8:2)

EXAMPLE III

Methyl 4-(4-fluorophenyl)-2-isopropyl-5-hydroxy-5,6,7,8-tetrahydroquinoline-3-carboxylate

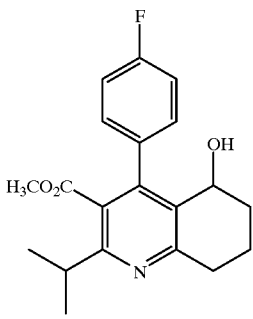

70.64 g (0.207 mol) of the compound from Example II are dissolved under argon in 706 g of toluene p.a., the solution is cooled to −78° C. and 228 ml (0.228 mol; 1.1 eq.) of diisobutylaluminium hydride (DIBAL-H; 1.0 molar in toluene) are added dropwise in the course of 20 min. After stirring at −78° C. for 5 min, 35 ml (0.15 eq. of DIBAL-H are again added and the mixture is stirred for 10 min. 500 ml of 20% strength potassium sodium tartrate solution are then added dropwise at −78° C., the temperature slowly rising to 20° C. After a stirring time of 1 hour, the aqueous phase is separated off and extracted twice with ethyl acetate, and the combined organic phases are dried over sodium sulphate, filtered and concentrated. The residue is purified by chromatography on 1000 ml of silica gel 60 using toluene, toluene/EA mixtures (9:1, 8:2). The fractions containing the desired compound are collected, concentrated down to 100 ml and treated with petroleum ether. The precipitated crystallizate is filtered off with suction and dried overnight in a high vacuum.

Yield: 1st fraction: 61.69 g (86.8% of theory)

Yield: 2nd fraction: 6.34 g (8.9% of theory)

$R_f$=0.14 (toluene/EA 9: 1)

EXAMPLE IV

Methyl 5-(tert-butyldimethylsilyloxy)-4-(4-fluorophenyl)-2-i sopropyl-5,6,7,8 -tetrahydroquinoline-3-carboxylate

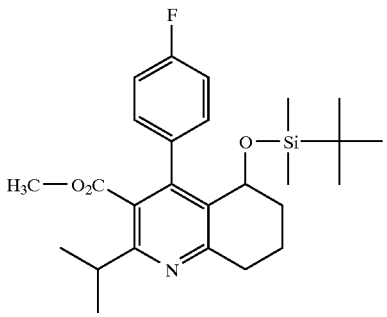

68.0 g (0.198 mol) of the compound from Example III are dissolved in 340 g of DMF p.a. and are treated successively with 59.69 g (0.396 mol; 2 eq.) of tert-butyldimethylsilyl chloride, 48.484 g (0.713 mol; 3.6 eq.) of imidazole and 0.484 g (0.00396 mol, 0.02 eq.) of N-dimethylaminopyridine. The mixture is stirred overnight at room temperature, partitioned in 800 ml of ammonium chloride solution and 400 ml of ethyl acetate and adjusted to a pH of 5 to 6 using 6 molar hydrochloric acid. The organic phase is separated off, the aqueous phase is extracted twice more with ethyl acetate, and the combined organic phases are dried over sodium sulphate, filtered and concentrated. The residue—dissolved in toluene—is applied to 1800 ml of silica gel, and eluted initially with toluene and later with toluene/EA (9:1). After concentration of the eluates a white, crystalline product is obtained.

Yield: 87.5 g (96.7% of theory)

$R_f$=0.68 (toluene/EA 9:1)

EXAMPLE V 5-(tert-Butyldimethylsilyloxy)-4-(4-fluorophenyl)-3-hydroxymethyl-2-isopropyl-5,6,7,8-tetrahydroquinoline

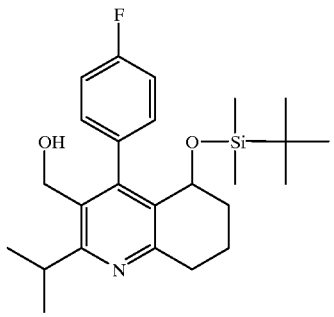

87.4 g (0.191 mol) of the compound from Example IV are dissolved in 500 g of toluene p.a. and cooled to −78° C. under argon. 690 ml (0.690 mol; 3.61 eq.) of DEBAL-H (1.0 molar in toluene) are added dropwise in 1 hour and the mixture is then stirred at −78° C. for a further 1.5 hours. 30 ml of potassium sodium tartrate solution are cautiously added to the solution cooled to −78° C. and it is stirred at −78° C. for 30 min. The mixture is then allowed to rise to room temperature, 400 ml of potassium sodium tartrate solution are poured in and the mixture is diluted with ethyl acetate. Finally, a further 1.2 l of potassium sodium tartrate solution are added, two almost clear solutions gradually being formed. The organic phase is separated off, and the aqueous phase is extracted a further two times with ethyl acetate. The combined organic phases are dried using sodium sulphate, filtered and concentrated. The semisolid residue is dissolved in 400 ml of toluene, and the solution is applied to 1100 ml of silica gel 60 which has previously been conditioned with toluene and eluted successively with toluene and toluene/EA (9:1). The fractions which contain the desired compound are concentrated and the oil recovered is treated with petroleum ether, a crystal magma being precipitated.

Yield: 75.52 g (92.0% of theory)

$R_f$=0.28 (toluene/EA 9:1)

EXAMPLE VI 5-(tert-Butyldimethylsilyloxy)-4-(4-fluorophenyl)-2-isopropyl-5,6,7,8-tetrahydroquinoline-3-carbaldehyde

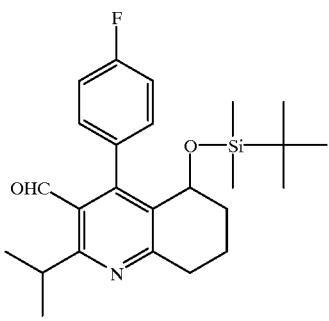

31.8 g (0.312 mol; 2 eq.) of neutral alumina and 67.3 g (0.312 mol; 2 eq.) of pyridinium chlorochromate (PCC) are added to a solution of 67.1 g (0.156 mol) of the compound from Example V in 671 g of dichloromethane and the mixture is stirred at room temperature for 1.5 hours. The reaction solution is applied to 1100 ml of silica gel 60 (dry) and then eluted first with toluene and later with ethyl acetate/methanol (9:1). The fractions which contain the desired compound are concentrated, and the precipitated material is filtered off with suction and washed with a little toluene. The material obtained is then dissolved in 100 ml of toluene, and the solution is applied to 250 ml of silica gel 60 and eluted with toluene and toluene/EA (9:1). The eluates are concentrated and the resulting oil is crystallized using petroleum ether.

Yield: 1st fraction: 28.8 g (43.1% of theory)

Yield: 2nd fraction: 10.05 g (15.1% of theory)

$R_f$=0.72 (toluene/EA 9:1)

EXAMPLE VII 5-(tert-Butyldimethylsilyloxy)-4-(4-fluorophenyl)-3-[hydroxy-(4-trifluoro-methylphenyl)-methyl]-2-isopropyl-5,6,7,8-tetrahydroquinoline (dia A/dia B mixture)

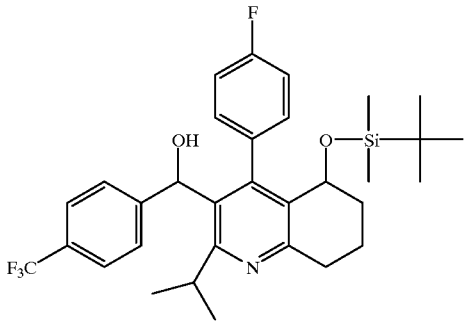

341 mg (14.03 mmol; 6 eq.) of magnesium turnings are initially introduced into 30 ml of TBF p.a., the mixture is heated to reflux under argon and 1.052 g (4.676 mmol; 2 eq.) of 4-bromobenzotrifluoride are added dropwise in pure form by means of syringe. The mixture is boiled under reflux for 45 min, then allowed to cool to room temperature (Grignard reagent). 1.0 g (2.338 mmol) of the compound from Example VI are dissolved in 20 ml of THF p.a., cooled to about −78° C. under argon and the Grignard reagent is then added with stirring. The cooling bath is removed and the mixture is stirred for 1 hour. The reaction solution is partitioned in 200 ml of conc. ammonium chloride solution and 250 ml of ethyl acetate with stirring, the organic phase is separated off, the aqueous phase is extracted a further two times with ethyl acetate, the combined organic phases are dried using sodium sulphate, filtered and concentrated, and the residue is dried overnight in a high vacuum.

Yield: 1.18 g (97.5% of theory; dia A/dia B mixture)

The separation of the two pairs of diastereomers (dia A and dia B) is carried out by chromatography on 100 ml of silica gel 60, conditioned with cyclohexane. The diastereomer mixture—dissolved in 4 ml of cyclohexane—is eluted on silica gel 60, first with cyclohexane and then with cyclohexane/THF (9:1). After concentration of the fractions the two pairs of diastereomers are obtained.

Yield: dia A: 789 mg (65.2% of theory)

$R_f$=0.42 (Cy/THF 9:1)

Yield: dia B: 410 mg (33.9% of theory)

$R_f$=0.24 (Cy/THF 9:1)

EXAMPLE VIII 5-(tert-Butyldimethylsilyloxy)-4-(4-fluorophenyl)-3-[fluoro-(4-trifluoro-methylphenyl)-methyl]-2-isopropyl-5,6,7,8-tetrahydroquinoline (dia A/dia B mixture)

0.302 ml of diethylaminosulphur trifluoride (DAST) are added at −78° C. under argon to a solution of 876 mg (1.521 mmol) of the diastereomer mixture A/B from Example VII in 70 ml of dichloromethane p.a. by means of syringe, then the cooling bath is taken away and the mixture is stirred for 30 min. After this, the reaction solution is stirred into ethyl acetate/ammonium chloride solution, the organic phase is separated off, the aqueous phase is extracted a further three times with ethyl acetate, the whole organic extract is dried using sodium sulphate, filtered and concentrated, and the residue is dried in a high vacuum.

Yield: 690 mg (78.5% of theory)

$R_f$=0.57 (toluene/EA 9:1)

EXAMPLE IX 5-(tert-Butyldimethylsilyloxy)-4-(4-fluorophenyl)-3-[fluoro-(4-trifluoromethylphenyl)-methyl]-2-isopropyl-5,6,7,8-tetrahydroquinoline (dia A)

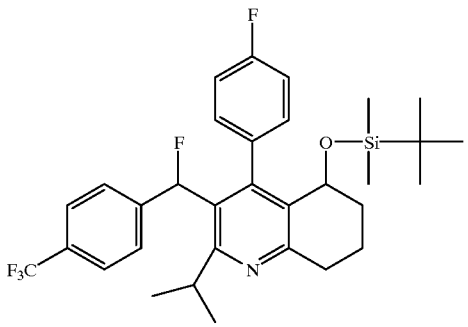

Analogously to Example VIII, 250 mg (0.436 mmol) of the compound dia A from Example VII in 10 ml of dichloromethane p.a. are reacted at −78° C. with 0.086 ml (0.654 mmol; 1.5 eq.) of DAST.

Yield: 233 mg (92.8% of theory)

$R_f$=0.76 (Cy/TBF 9:1)

EXAMPLE X 5-(tert-Butyldimethylsilyloxy)-4-(4-fluorophenyl)-3-[fluoro-(4-trifluoromethyl-phenyl)-methyl]-2-isopropyl-5,6,7,8-tetrahydroquinoline (dia B)

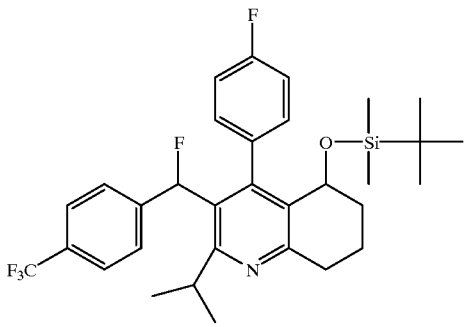

Analogously to Example VIII, 250 mg (0.436 mmol) of the compound dia B from Example VII in 10 ml of dichloromethane p.a. are reacted at −78° C. with 0.086 ml (0.654 mmol; 1.5 eq.) of DAST.

Yield: 246 mg (98.4% of theory)

$R_f$=0.76 (Cy/THF 9:1)

EXAMPLE XI

8-Bromo-5-(tert-butyldimethylsilyloxy)-4-(4-fluorophenyl)-3-[fluoro-(4-trifluoromethylphenyl)-methyl]-2-isopropyl-5,6,7,8-tetrahydroquinoline

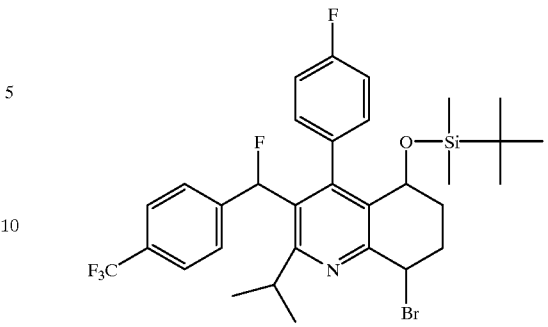

9.3 g (52.0 mmol) of N-bromosuccinimide and 500 mg of azobisisobutyronitrile are added under argon to a solution of 18.7 g (32.5 mmol) of the compound from Example X in 500 ml of carbon tetrachloride. The mixture is heated to reflux, vigorous reaction commencing after 10 min. After 2.5 hours, the mixture is cooled to room temperature, solid is filtered off with suction and the filtrate is concentrated. The crude product is eluted on silica gel 60 using Cy/EA 15:1, the fractions are concentrated and the residue is dried in a high vacuum.

Yield: 9.9 g (47% of theory)

$R_f$=0.58 (Cy/EA 9:1)

EXAMPLE XII

8-Butyl-5-(tert-butyldimethylsilyloxy)-4-(4-fluorophenyl)-3-[fluoro-(4-trifluoromethylphenyl)-methyl]-2-isopropyl-5,6,7,8-tetrahydroquinoline

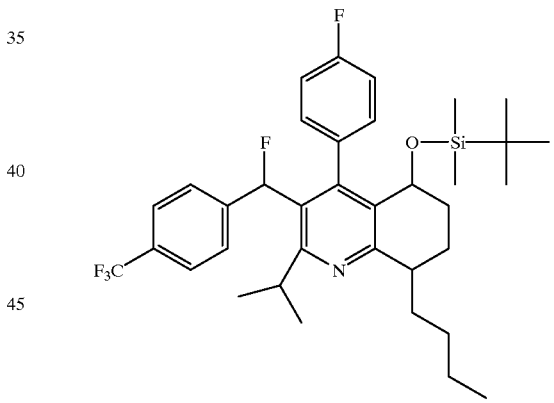

179 mg of copper(I) cyanide (2 mmol) are suspended in 3 ml of absolute toluene under argon and the solvent is stripped off in vacuo. The residue is then suspended in 2.6 ml of absolute THF and cooled to −65° C. 2.5 ml of 1.6 molar N-butyllithium solution (4 mmol) are added dropwise at this temperature and the mixture is stirred for 1 hour with increase in the temperature to −30° C. in between. A solution of 654 mg (1 mmol) of the compound from Example XI in 2 ml of absolute THF is added dropwise to this solution at −65° C. and the mixture is stirred for 1 hour. For working up, it is treated with a mixture of 4.5 ml of saturated ammonium chloride solution and 0.5 ml of conc. ammonia solution, diluted with 30 ml of water and extracted three times with 15 ml of diethyl ether each time. The combined organic phases are dried over sodium sulphate, filtered and concentrated. The crude product is eluted on silica gel (0.04–0.0063 mm) using Cy:EA 98:2.

Yield: 200 mg (32% of theory)

$R_f$=0.33 (Cy:EA 98:2)

EXAMPLE XII 4-(4-Fluorophenyl)-3-[fluoro-(4-trifluoromethylphenyl)-methyl]-2-isopropyl-5,6-dihydroquinolin-5-ol

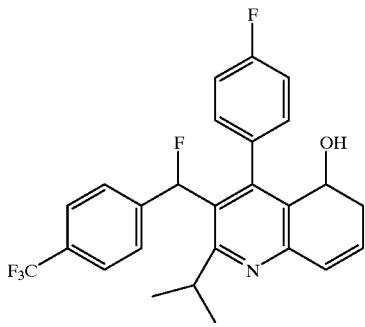

10.9 ml of 1.1 molar tetrabutylammonium fluoride solution are added dropwise at room temperature to a solution of 1.3 g (2 mmol) of 8-bromo-5-(tert-butyl-silyloxy)-4-(4-fluorophenyl)-3-[fluoro-(4-trifluoromethylphenyl)methyl]-2-isopropyl-5,6,7,8-tetrahydroquinoline in 13 ml of THF. After 1 h, a mixture of 100 ml of water and 50 ml of toluene is stirred in. The phases are separated and the aqueous phase is reextracted with toluene. The combined organic phases are washed with water until neutral, dried over sodium sulphate and concentrated. The crude product is eluted on silica gel (0.04–0.063 mm) using Cy/EA 8:2, the fraction is concentrated and the product is crystallized.

Yield: 640 mg (70% of theory)

$R_f$=0.17 (Cy/EA 8:2)

EXAMPLE XIV

1-Cyclopentyl-3-(4-trifluoromethylphenyl)-propane-1,3-dione

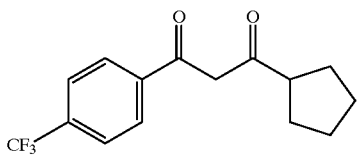

1.97 kg of potassium tert-butoxide, 2.26 kg of methyl cyclopentanecarboxylate, 1.66 kg of p-trifluoromethylacetophenone and 36 g of 18-crown-6 ether were refluxed in 18 liters of tetrahydrofuran for 4 hours. Quenching of the reaction was carried out using 16 liters of 10% strength hydrochloric acid at room temperature. The aqueous phase was extracted with ethyl acetate and the combined organic phases were washed with saturated sodium chloride solution. After distilling off the solvent, the residue was distilled in an oil-pump vacuum at 1.5 mbar. 1.664 kg of 1-cyclopentyl-3-(4-trifluoromethylphenyl) propane-1,3-dione resulted as an oil, which crystallized completely on allowing to stand.

Boiling point: 138–145° C./1.5 mbar.

EXAMPLE XV

3-Amino-3-cyclopentyl-l1 (4-trifluoromethylphenyl)-propenone

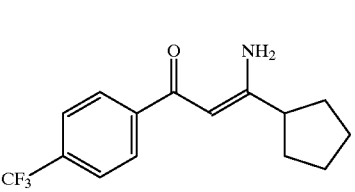

1622.6 g of 1-cyclopentyl-3-(4-trifluoromethylphenyl) propane-1,3-dione and 730 g of ammonium acetate were refluxed overnight in 4.9 liters of ethanol. The ethanol was stripped off in vacuo and the residue was taken up in 4 liters of methylene chloride. The solution was washed once with water and twice with saturated sodium hydrogen-carbonate solution and dried using sodium sulphate. After distilling off the methylene chloride, the residue was recrystallized from 6 liters of hot cyclohexane. After drying, 1018 g of colorless crystals resulted having a purity of 98.6% according to HPLC.

Melting point: 106° C.

TLC: $R_f$=0.2 (toluene/ethyl acetate 4:1)

EXAMPLE XVI

2-Cyclopentyl-4-(4-fluorophenyl)-7,7-dimethyl-3-(4-trifluoromethylbenzoyl)-4,6,7,8-tetrahydro-1H-quinolin-5-one

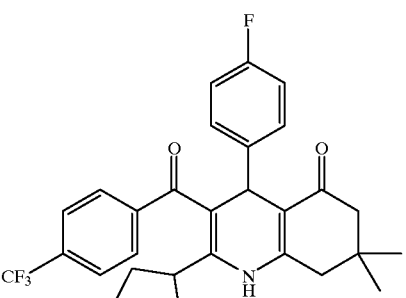

984 g of 3-amino-3-cyclopentyl-1-(4-trifluoromethylphenyl)propenone, 714 g of dimedone, 647.8 g of p-fluorobenzaldehyde and 139.3 ml of trifluoroacetic acid were refluxed in 15 liters of diisopropyl ether for 5 hours. After cooling, the precipitated crystals were filtered off with suction, washed with diisopropyl ether and dried. 843 g resulted, having a purity according to HPLC of 98.9%.

Melting point: 117° C.

TLC: $R_f$=0.2 (toluene/ethyl acetate 4:1)

Preparation Examples

Example 1

4-(4-Fluorophenyl)-3-[fluoro-(4-trifluoromethyl-phenyl)-methyl]-2-isopropyl-5,6,7,8-tetrahydroquinolin-5-ol (dia A/dia B mixture)

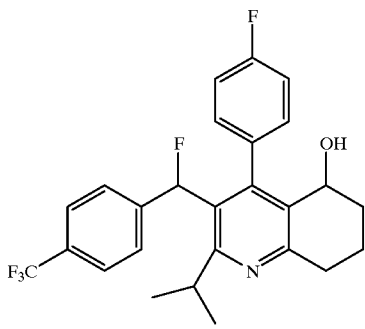

10 ml of 3 molar hydrochloric acid are added to 680 mg (1.177 mmol) of the compound from Example VIII, dissolved in 30 ml of methanol and 15 ml of THF, and the mixture is stirred at room temperature for 1 hour. The reaction solution is stirred into 100 ml of saturated sodium hydrogen carbonate solution, which is covered with a layer of 100 ml of ethyl acetate. The organic phase is separated off, and the aqueous phase is extracted a further two times with ethyl acetate. The combined organic phases are washed once with saturated sodium chloride solution, dried over sodium sulphate, filtered and concentrated. The residue is chromatographed on 50 g of silica gel 60 using toluene and toluene/EA (8:2) successively.

Yield: 240 mg (44.2% of theory)

$R_f$=0.19 (toluene/EA 9:1)

Example 2

4-(4-Fluorophenyl)-3-[fluoro-(4-trifluoromethyl-phenyl)-methyl]-2-isopropyl-5,6,7,8-tetrahydroquinolin-5-ol (dia A)

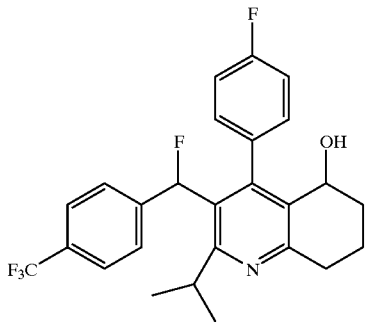

Analogously to Example 1, 223 mg (0.387 mmol) of the compound from Example IX in 9 ml of methanol and 9 ml of THF are stirred overnight at room temperature with 3 ml of 3 molar hydrochloric acid. The chromatography of the crude product is carried out on 40 ml of silica gel 60, which has previously been equilibrated with cyclohexane and then eluted using cyclohexane with addition of THF at a gradient of 10 to 20%.

Yield: 167 mg (93.3% of theory)

$R_f$=0.43 (Cy/THF 8:2)

Example 3

4-(4-Fluorophenyl)-3-[fluoro-(4-trifluoromethyl-phenyl)-methyl]-2-isopropyl-5,6,7,8-tetrahydroquinolin-5-ol (dia B)

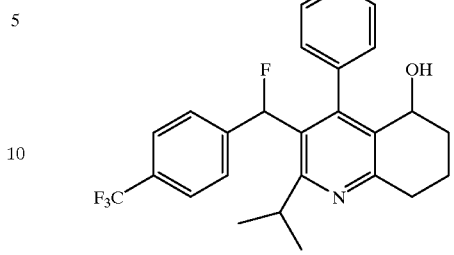

Analogously to Example 1, 236 mg (0.410 mmol) of the compound from Example X in 9 ml of methanol and 9 ml of THF are stirred overnight at room temperature with 3 ml of 3 molar hydrochloric acid. The chromatography of the crude product is carried out on 40 ml of silica gel 60, which has previously been equilibrated with cyclohexane, using cyclohexane with addition of THF at a gradient of 10 to 20%.

Yield: 182 mg (98.9% of theory)

$R_f$=0.41 (Cy/THF 8:1)

Example 4 and Example 5

4-(4-Fluorophenyl)-3-[fluoro-(4-trifluoromethyl-phenyl)-methyl]-2-isopropyl-5,6,7,8-tetrahydroquinolin-5-ol (enantiomer I and II)

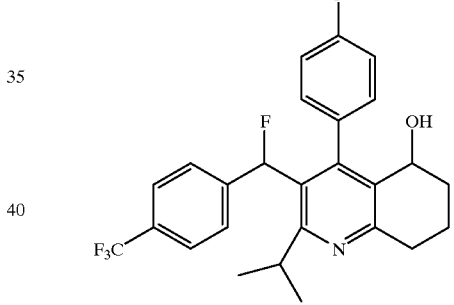

82 mg of the compound dia B from Example 3 are dissolved in a mixture of 8 ml of n-heptane and 2-propanol (9:1) and separated on a preparative HPLC column (250×20 mm; packed with Chiralcel OD; 20 μm). The eluent used is a mixture of n-heptane (LiChrosolv) and 2-propanol p.a. (98:2). A total of 20 injections of 0.4 ml in each case are carried out at a temperature of 40° C., a run time of 30 min and a flow rate of 7.0 ml/min (detection at 230 nm). 9 Fractions are obtained, which are differentiated according to analytical HPLC checking into a front (enantiomer I; retention: 6.13 min) and a back peak (enantiomer II; retention: 8.10 min) and isolated. The back fraction (retention: 8.10 min) is rechromatographed on the Chiracel OD column by means of n-heptane/2-propanol.

Yield of enantiomer I: 37 mg (45.1% of theory)

Yield of enantiomer II: 32 mg (39.6% of theory)

Analytical HPLC:

Column: 250×4.6 mm (Chiralcel OD-H; 5 μm)

Flow rate: 1.0 ml/min

Eluent: 98% n-heptane (LiChrosolv), 2% 2-propanol p.a.

Temperature: 40° C.

Loading volume: 10 μl
Detection: 220 nm

Example 6

8-Butyl -4-(4-fluorophenyl)-3-[fluoro-(4-trifluoromethyl-phenyl)-methyl]-2-isopropyl-5,6,7,8-tetrahydroquinolin-5-ol

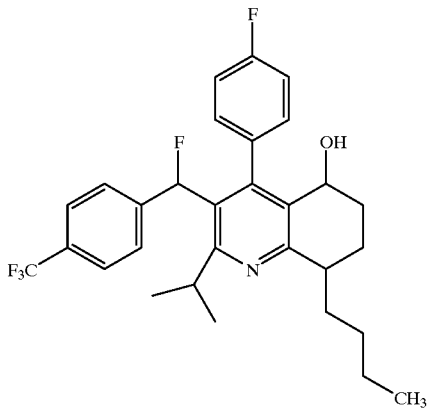

180 mg (0.28 mmol) of the compound from Example XII are stirred at room temperature for 16 hours in a solution of 16.8 ml of THF and 2.8 ml of 3 molar hydrochloric acid. The mixture is then stirred into 70 ml of saturated sodium hydrogen-carbonate solution and diluted with 20 ml of toluene. The organic phase is separated off, washed with water, dried over sodium sulphate, filtered and concentrated. The crude product is eluted on 25 g of silica gel 60 using cyclohexane/ethyl acetate 9:1.

Yield: 44 mg (30% of theory)
$R_f$=0.20 (Cy/EA 9:1)

Example 7

4-(4-Fluorophenyl)-3- [fluoro-(4-trifluoromethyl-phenyl)-methyl]-2-isopropyl-5,6,7,8-tetrahydroquinolin-5-one

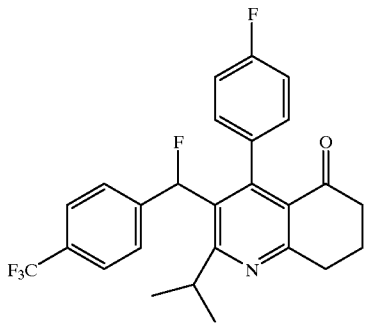

11.16 g (109.2 mmol) of neutral alumina and 23.54 g of pyridinium chlorochromate are stirred in portions with vigorous stirring into a solution of 16 g (36.4 mmol) of the compound from Example 2 in 655 ml of dichloromethane. After 1 hour, 140 g of silica gel 60 are added and the solid is filtered off with suction. The eluate is concentrated and dried.

Yield: 10.5 g (70% of theory)
$R_f$=0.55 (Cy/EA 6:4)

Example 8

4-(4-Fluorophenyl)-3-[fluoro-(4-trifluoromethyl-phenyl)-methyl]-2-isopropyl-6-(4-trifluoromethyl-phenyl)-methyl-5,6,7,8-tetrahydroquinolin-5-one

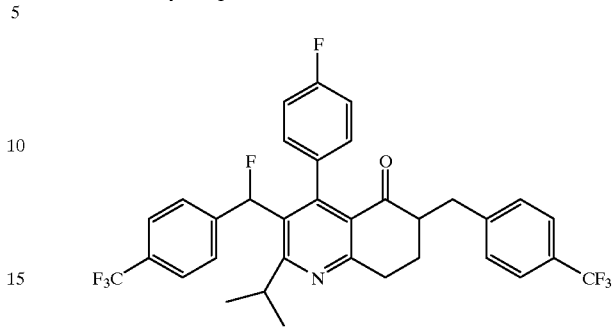

0.88 ml (1.4 mmol) of 1.6 molar n-butyllithium solution in n-hexane and 0.20 ml of diisopropylamine are stirred at −70° C. under argon into 4 ml of absolute THF and the mixture is stirred at −50° C. for 1 hour. A solution of the compound from Example 7 (460 mg, 1 mmol) is added dropwise to this solution at −50° C. and it is stirred for 1 hour further. Subsequently, a solution of 335 mg (1.4 mmol) of trifluoromethylbenzyl bromide in 1 ml of absolute THF is added dropwise and after 1 hour at −50° C. the mixture is hydrolysed with water. For working up, a mixture of 5% strength sodium chloride solution and toluene is stirred in, the phases are separated, the aqueous phase is reextracted and the combined organic phases are dried over sodium sulphate, filtered and concentrated. The crude product is eluted on 90 g of silica gel 60 using cyclohexane/ethyl acetate 9:1.

Yield: 443 mg (72% of theory)
$R_f$=0.23 (Cy/EA 9:1)

Example 9

4-(4-Fluorophenyl)-3-[fluoro-(4-trifluoromethyl-phenyl)-methyl]-2-isopropyl-6-(4-trifluoromethyl-phenyl)-methyl-5,6,7,8-tetrahydroquinolin-5-ol

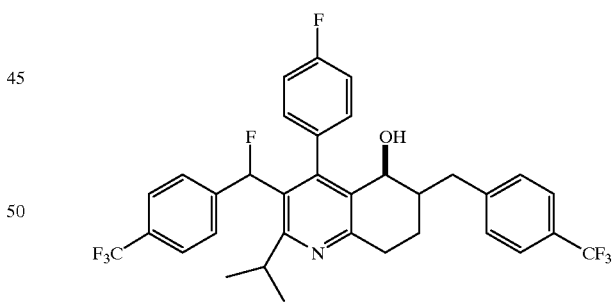

0.48 ml of a 1 molar diisobutylaluminium hydride solution (DIBAL-H) in toluene is added dropwise at −70° C. to a solution of 100 mg (0.32 mmol) of the compound from Example 8 in 1.6 ml of toluene. After 2 hours, the mixture is treated with 5 ml of 20% strength sodium potassium tartrate solution and stirred at room temperature for 0.5 hours. The organic phase is separated off, dried over sodium sulphate, filtered and concentrated. The crude product is eluted on silica gel 60 using cyclohexane/ethyl acetate 85:15.

Yield: 58 mg (59% of theory)
$R_f$=0.23 (Cy/EA 85:15)

| Ex. No. | Structure | Isomer | $R_f$ value |
|---|---|---|---|
| 10 | 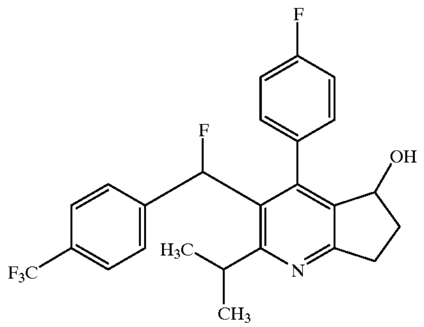 | diastereomer 1 | 0.28/Cy:EA (6:4) |
| 11 | 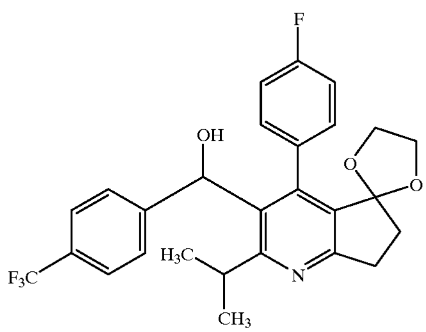 | | 0.33/Cy:EA (6:4) |
| 12 | 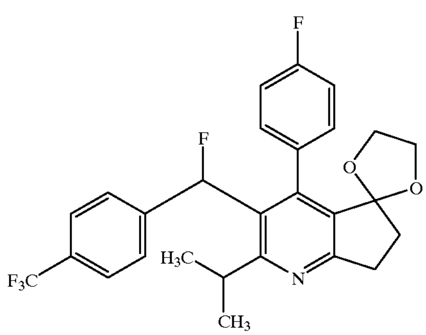 | | 0.48/Cy:EA (6:4) |
| 13 | 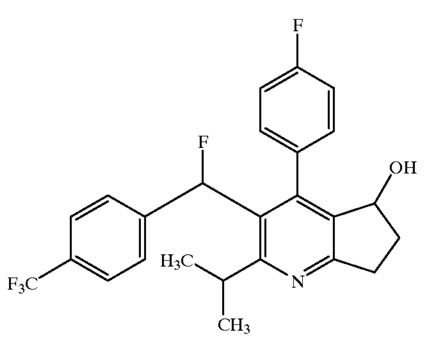 | diastereomer 2 | 0.27/Cy:EA (6:49) |

-continued

| Ex. No. | Structure | Isomer | $R_f$ value |
|---|---|---|---|
| 14 | 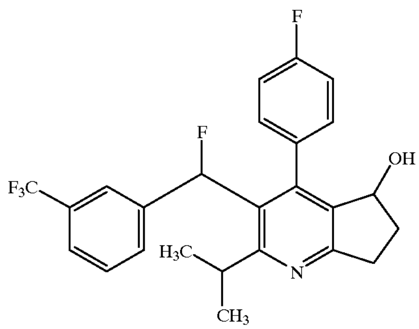 | diastereomer 1 | 0.29/Cy:EA (6:4) |
| 15 | 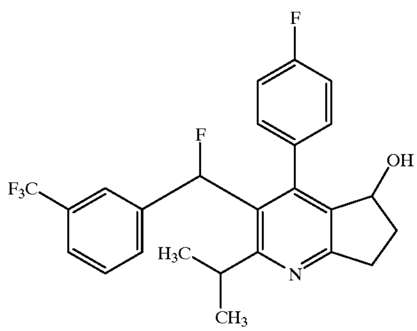 | diastereomer 2 | 0.23/Cy:EA (6:4) |
| 16 | 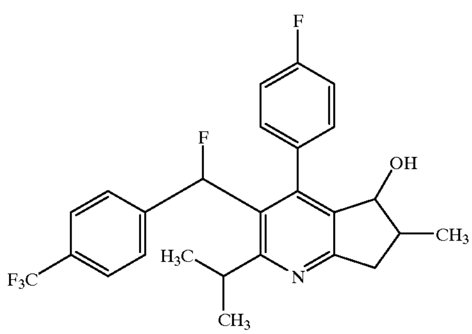 | | 0.18/Cy:EA (8:2) |
| 17 | 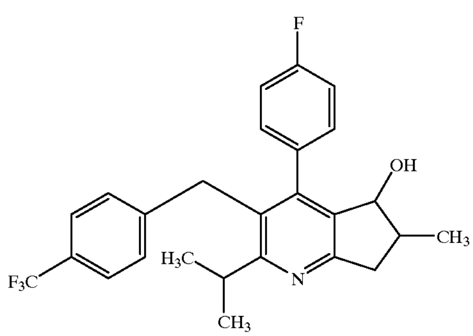 | | 0.12/Cy:EA (8:2) |

-continued

| Ex. No. | Structure | Isomer | $R_f$ value |
|---|---|---|---|
| 18 | 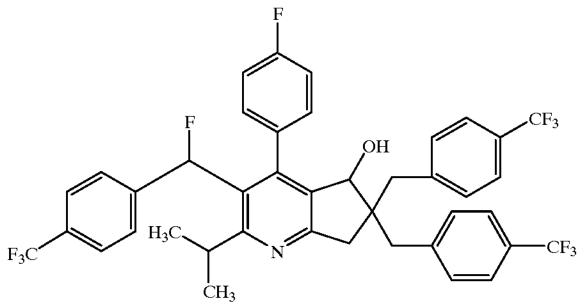 | | 0.23/Cy:EA (8:2) |
| 19 | 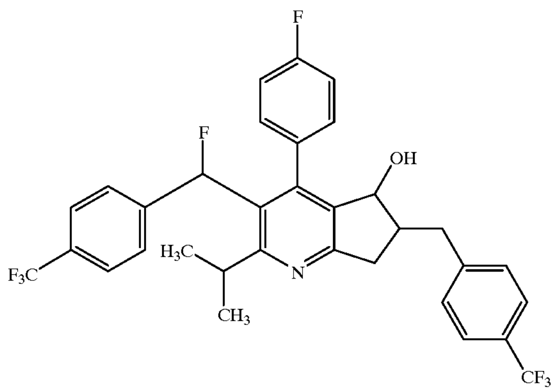 | | 0.12/Cy:EA (8:2) |
| 20 | 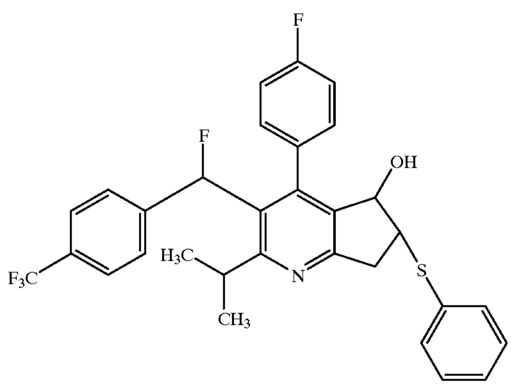 | diastereomer 1 | 0.27/Tol:EA (98:2) |
| 21 | 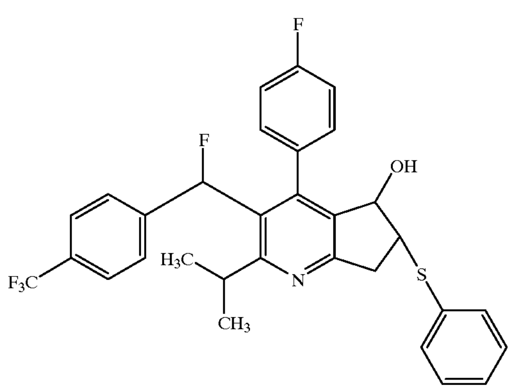 | diastereomer 2 + 1 63:37 | 0.23/Tol:EA (98:2) |

-continued

| Ex. No. | Structure | Isomer | R_f value |
|---|---|---|---|
| 22 | 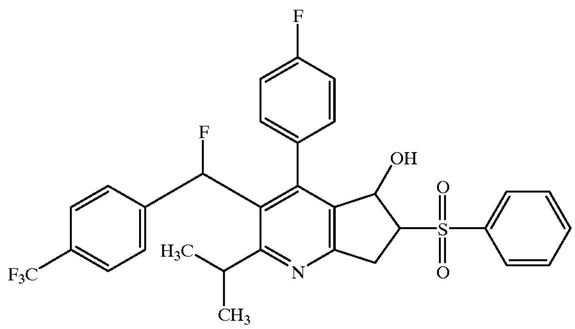 | | 0.13/Cy:EA (8:2) |
| 23 | 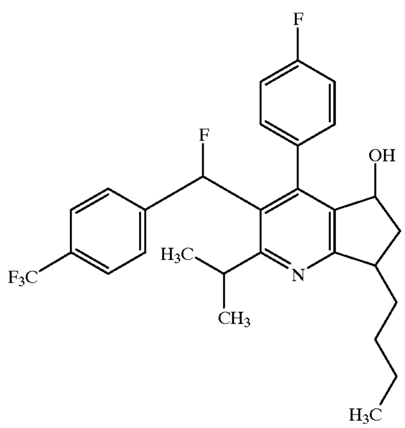 | | 0.11 + 0.18 Cy:EA (9:1) |
| 24 | 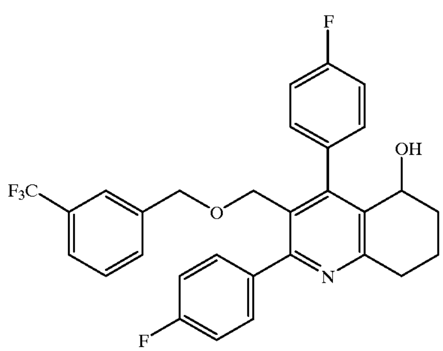 | | 0.19/PE:EA (7:3) |
| 25 | 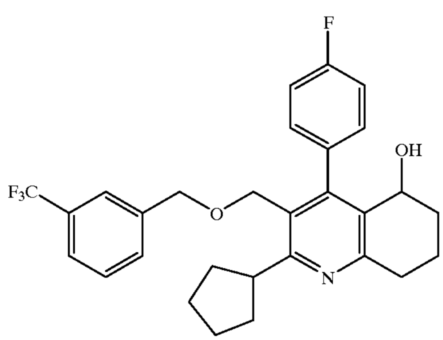 | | 0.22/PE:EA (8:2) |

-continued

| Ex. No. | Structure | Isomer | R_f value |
|---|---|---|---|
| 26 | 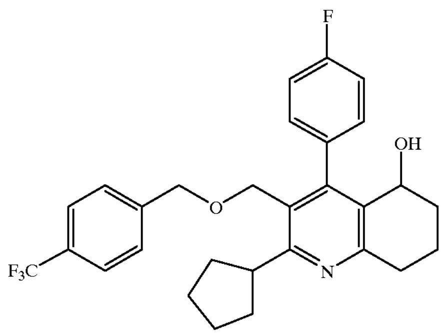 | | 0.22/PE:EA (8:2) |
| 27 | 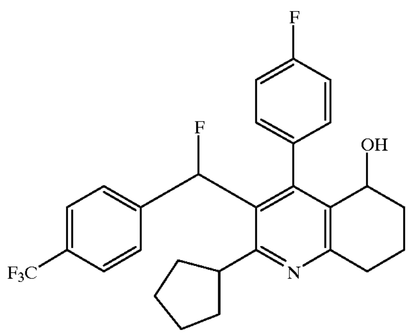 | Isomer I | 0.07 Cy:THF (9:1) |
| 28 | 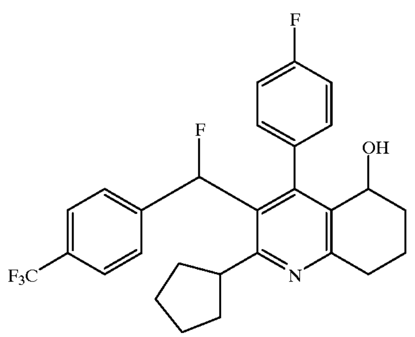 | Isomer II | 0.44 Cy:THF (8:2) |
| 29 | 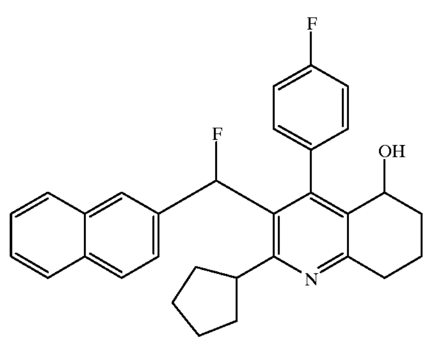 | Isomer I | 0.31 Cy:THF (8:2) |

-continued

| Ex. No. | Structure | Isomer | R$_f$ value |
|---|---|---|---|
| 30 | 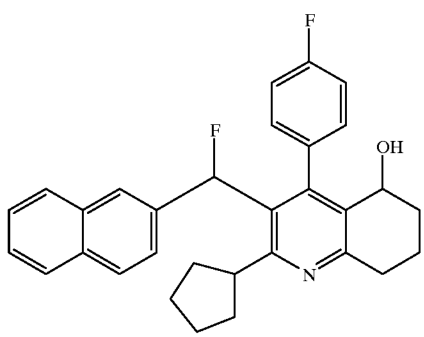 | Isomer II | 0.39 Cy:THF (8:2) |
| 31 | 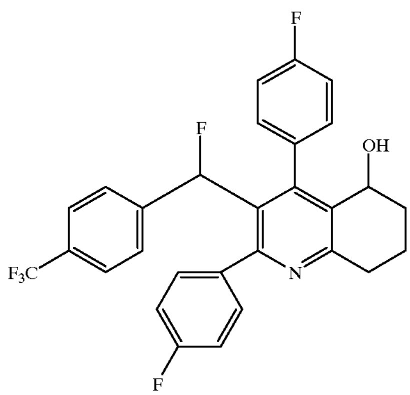 | Isomer I | 0.13 Cy:THF (8:2) |
| 32 | 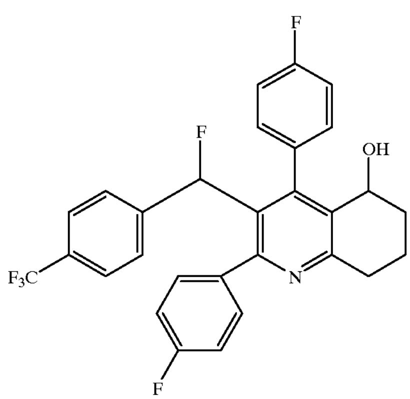 | Isomer II | 0.21 Cy:THF (8:2) |
| 33 | 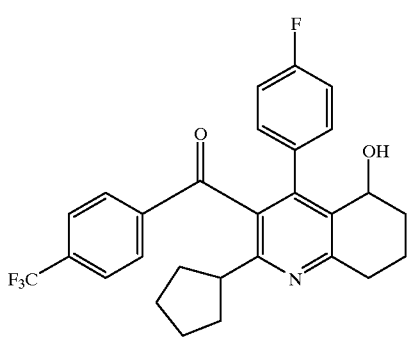 | Isomer I | 0.16 Cy:THF (9:1) |

-continued

| Ex. No. | Structure | Isomer | R_f value |
|---|---|---|---|
| 34 | 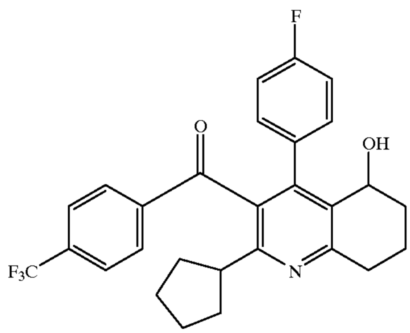 | Isomer II | 0.21 Cy:THF (9:1) |
| 35 | 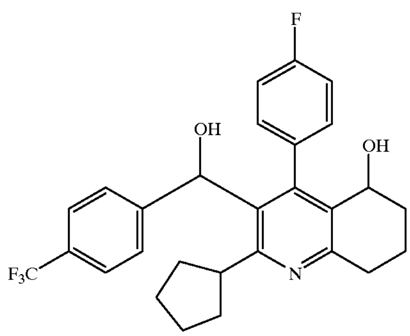 | Isomer I | 0.2 Cy:THF (8:2) |
| 36 | 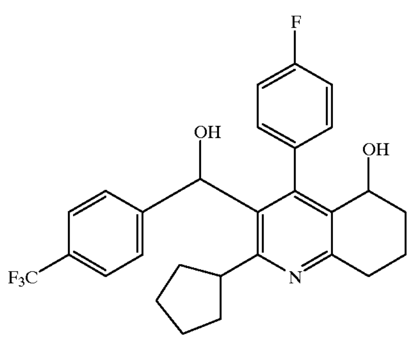 | Isomer II | 0.33 Cy:THF (8:2) |
| 37 | 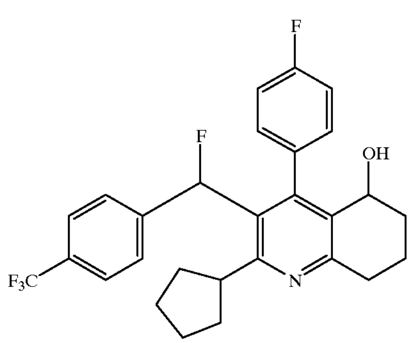 | Isomer I from Ex. No. 28 | chiralcel 250 × 2:8.29 (n-heptane/1% EtOH) |

-continued

| Ex. No. | Structure | Isomer | R_f value |
|---|---|---|---|
| 38 | 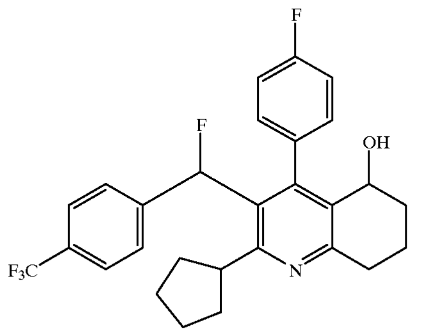 | Isomer II from Ex. No. 28 | chiralcel 250 × 2:10.98 (n-heptane/1% EtOH) |
| 39 | 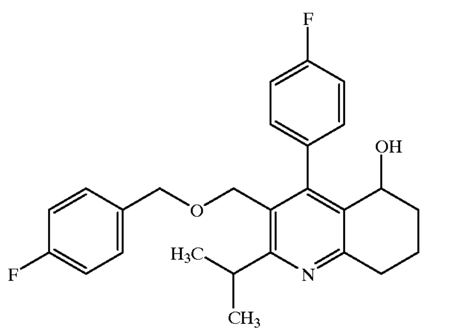 | | 0.18 PE:EA (8:2) |
| 40 | 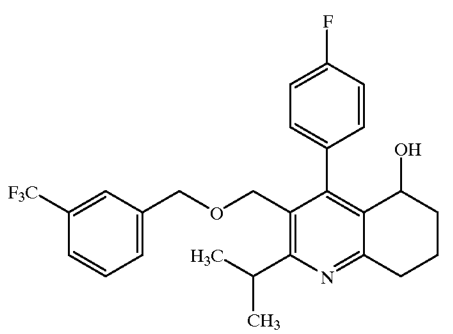 | | 0.2 PE:EA (8:2) |
| 41 | 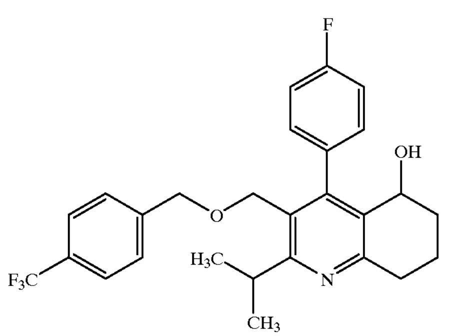 | | 0.19 PE:EA (8.2) |

-continued

| Ex. No. | Structure | Isomer | $R_f$ value |
|---|---|---|---|
| 42 | (structure: 4-(4-fluorophenyl)-3-[chloro(4-trifluoromethylphenyl)methyl]-2-isopropyl-5,6,7,8-tetrahydroquinolin-5-ol) | Isomer II | 0.45 Cy:THF (8:2) |
| 43 | (structure: 4-(4-fluorophenyl)-3-[fluoro(4-trifluoromethylphenyl)methyl]-2-cyclopentyl-5,6,7,8-tetrahydroquinolin-5-ol) | Isomer Ia from Ex. No. 27 | chiralcel 250 × 2:7.88 (n-heptane/1% EtOH) |
| 44 | (structure: 4-(4-fluorophenyl)-3-[fluoro(4-trifluoromethylphenyl)methyl]-2-cyclopentyl-5,6,7,8-tetrahydroquinolin-5-ol) | Isomer Ib from Ex. No. 27 | chiralcel 250 × 2:12.0 (n-heptane/1% EtOH) |
| 45 | (structure: 4-(4-fluorophenyl)-3-[chloro(4-trifluoromethylphenyl)methyl]-2-isopropyl-5,6,7,8-tetrahydroquinolin-5-ol) | Isomer I/ II-mixture | 0.45/0.38 Cy/THF (8:2) |

-continued

| Ex. No. | Structure | Isomer | R_f value |
|---|---|---|---|
| 46 | 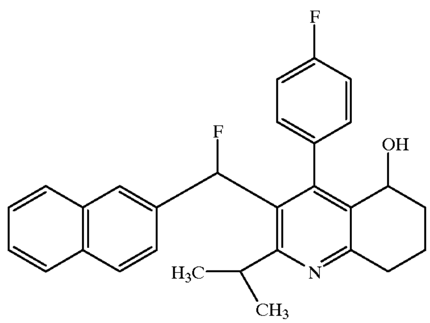 | Isomer I | 0.22 Cy:THF (8:2) |
| 47 | 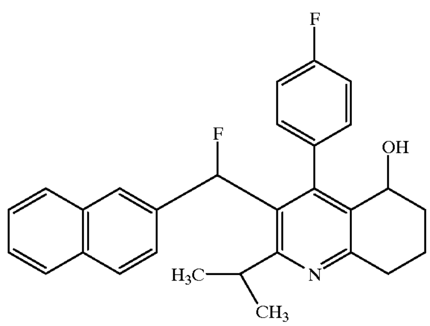 | Isomer II | 0.18 Cy:THF (8:2) |
| 48 | 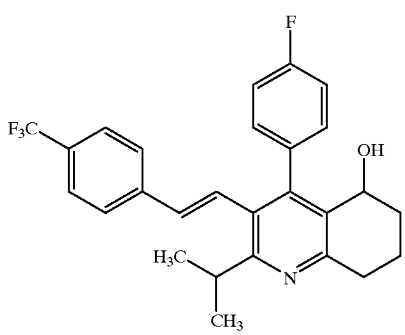 | | 0.20 Tol:EA (9:1) |
| 49 | 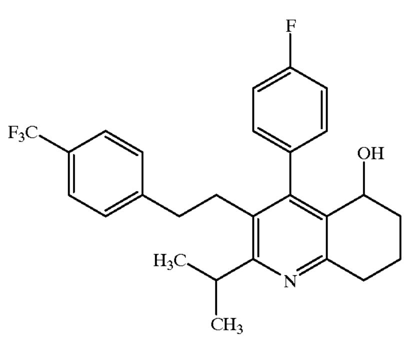 | | 0.43 Cy:EA (8:2) |

| Ex. No. | Structure | Isomer | $R_f$ value |
|---|---|---|---|
| 50 | 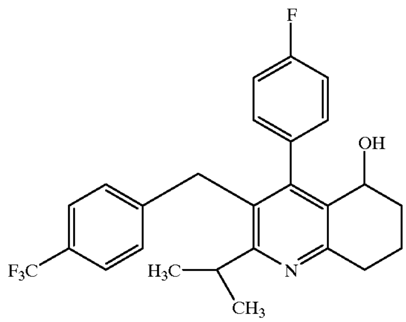 | | 0.34<br>Tol:EE (9:1) |
| 51 | 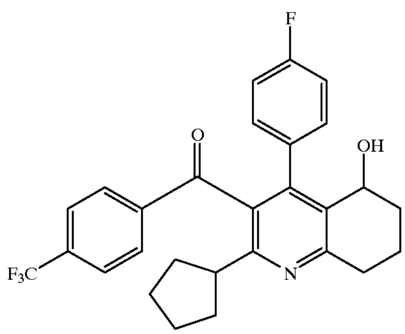 | Isomer 1 from<br>Ex. No. 33 | chiralpak AD<br>250 × 4.6:7.29<br>(n-heptane/2-Propanol =<br>95:5) |
| 52 | 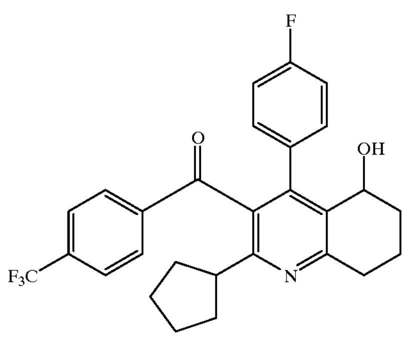 | Isomer II from<br>Ex. No. 33 | chiralpak AD<br>250 × 4.6:9.77<br>(n-heptane/2-Propanol =<br>95:5) |
| 53 | 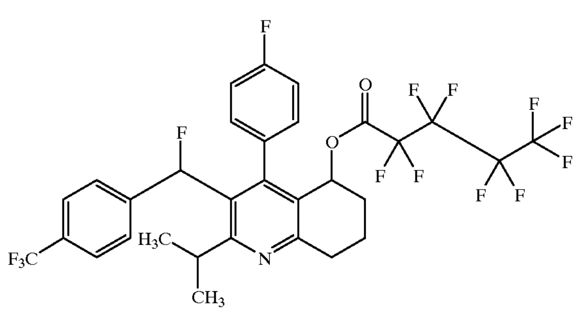 | | 0.18<br>PE:EA<br>(6:1) |

-continued

| Ex. No. | Structure | Isomer | R$_f$ value |
|---|---|---|---|
| 54 | 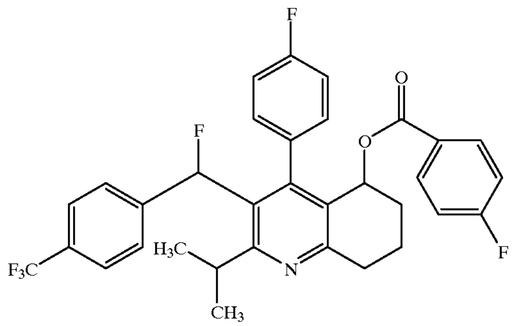 | diastereomer 1 | 0.26 Cy:EA (18:1) |
| 55 | 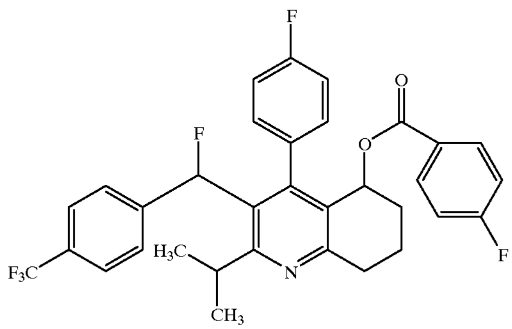 | diastereomer 2 | 0.13 Cy:EA (18:1) |
| 56 | 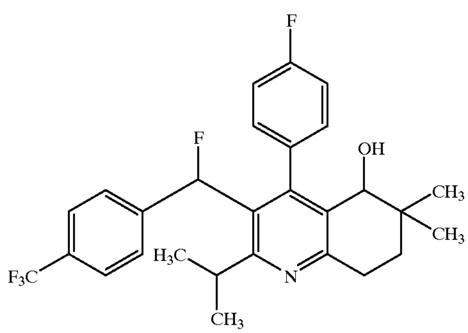 | Isomer mixture (4 isomers) | 0.39 Tol:EA (9:1) |
| 57 | 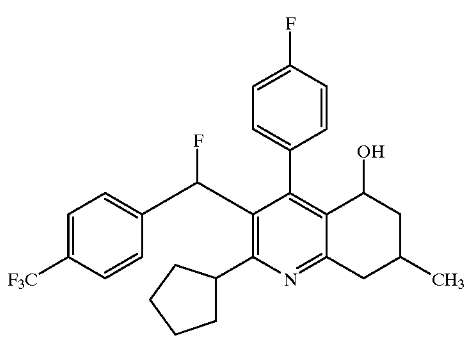 | Isomer mixture (8 isomers) | 0.38 Tol:EA (9:1) |

-continued

| Ex. No. | Structure | Isomer | R_f value |
|---|---|---|---|
| 58 | 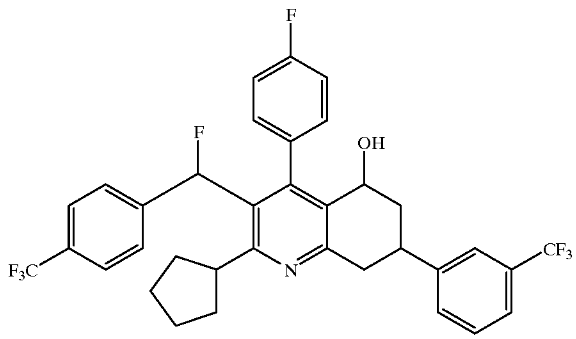 | diastereomer 1 | 0.41 PE:EA (4:1) |
| 59 | 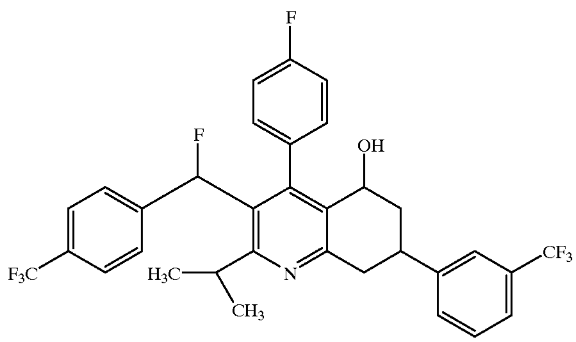 | diastereomer 2 | 0.50 PE:EA (4:19) |
| 60 | 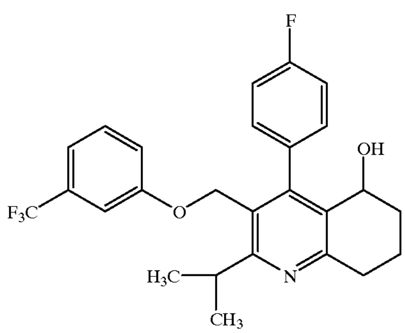 | | 0.166 PE:EA (8:2) |
| 61 | 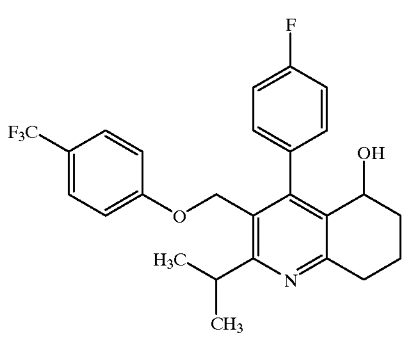 | | 0.15 PE:EA (8:2) |

-continued

| Ex. No. | Structure | Isomer | $R_f$ value |
|---|---|---|---|
| 62 | (structure) | Isomer II | 0.42 Tol:EA (9:1) |
| 63 | (structure) | Isomer I | 0.58 Tol:EA (9:1) |
| 64 | (structure) | Isomer Ia | 0.47 Tol:EA (9:1) |
| 65 | (structure) | Isomer mixture | 0.44 Tol:EA (9:1) |

-continued

| Ex. No. | Structure | Isomer | $R_f$ value |
|---|---|---|---|
| 66 | 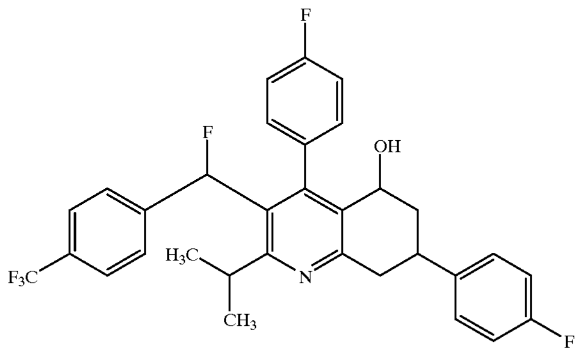 | Isomer IIa | 0.37 Tol:EA (9:1) |
| 67 | 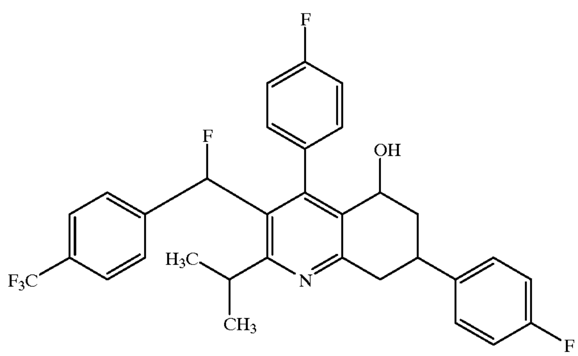 | Isomer mixture | 0.51 Tol:EA (9:1) |
| 68 | 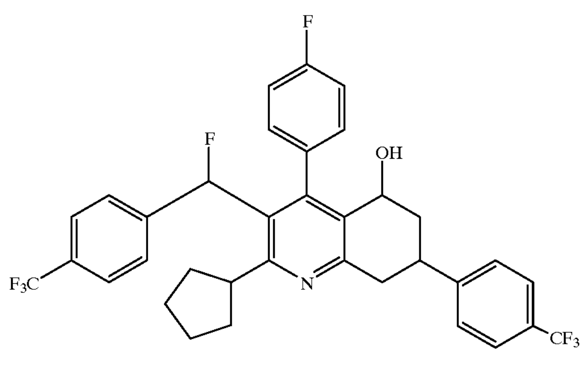 | Isomer I | 0.52 Toluene |
| 69 | 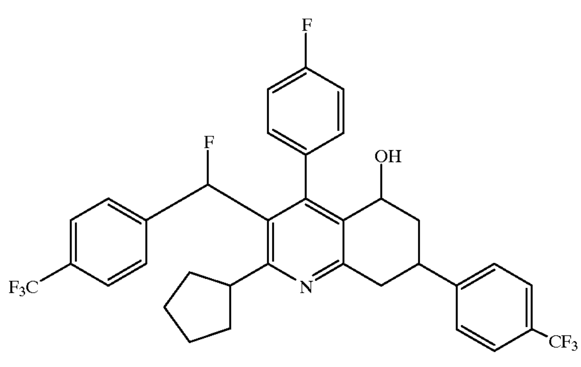 | Isomer II | 0.38 Toluene |

-continued

| Ex. No. | Structure | Isomer | $R_f$ value |
|---|---|---|---|
| 70 | 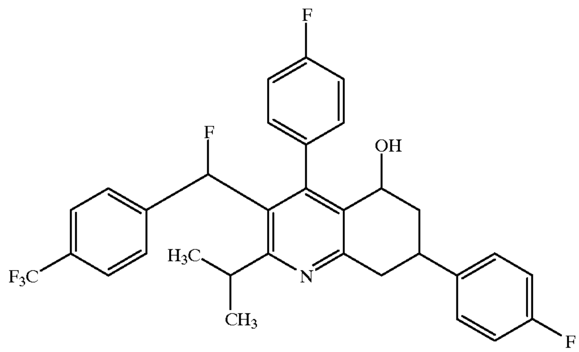 | Isomer Ib | 0.42 Tol:EA (9:1) |
| 71 | 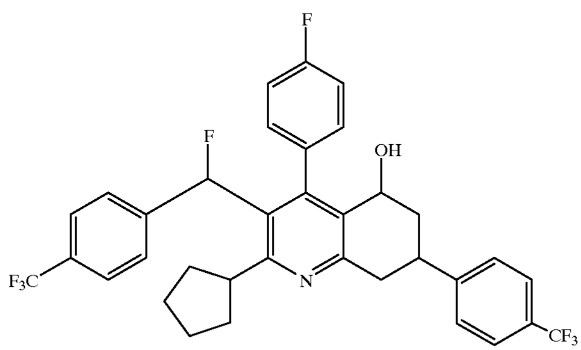 | Mixture from 8 isomers | 0.47 and 0.53 Toluene |
| 72 | 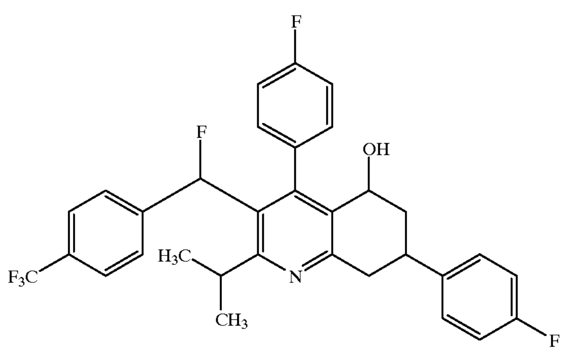 | Isomer IIb | 0.42 Tol:EA (9:1) |
| 73 | 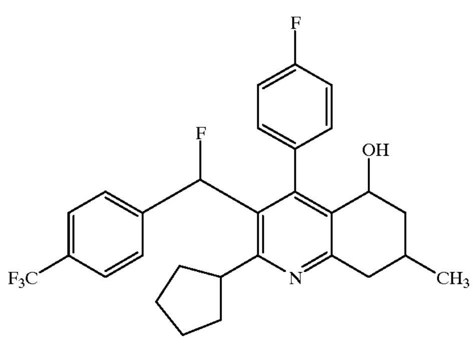 | Isomer I | 0.41 Tol:EA (9:1) |

-continued

| Ex. No. | Structure | Isomer | R_f value |
|---|---|---|---|
| 74 | 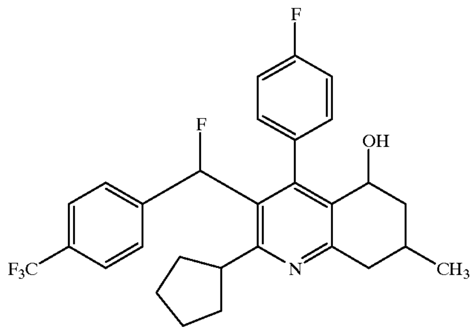 | Isomer II | 0.34 Tol:EA (9:1) |
| 75 | 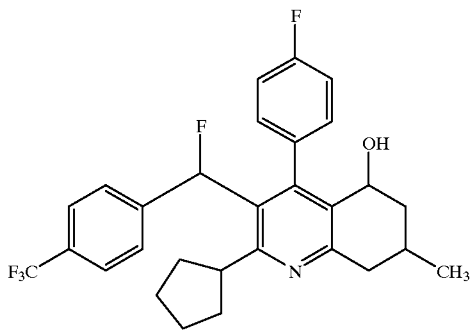 | Isomer III | 0.52 Tol:EA (9:1) |
| 76 | 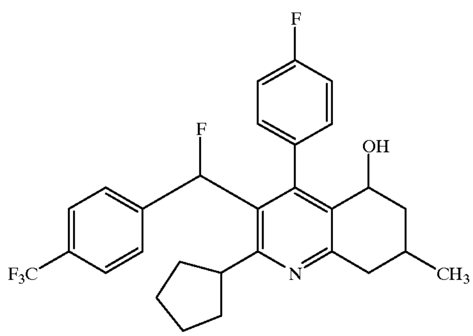 | Isomer IV | 0.54 Tol:EA (9:1) |
| 77 | 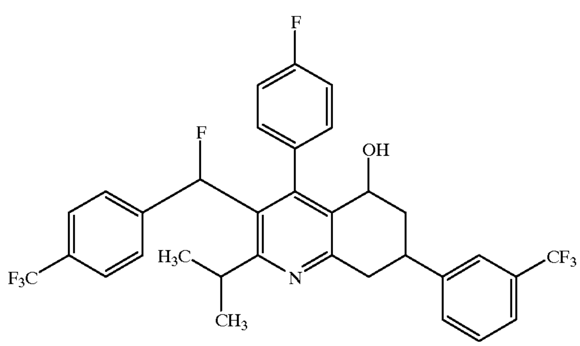 | | 0.2 PE:EA (6:1) |

-continued

| Ex. No. | Structure | Isomer | $R_f$ value |
|---|---|---|---|
| 78 | 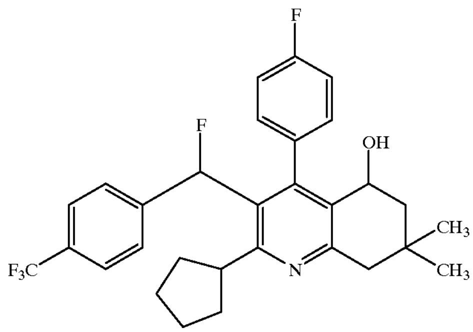 | Isomer I | 0.6 Tol:EA (9:1) |
| 79 | 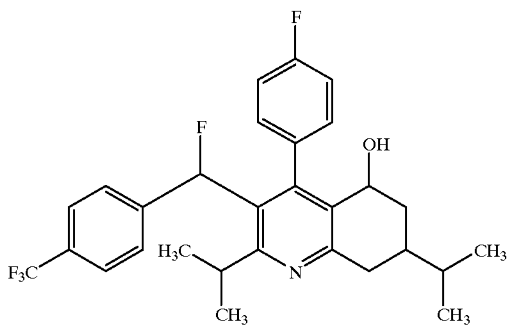 | Isomer mixture | 0.59 Cy:THF (8:2)) |
| 80 | 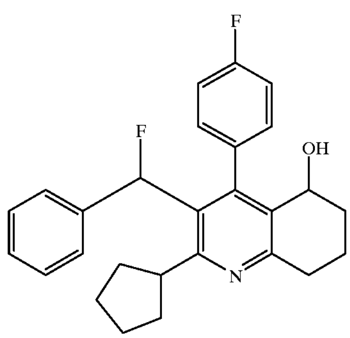 | Isomer I | 0.18 Cy:THF (9:1) |
| 81 | 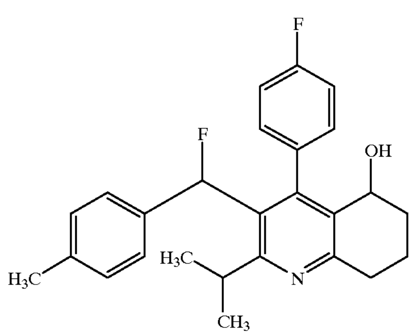 | Isomer I | 0.29 EA:PE (1:5) |

-continued

| Ex. No. | Structure | Isomer | R$_f$ value |
|---|---|---|---|
| 82 | 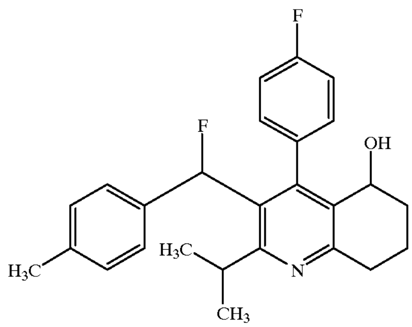 | Isomer II | 0.29 EA:PE (1:5) |
| 83 | 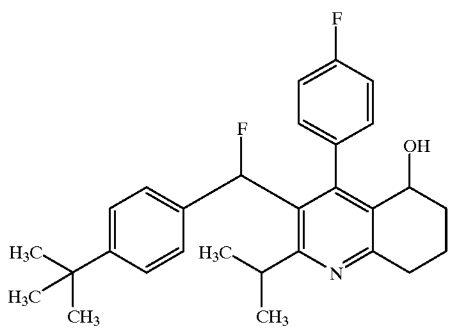 | Isomer I | 0.38 EA:PE (1:5) |
| 84 | 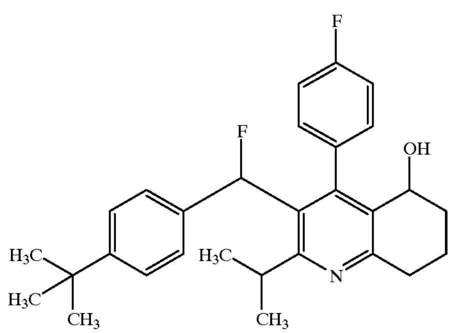 | Isomer II | 0.38 EA:PE (1:5) |
| 85 | 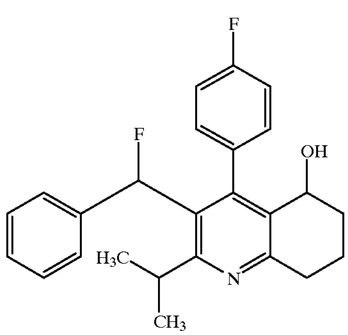 | Isomer I | 0.25 EA:PE (1:5) |

-continued

| Ex. No. | Structure | Isomer | R_f value |
|---|---|---|---|
| 86 | 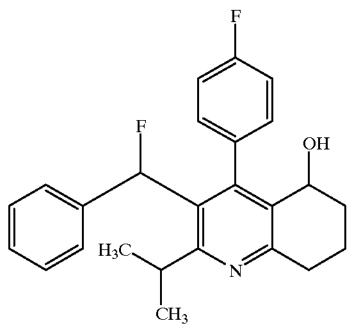 | Isomer II | 0.25<br>EA:PE<br>(1:5) |
| 87 | 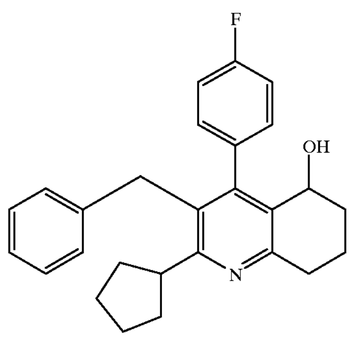 | Isomer II | 0.29<br>Cy:EA<br>(5:1) |
| 88 | 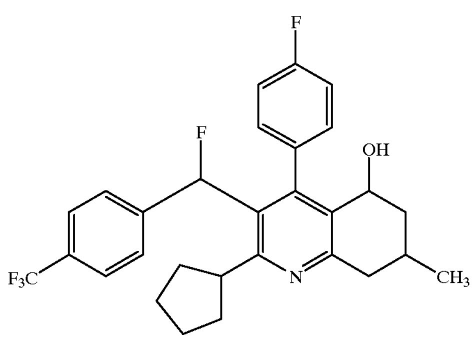 | Isomer IVb | Chiralpak AD<br>10 μm: 12.34<br>(97% n-Heptane/Ethanol = 97:3) |
| 89 | 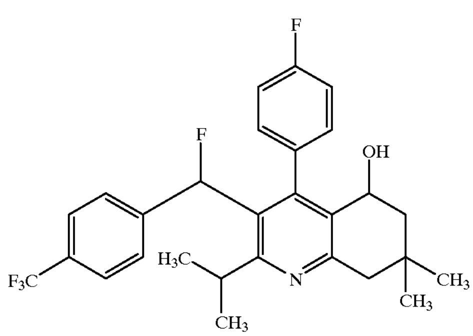 | Isomer I | 0.55<br>Tol:EA<br>(9:1) |

-continued

| Ex. No. | Structure | Isomer | R$_f$ value |
|---------|-----------|--------|-------------|
| 90 | 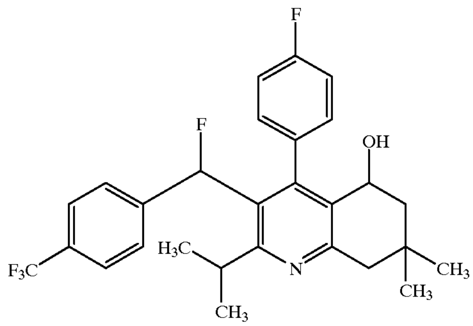 | Isomer II | 0.55<br>Tol:EA<br>(9:1) |
| 91 | 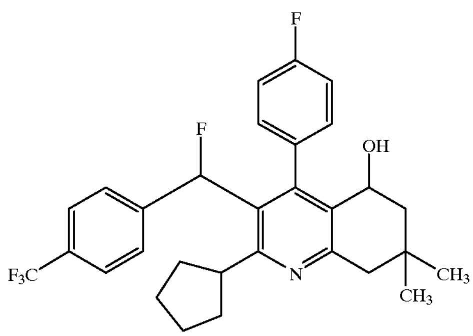 | Isomer II | 0.33<br>Cy:THF<br>(9:1) |
| 92 | 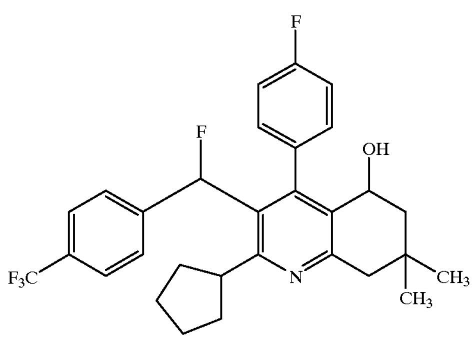 | Isomer I | 0.60<br>Cy:THF<br>(9:1) |
| 93 | 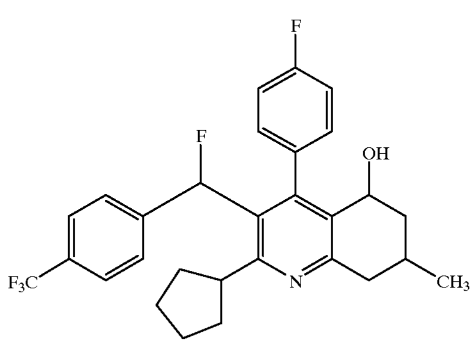 | Isomer IIIa | Gromchiral AD<br>10 μm: 6.33<br>n-Heptane:2-Propanol<br>(98:2) |

-continued

| Ex. No. | Structure | Isomer | R_f value |
|---|---|---|---|
| 94 | 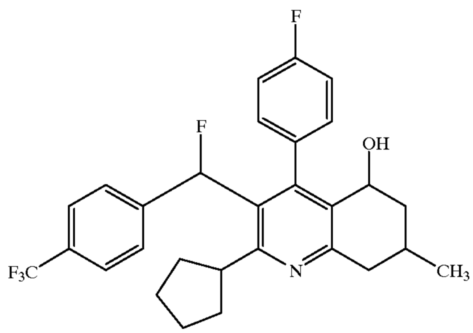 | Isomer IIIb | Gromchiral AD 10 μm: 6.33 n-Heptane:2-Propanol (98:2) |
| 95 | 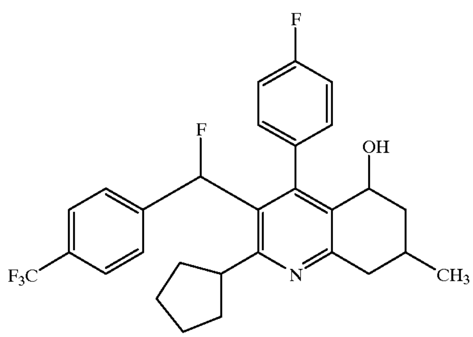 | Isomer Ia | Gromchiral AD 10 μm: 10.49 n-Heptane:2-Propanol (98:2) |
| 96 | 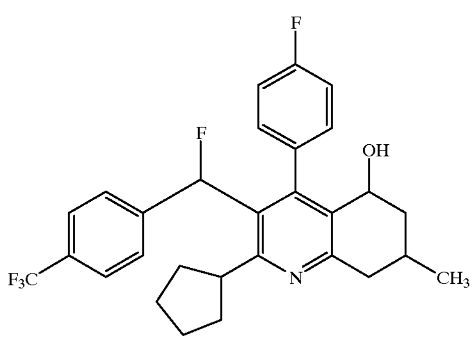 | Isomer Ib | Gromchiral AD 10 μm: 6.02 n-Heptane:2-Propanol (98:2) |
| 97 | 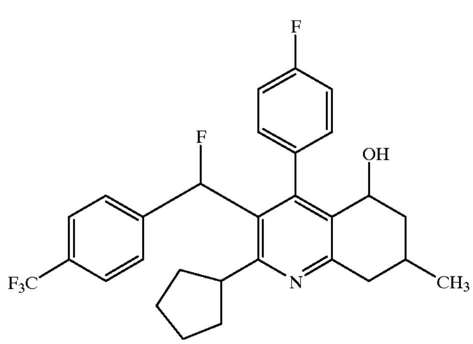 | Isomer IVa | chiralpak AD 10 μm: 10.35 n-Heptane:EtOH (97:3) |

-continued

| Ex. No. | Structure | Isomer | $R_f$ value |
|---|---|---|---|
| 98 | 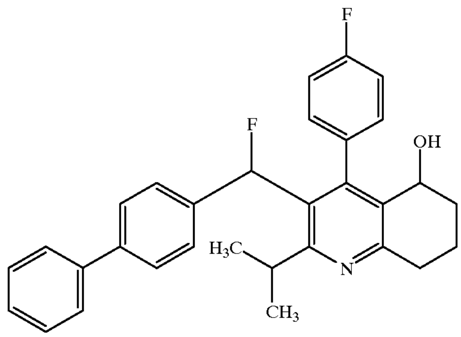 | Isomer I | 0.25 Cy:EA (5:1) |
| 99 | 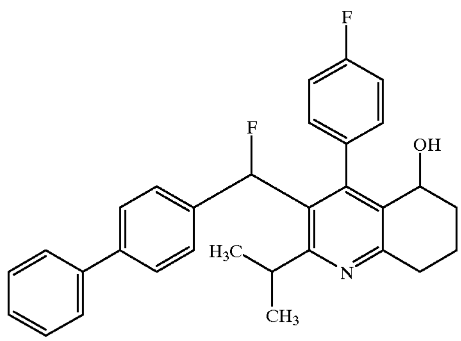 | Isomer II | 0.23 Cy:EA (5:1) |
| 100 | 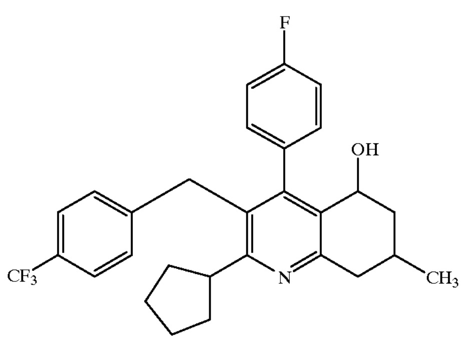 | from Ex. No. 73 | 0.43 Tol:EA (9:1) |
| 101 | 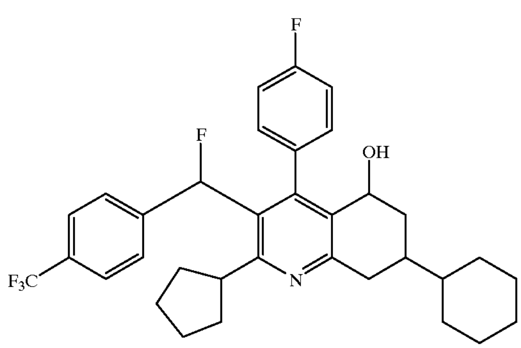 | Isomer I | 0.58 Tol/EA (9:1) |

-continued

| Ex. No. | Structure | Isomer | $R_f$ value |
|---|---|---|---|
| 102 | 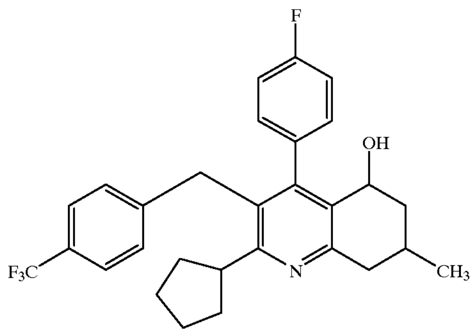 | from Ex. No. 76 | 0.36<br>Tol. EA<br>(9:1) |
| 103 | 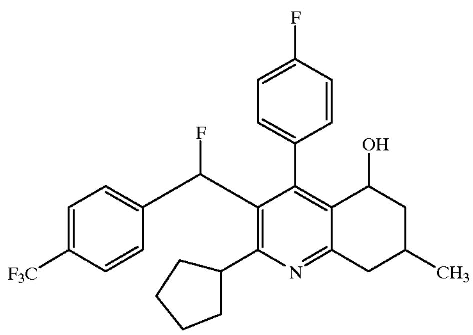 | Isomer IIa<br>from Ex. No. 74 | Daicel chiralpak<br>AD 10 μm: 8.86<br>n-Heptane:2-Propanol<br>(97:3) |
| 104 | 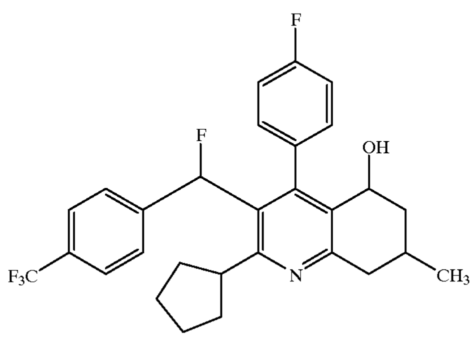 | Isomer IIb<br>from Ex. No. 74 | Daicel chiralpak<br>AD 10 μm: 11.54<br>n-Heptane:2-Propanol<br>(97:3) |
| 105 | 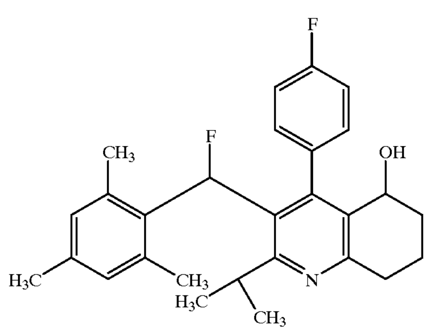 | Isomer I + II | 0.38/0.40<br>Cy:EA<br>(5:1) |

-continued

| Ex. No. | Structure | Isomer | R$_f$ value |
|---|---|---|---|
| 106 | 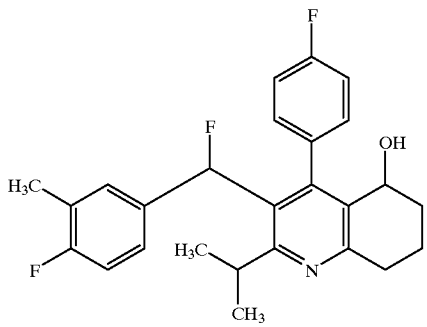 | Isomer I | 0.27<br>Cy:EA<br>(5:1) |
| 107 | 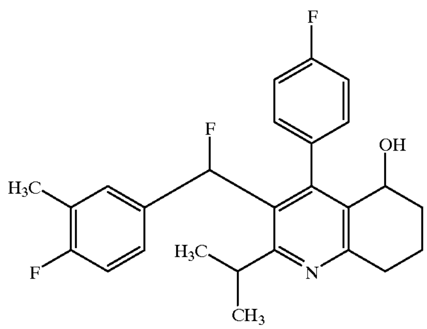 | Isomer II | 0.22<br>Cy:EA<br>(5:1) |
| 108 | 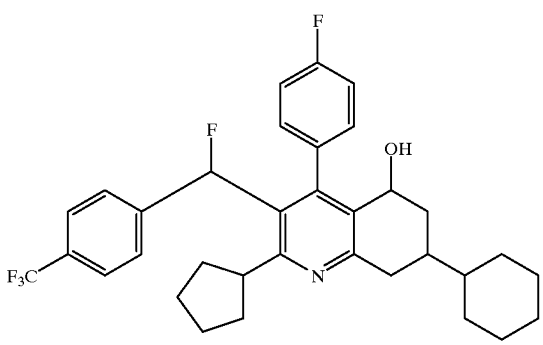 | Isomer IIa | 0.16<br>Toluol |
| 109 | 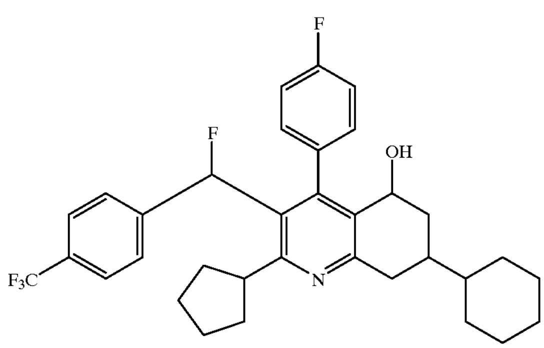 | Isomer III | 0.44<br>Toluol |

-continued

| Ex. No. | Structure | Isomer | R_f value |
|---|---|---|---|
| 110 | 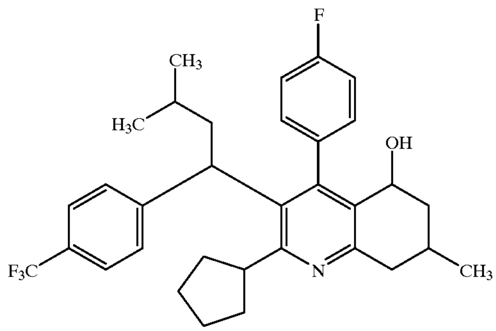 | Isomer I from Ex. No. 74 | 0.54 Tol:EA (9:1) |
| 111 | 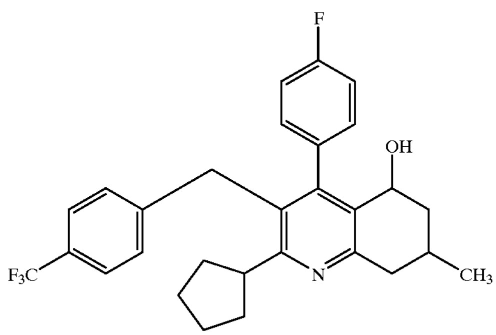 | Isomer II from Ex. No. 74 | 0.48 Tol:EA (9:1) |
| 112 | 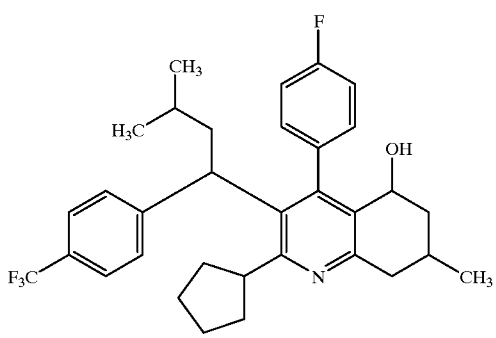 | Isomer IV from Ex. No. 76 | 0.47 Tol:EA (9:1) |
| 113 | 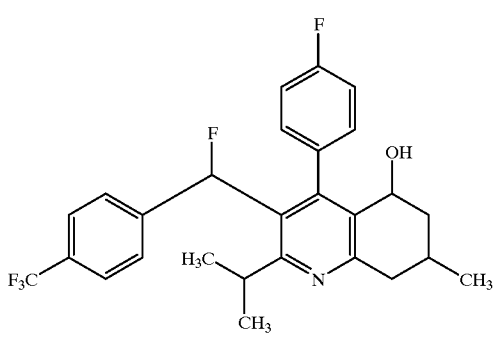 | Isomer I | 0.38 Tol:EA (9:1) |

-continued

| Ex. No. | Structure | Isomer | R_f value |
|---|---|---|---|
| 114 | 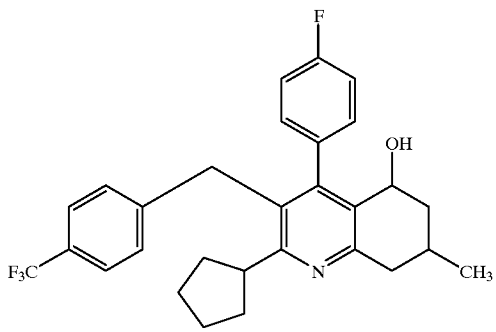 | Isomer II from Ex. No. 75 | 0.33 Tol:EA (9:1) |
| 115 | 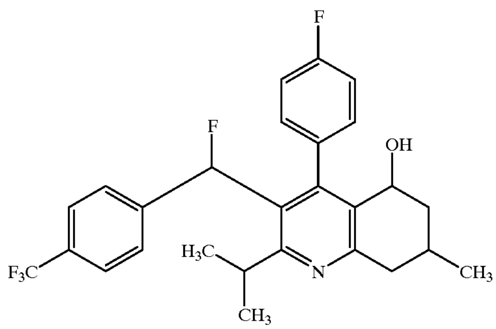 | Isomer II | 0.48 Tol:EA (9:1) |
| 116 | 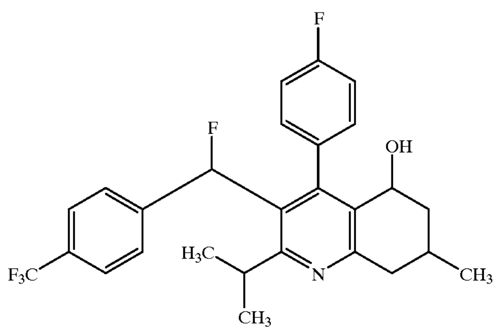 | Isomer III | 0.5 Tol EA (9:1) |
| 117 | 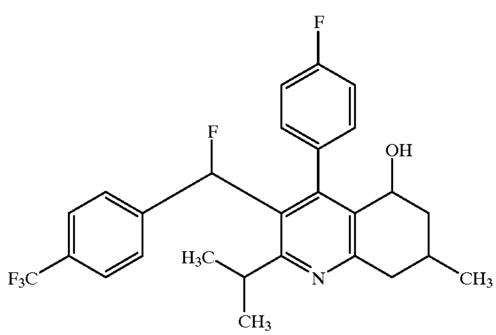 | Isomer IV | 0.5 Tol:EA (9:1) |

-continued

| Ex. No. | Structure | Isomer | $R_f$ value |
|---|---|---|---|
| 118 | 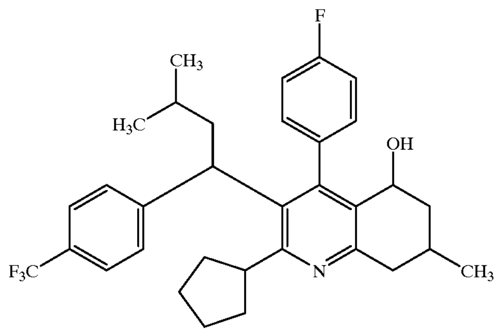 | Isomer II from Ex. No. 74 | 0.54 Tol:EA (9:1) |
| 119 | 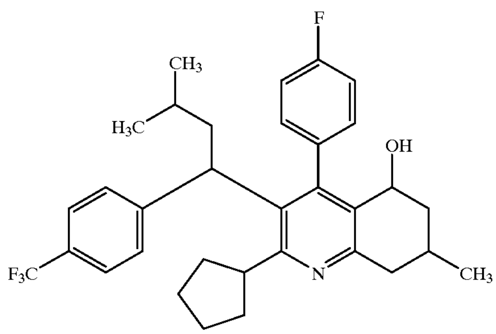 | Isomer mixture from Ex. No. 75 | 0.452/0.428 Tol:EA (9:1) |
| 120 | 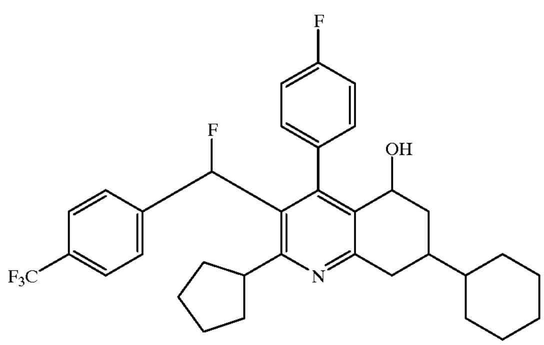 | Isomer IIb | 0.13 Toluol |
| 121 | 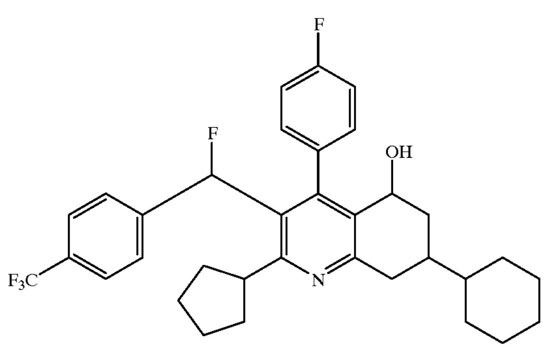 | Isomer IV | 0.13 Toluol |

-continued

| Ex. No. | Structure | Isomer | R_f value |
|---|---|---|---|
| 122 | 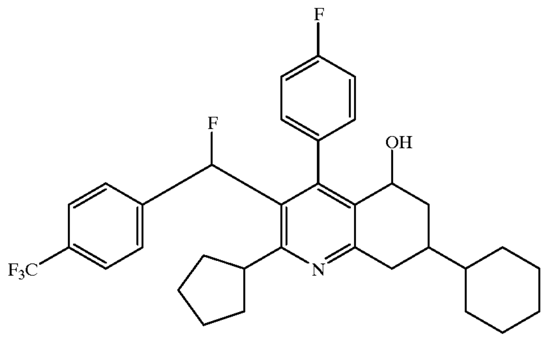 | Isomer III | 0.38 Toluol |
| 123 | 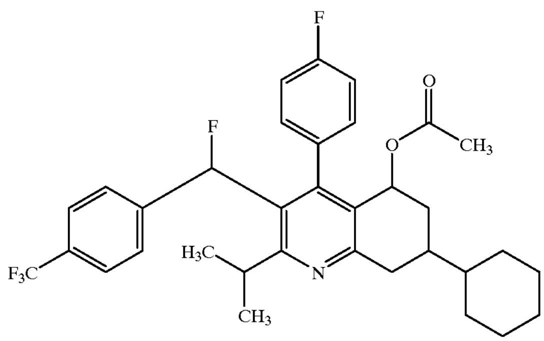 | diastereomer 2 | 0.42 Cy:EA (8:2) |
| 124 | 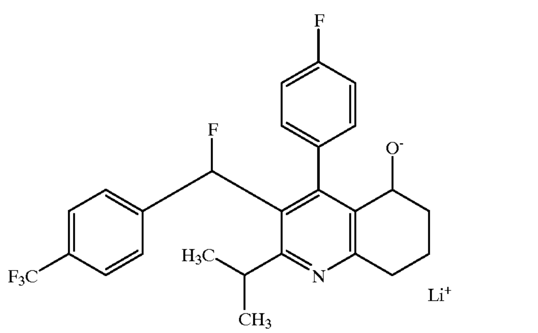 | diastereomer 2 | |
| 125 | 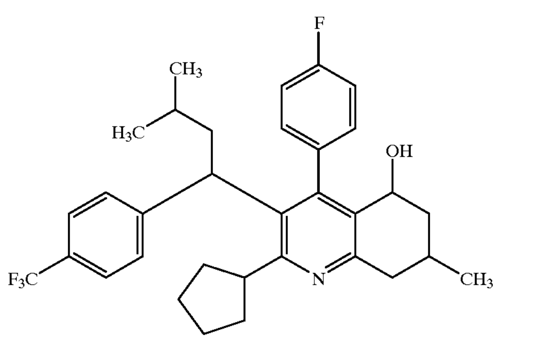 | Isomer I from Ex. No. 75 | 0.46 Tol:EA (9:1) |

-continued

| Ex. No. | Structure | Isomer | $R_f$ value |
|---|---|---|---|
| 126 | 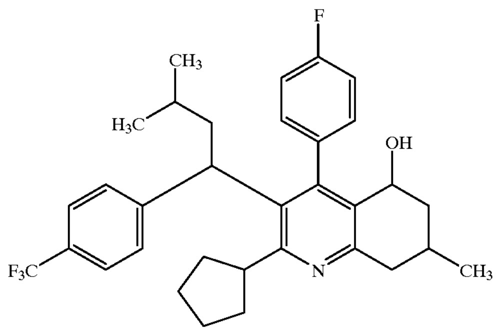 | Isomer II from Ex. No. 75 | 0.33 Tol:EA (9:1) |
| 127 | 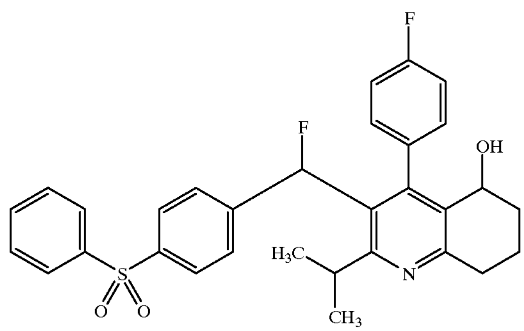 | Isomer I | 0.08 Cy:EA (5:1) |
| 128 | 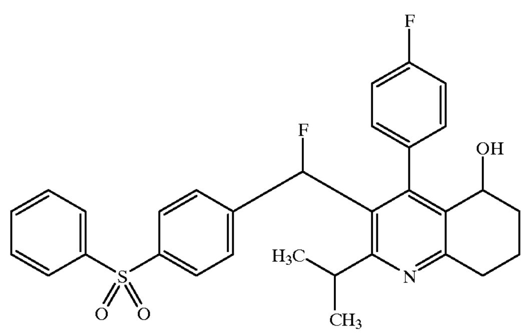 | Isomer II | 0.24 Cy:EA (2:1) |
| 129 | 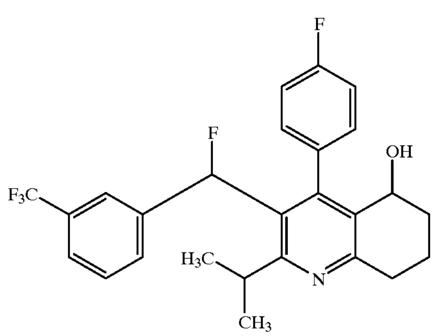 | Isomer I | 0.53 Cy:EA (2:1) |

-continued

| Ex. No. | Structure | Isomer | $R_f$ value |
|---|---|---|---|
| 130 | 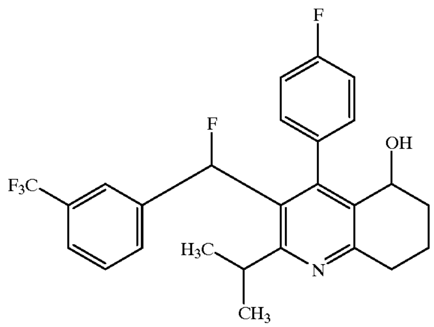 | Isomer II | 0.50 Cy:EA (2:1) |
| 131 | 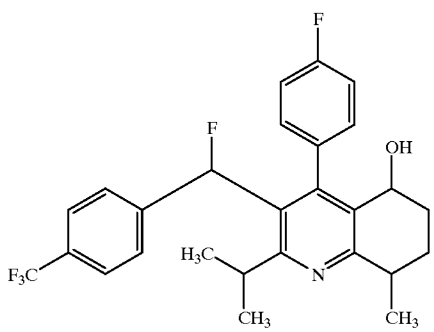 | diastereomer 2 | 0.16 Cy:EA (9:1) |
| 132 | 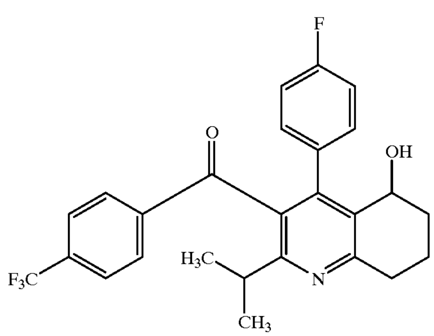 | | 0.14 Cy:EA (2:1) |
| 133 | 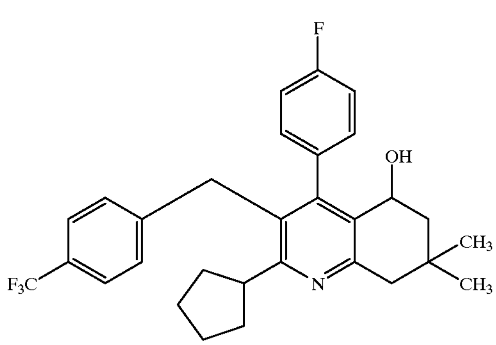 | from Isomer II (Ex. No. 91) | 0.4 Tol:EA (9.5:0.5) |

-continued

| Ex. No. | Structure | Isomer | $R_f$ value |
|---|---|---|---|
| 134 | 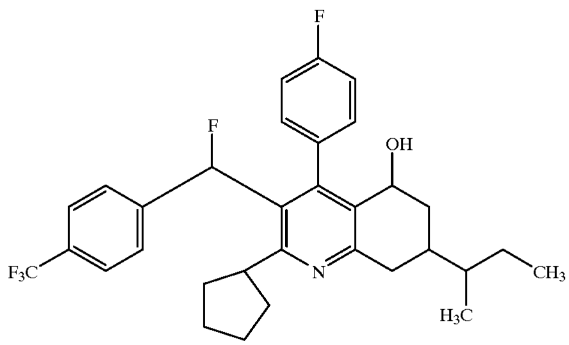 | Isomer I | 0.78 Toluene |
| 135 | 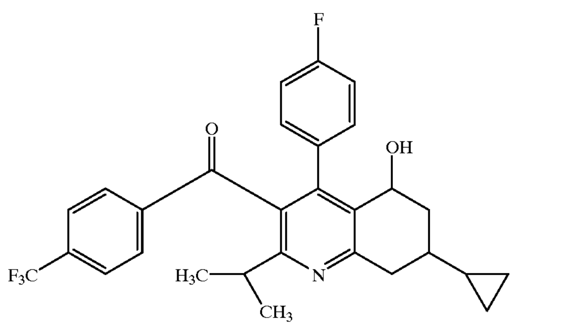 | Isomer I | 0.32 Toluene |
| 136 | 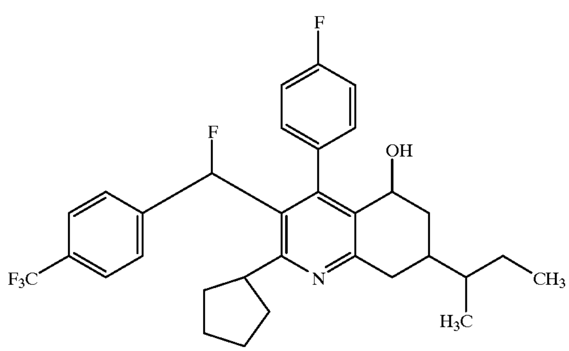 | Isomer II | 0.63 Toluene |
| 137 | 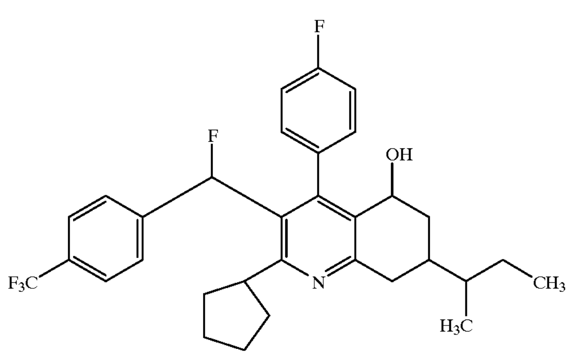 | Isomer mixture | 0.66/0.76 Toluene |

-continued

| Ex. No. | Structure | Isomer | R_f value |
|---|---|---|---|
| 138 | 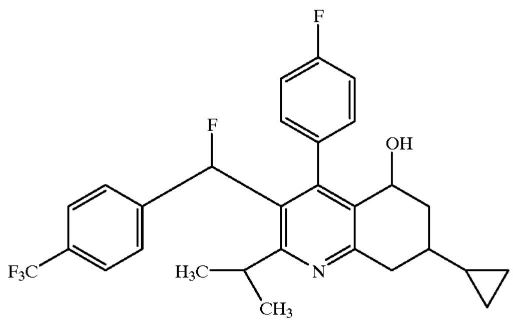 | Isomer II | 0.29 Toluene |
| 139 | 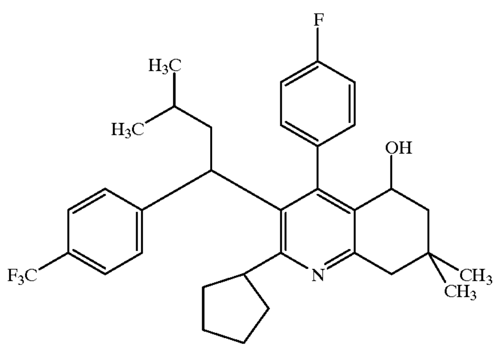 | corresponds to No. 133 | 0.48 Tol:EA (9.5:0.5) |
| 140 | 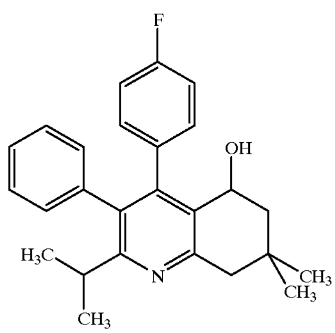 | | 0.49 Cy:EA (5:1) |
| 141 | 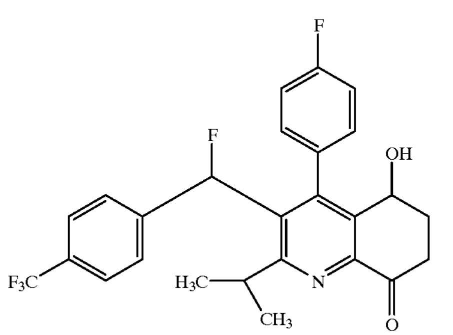 | | 0.20 Cy:EA (6:4) |

| Ex. No. | Structure | Isomer | R_f value |
|---|---|---|---|
| 142 | 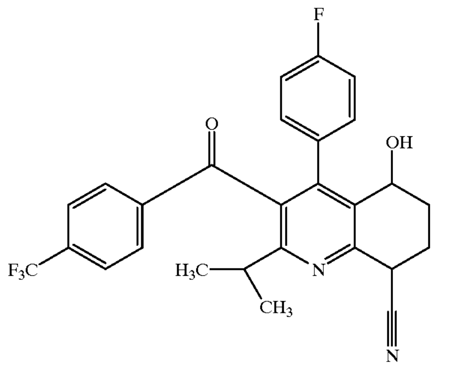 | | 0.18 Cy:EA (6:4) |
| 143 | 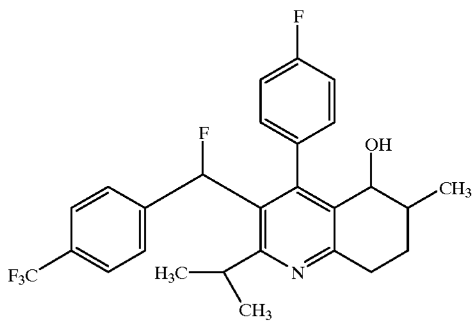 | | 0.15 Cy:EA (9:1) |
| 144 | 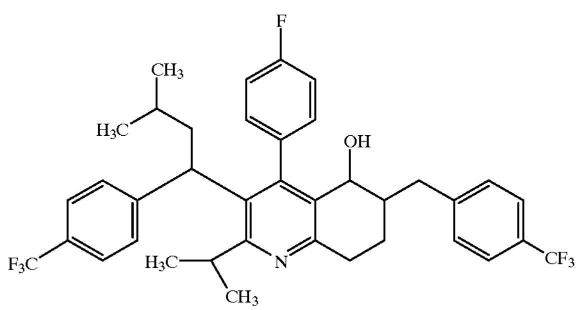 | | 0.29 Cy:EA (8.5:1) |
| 145 | 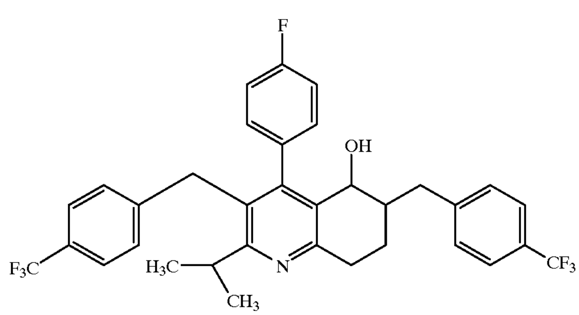 | | 0.17 Cy:EA (8.5:1) |

-continued

| Ex. No. | Structure | Isomer | R_f value |
|---|---|---|---|
| 146 | 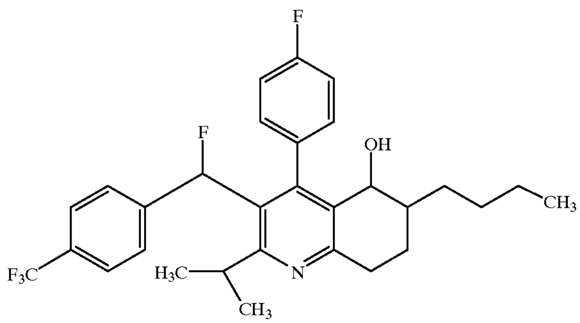 | | 0.20 Cy:EA (9:1) |
| 147 | 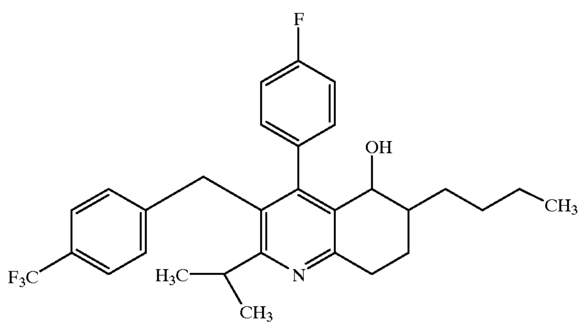 | | 0.13 Cy:EA (9:1) |
| 148 | 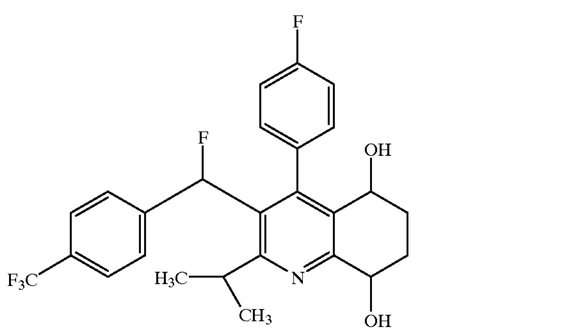 | | 0.32 Cy:EA (6:4) |
| 149 | 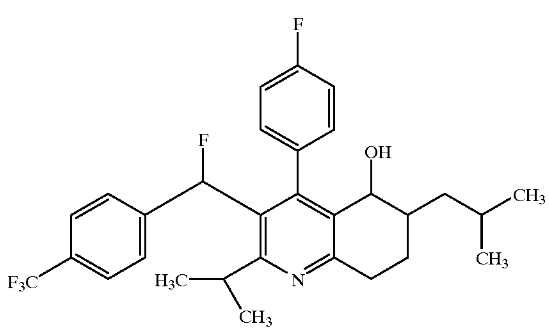 | | 0.22 Cy:EA (9:1) |

-continued

| Ex. No. | Structure | Isomer | $R_f$ value |
|---|---|---|---|
| 150 | 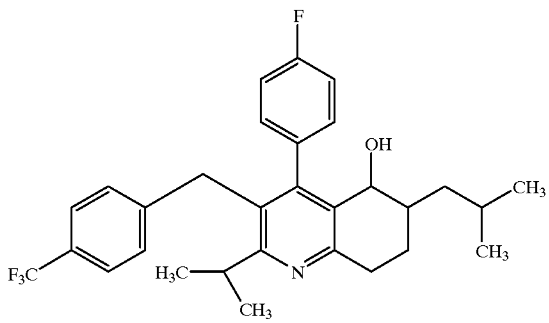 | | 0.14 Cy:EA (9:1) |
| 151 | 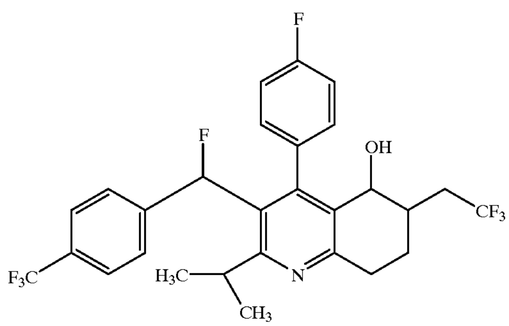 | | 0.12 Cy:EA (9:1) |
| 152 | 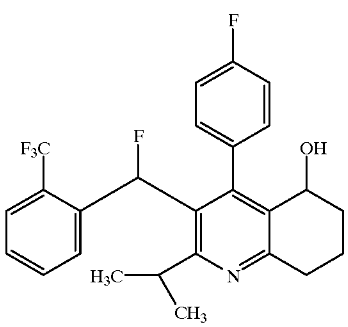 | Isomer I + II | 0.05/0.10 Cy:EA (10:1) |
| 153 | 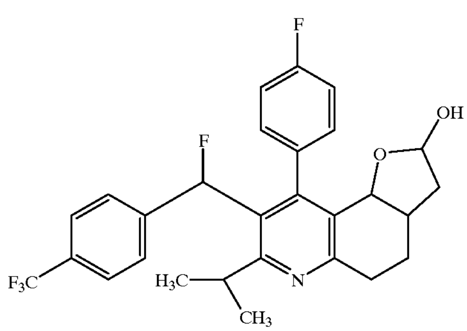 | Racemate | 0.36 Cy:EA (6:4) |

-continued

| Ex. No. | Structure | Isomer | $R_f$ value |
|---|---|---|---|
| 154 | 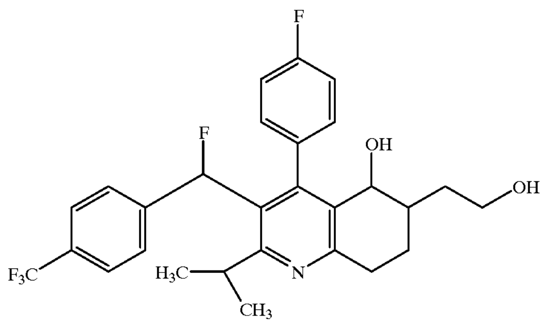 | Racemate | 0.13 Cy:EA (6:4) |
| 155 | 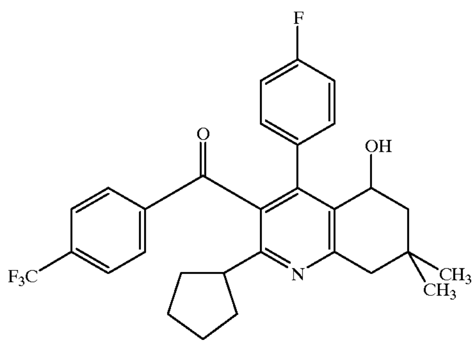 | | 0.55 Cy:EA (5:1) |
| 156 | 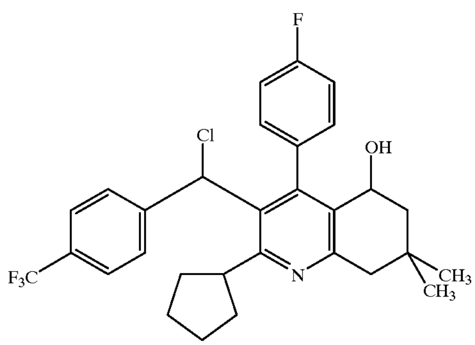 | Isomer I | 0.21 Cy:EA (10:1) |
| 157 | 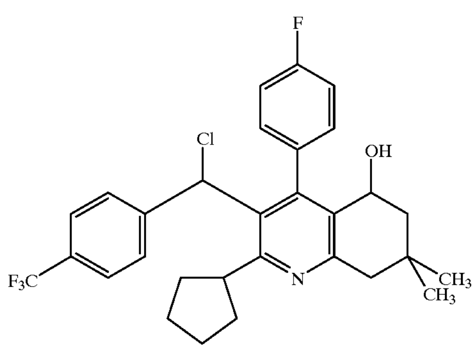 | Isomer II (+10% Isomer I) | 0.29 Cy:EA (10:1) |

-continued

| Ex. No. | Structure | Isomer | $R_f$ value |
|---|---|---|---|
| 158 | 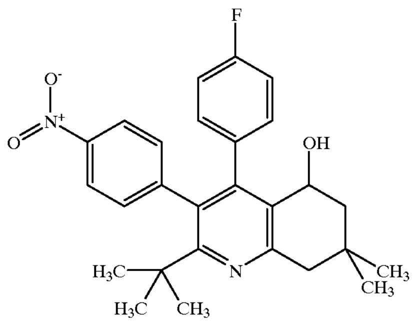 | | 0.32 Cy:EA (5:1) |
| 159 | 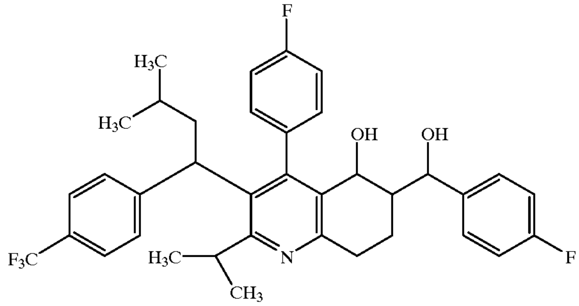 | Racemate | 0.23 Cy:EA (7:3) |
| 160 | 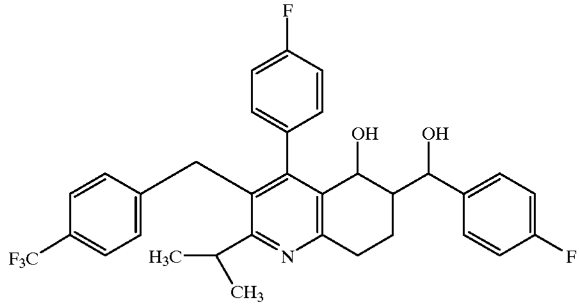 | Racemate | 0.16 Cy:EA (7:3) |
| 161 | 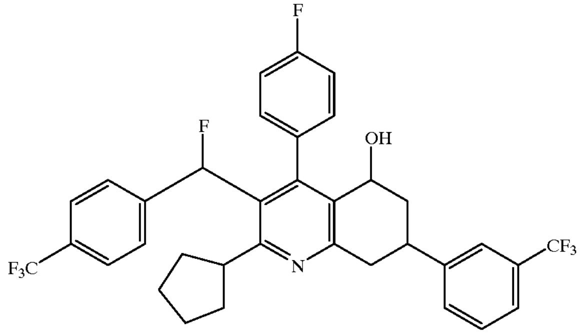 | Isomer I | 0.22 $CH_2Cl_2$:PE (7:3) |

-continued
| Ex. No. | Structure | Isomer | $R_f$ value |
|---|---|---|---|
| 162 | 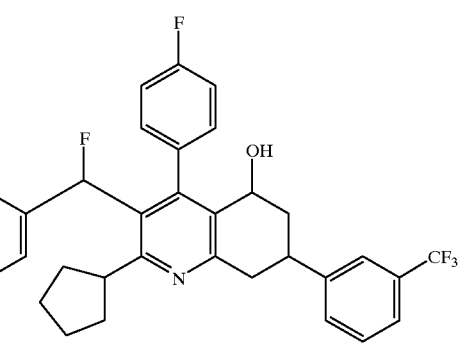 | Isomer II | 0.13 $CH_2Cl_2$:PE (7:3) |
| 163 | 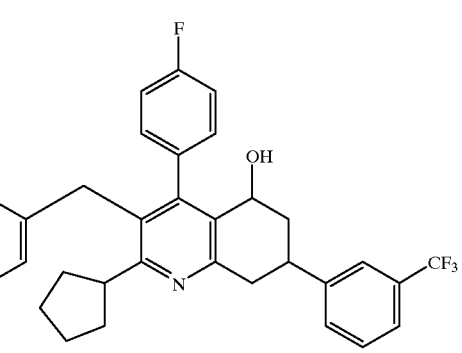 | Isomer I | 0.38 $CH_2Cl_2$ |
| 164 | 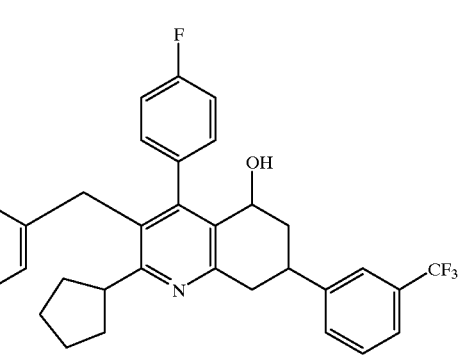 | Isomer II | 0.22 PE:EA (85:15) |
| 165 | 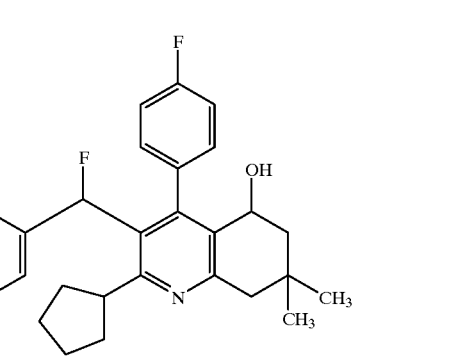 | Enantiomer I from Ex. No. 91 | 0.46 Tol:EA (9.5:0.5) |

-continued
| Ex. No. | Structure | Isomer | $R_f$ value |
|---|---|---|---|
| 166 | 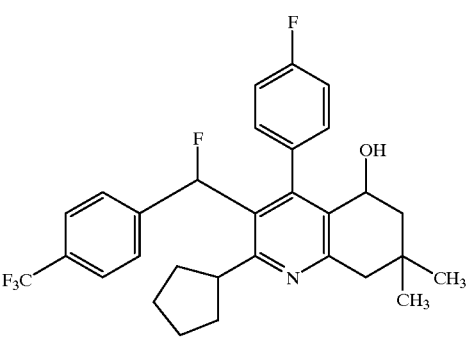 | Enantiomer II from Ex. No. 91 | 0.65 Tol:EA (9:1) |
| 167 | 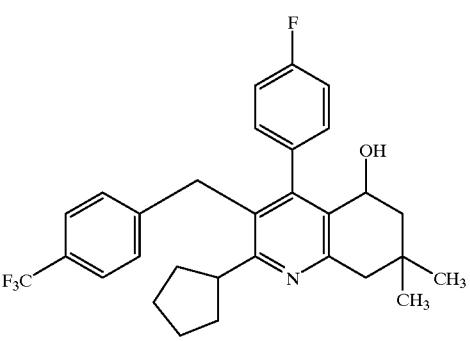 | Isomer I | Daicel chiralpak AD 10 μm: 11.52 n-Heptane:2-Propanol (98:2) |
| 168 | 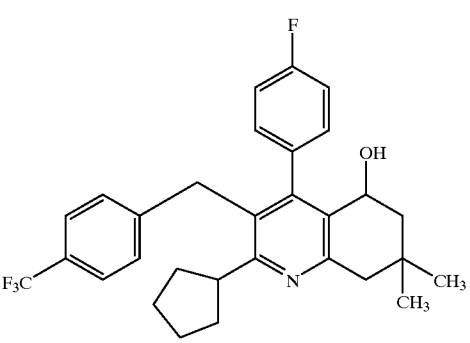 | Isomer II | Daicel chiralpak AD 10 μm: 12.60 n-Heptane:2-Propanol (98:2) |
| 169 | 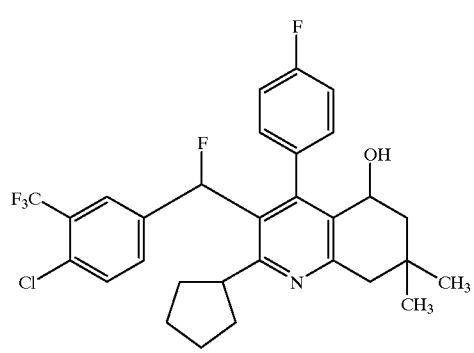 | Diastereomer 1 | 0.1 Cy:EA (10:1) |

-continued

| Ex. No. | Structure | Isomer | $R_f$ value |
|---|---|---|---|
| 170 | 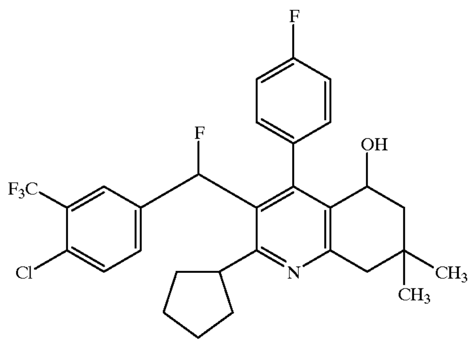 | Diastereomer 2 | 0.1 Cy:EA (10:1) |
| 171 | 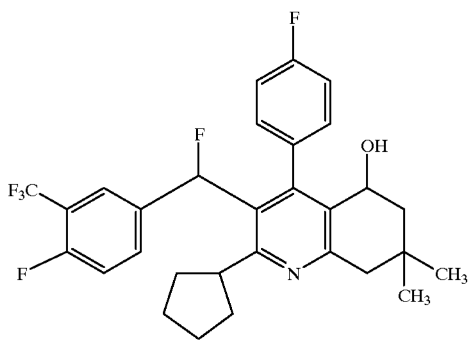 | Diastereomer 2 | 0.2 Cy:EA (9:1) |
| 172 | 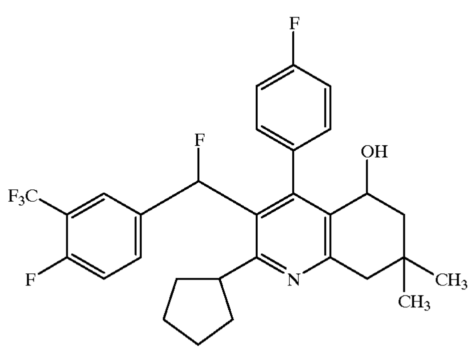 | Diastereomer 1 | 0.2 Cy:EA (9:1) |
| 173 | 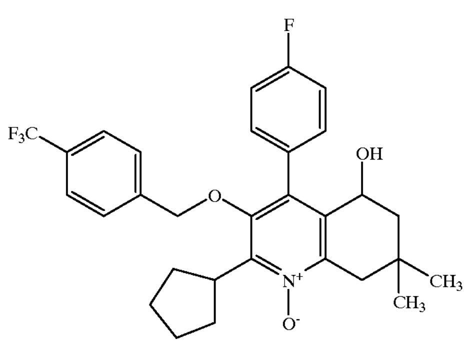 | | 0.69 EA:PE (1:1) |

-continued

| Ex. No. | Structure | Isomer | $R_f$ value |
|---|---|---|---|
| 174 | 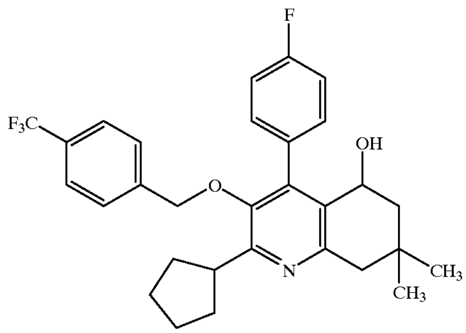 | | 0.35 Cy:EA (5:1) |
| 175 | 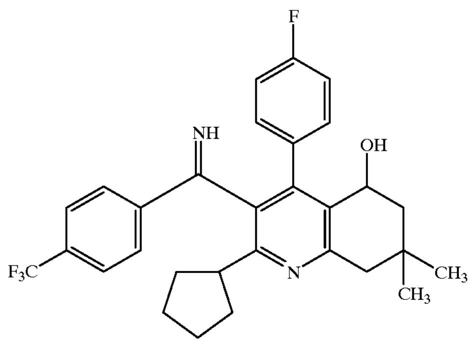 | | 0.08 Cy:EA (5:1) |
| 176 | 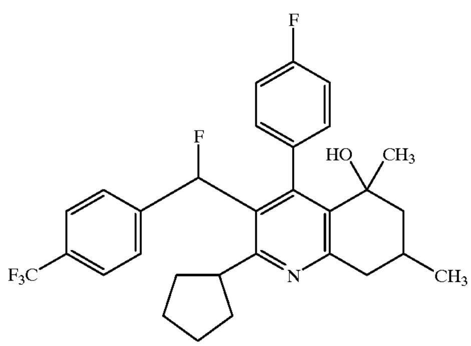 | | 0.50 Tol:EA (9:1) |
| 177 | 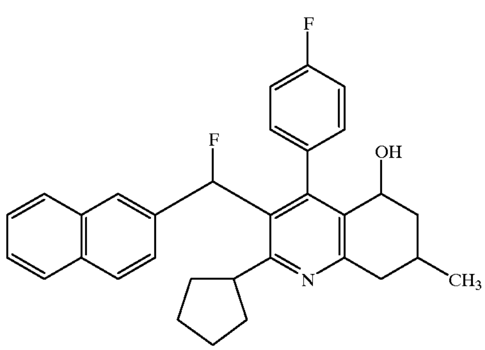 | diastereomer mixture | 0.4 Tol:EA (9:1) |

-continued

| Ex. No. | Structure | Isomer | $R_f$ value |
|---|---|---|---|
| 178 | (structure) | Isomer I | 0.5 Tol:EA (9:1) |
| 179 | (structure) | Isomer II | 0.34 Tol:EA (9:1) |
| 180 | (structure) | Isomer III | 0.52 Tol:EA (9:1) |
| 181 | (structure) | Isomer IV | 0.54 Tol:EA (9:1) |

-continued

| Ex. No. | Structure | Isomer | $R_f$ value |
|---|---|---|---|
| 182 | 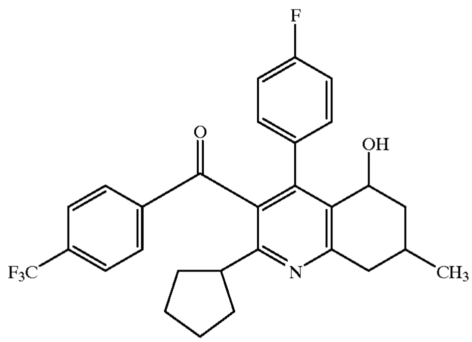 | | 0.45 Tol:EA (9:1) |
| 183 | 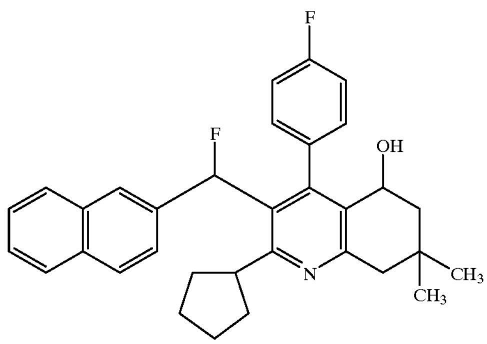 | Isomer I | 0.59 Tol:EA (9:1) |
| 184 | 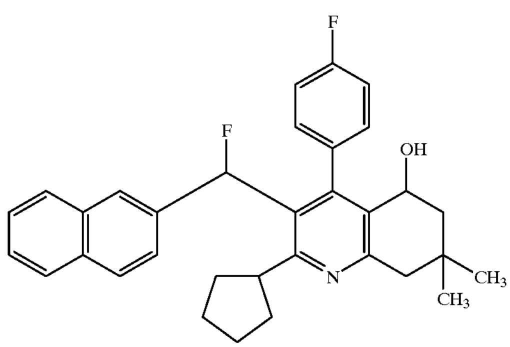 | Isomer II | 0.57 Tol:EA (9:1) |
| 185 | 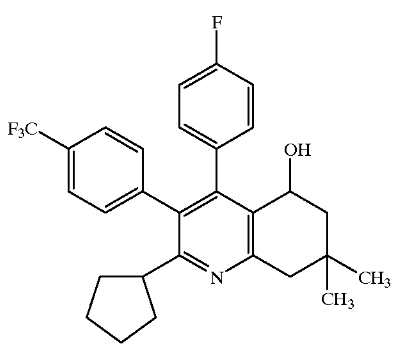 | | 0.40 EA:PE (1:5) |

-continued

| Ex. No. | Structure | Isomer | $R_f$ value |
|---|---|---|---|
| 186 | 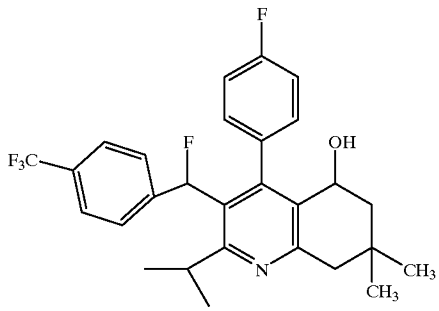 | | 0.53 Tol:EA (9:1) |
| 187 | 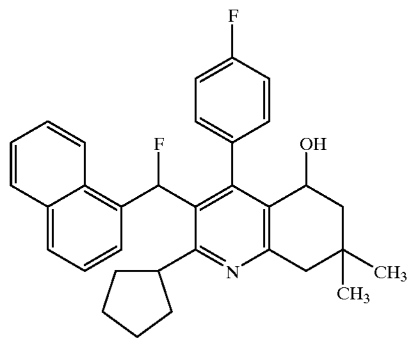 | diastereomer | 0.53 Cy:EA (9:1) |
| 188 | 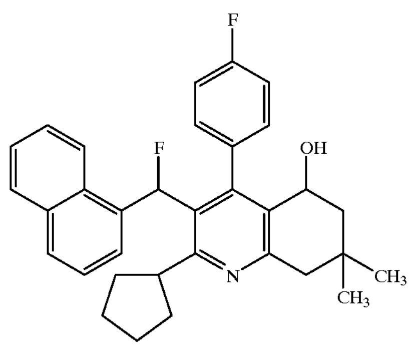 | diastereomer 2 | 0.18 Cy:EA (0.18) |
| 189 | 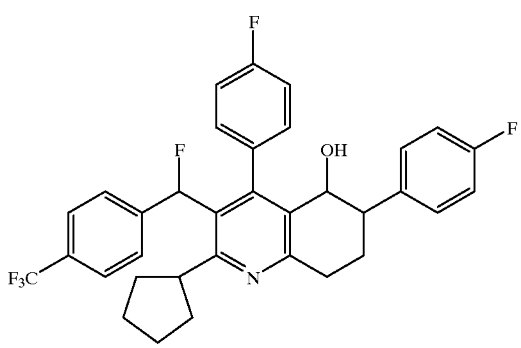 | diastereomer 1 | 0.58 Tol:EA (9:1) |

-continued

| Ex. No. | Structure | Isomer | R_f value |
|---|---|---|---|
| 190 | 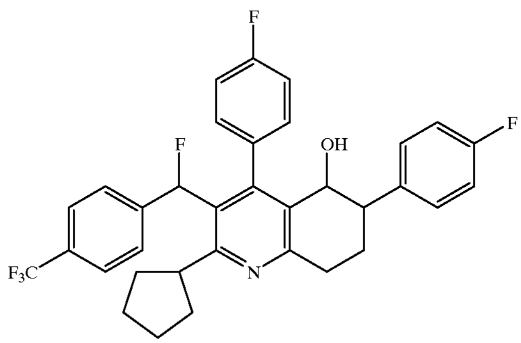 | diastereomer 2 | 0.57 Tol:EA (9:1) |
| 191 | 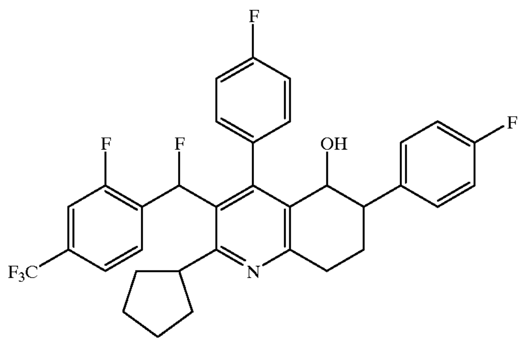 | diastereomer 1 | 0.67 Tol:EA (9:1) |
| 192 | 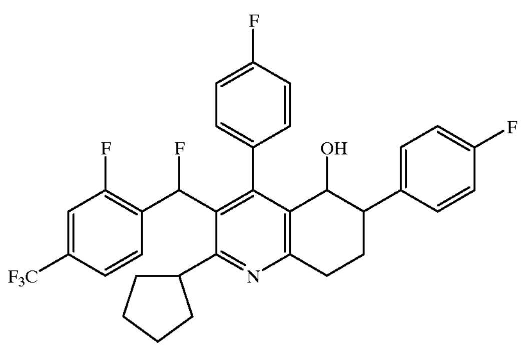 | diastereomer 2 | 0.59 Tol:EA (9:1) |
| 193 | 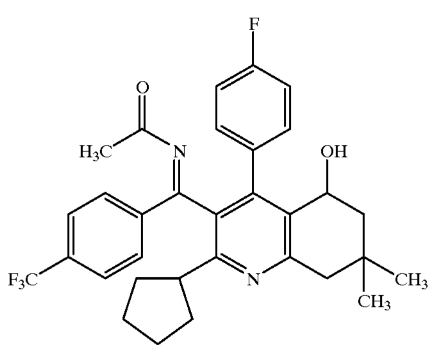 | diastereomer 1 | 0.23 Cy:EA (5:1) |

| Ex. No. | Structure | Isomer | $R_f$ value |
|---|---|---|---|
| 194 | 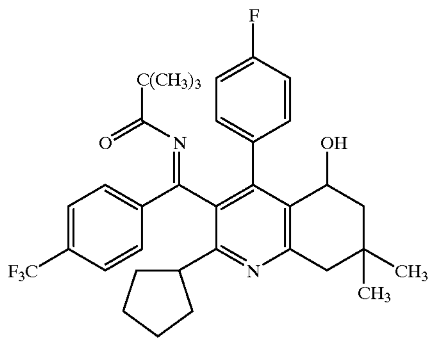 | diastereomer 1 | 0.30 Cy:EE (5:1) |
| 195 | 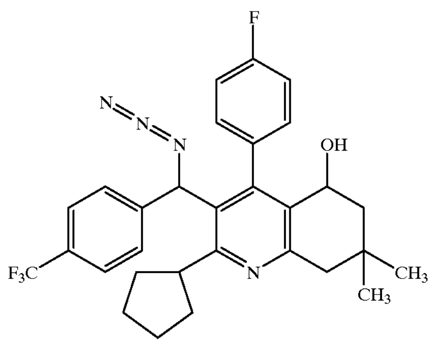 | 2 diastereomere RS (2:1) | 0.50 EA:PE (1:5) |
| 196 | 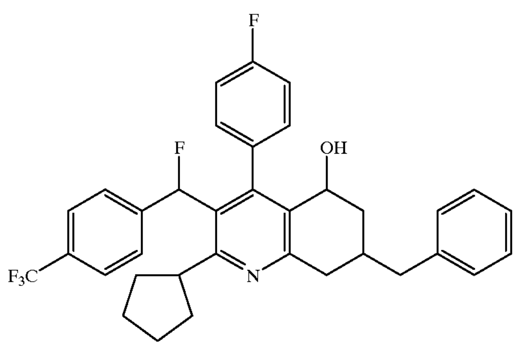 | Isomer I | 0.17 CH$_2$Cl$_2$:PE (8:2) |
| 197 | 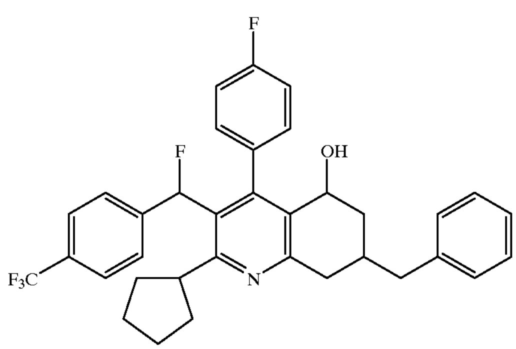 | Isomer II | 0.29 CH$_2$Cl$_2$:PE (8:2) |

-continued

| Ex. No. | Structure | Isomer | $R_f$ value |
|---|---|---|---|
| 198 | 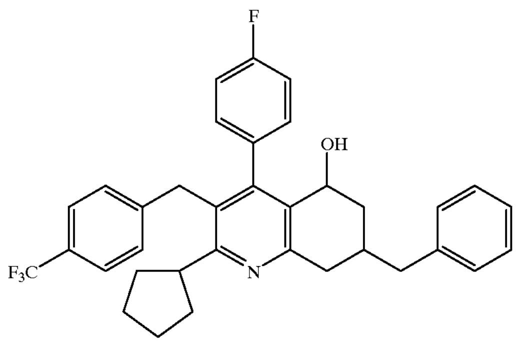 | | 0.15 $CH_2Cl_2$:PE (8:2) |
| 199 | 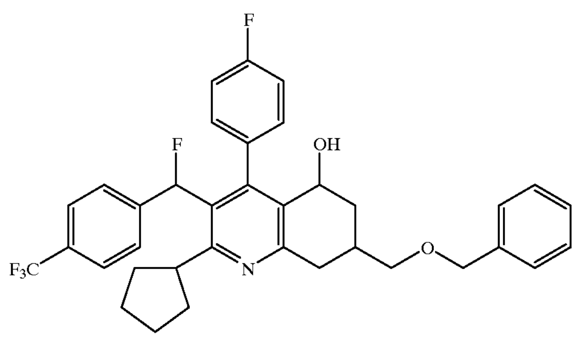 | Isomer I | 0.22 PE:EA (8:2) |
| 200 | 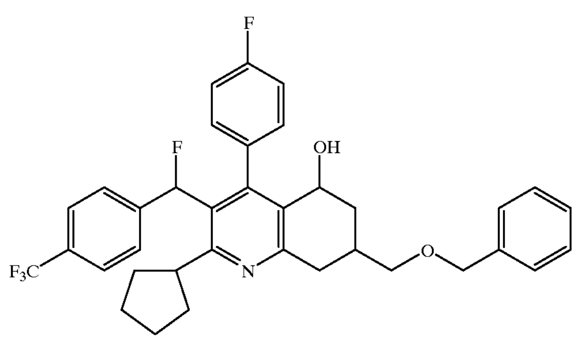 | Isomer II | 0.25 PE:EE (8:2) |
| 201 | 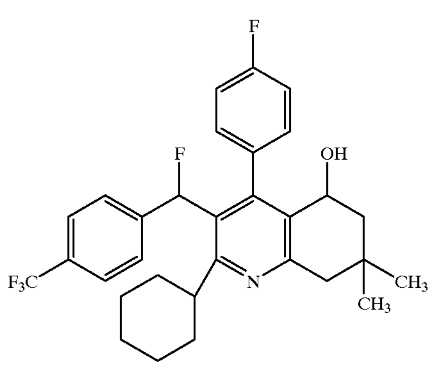 | Isomer I | 0.29 PE:EA (85:15) |

-continued

| Ex. No. | Structure | Isomer | $R_f$ value |
|---|---|---|---|
| 202 | 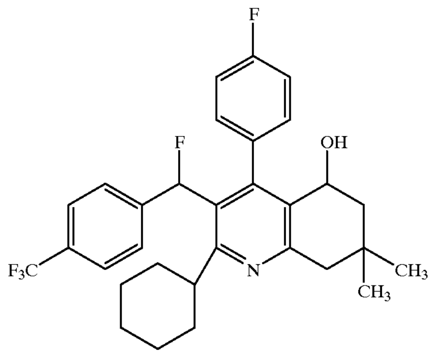 | Isomer II | 0.32<br>PE:EA<br>(85:15) |
| 203 | 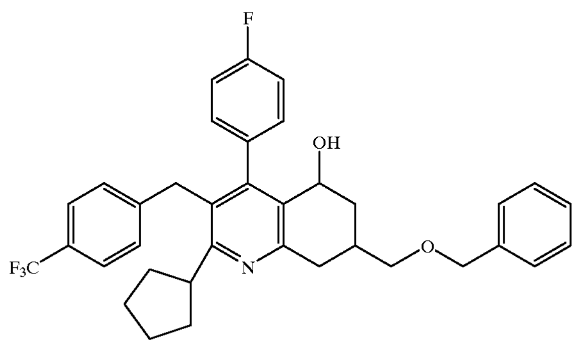 | Isomer I | 0.37<br>$CH_2Cl_2$:EA<br>(95:5) |
| 204 | 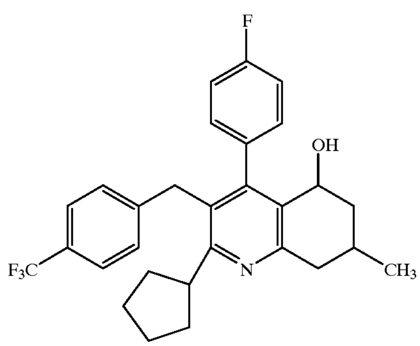 | Enantiomer I of Ex. No. 102 | Merck (R,R)<br>Wheel KO<br>1.5 μm: 10.76<br>n-Heptane:2-Propanol<br>(97.5:2.5) |
| 205 | 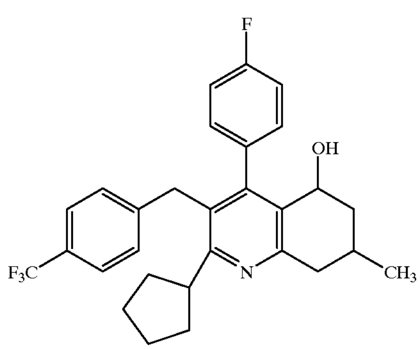 | Enantiomer II of Ex. No. 102 | Merck (R,R)<br>Wheel KO<br>1.5 μm: 8.98<br>n-Heptane:2-Propanol<br>(97.5:2.5) |

-continued

| Ex. No. | Structure | Isomer | $R_f$ value |
|---|---|---|---|
| 206 | 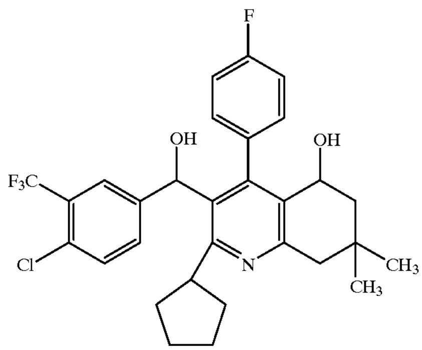 | diastereomer 2 | 0.005 Cy:EA (10:1) |
| 207 | 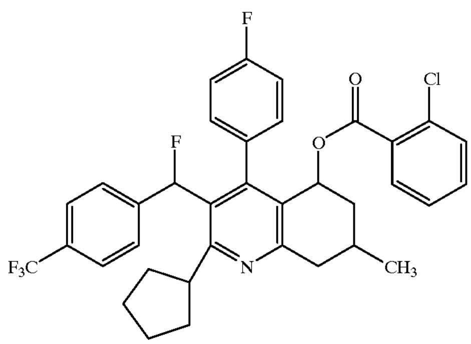 | diastereomer 4 | 0.66 Tol:EA (9:1) |
| 208 | 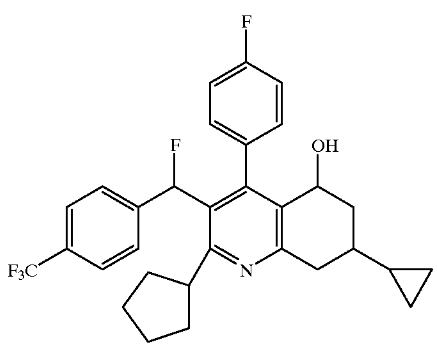 | diastereomer mixture I | 0.55 Tol:EA (9:1) |
| 209 | 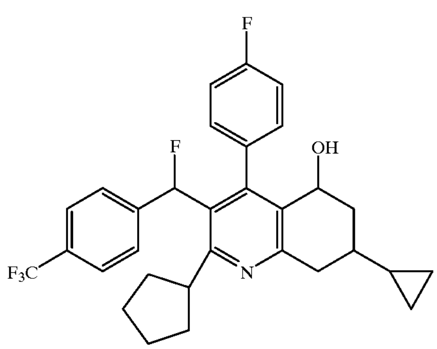 | diastereomers mixture II | 0.60 Tol:EA (9:1) |

-continued

| Ex. No. | Structure | Isomer | $R_f$ value |
|---|---|---|---|
| 210 | 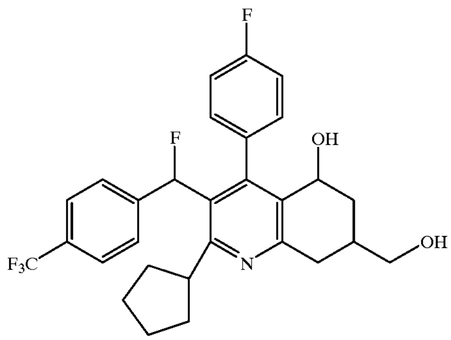 | Isomer A | 0.23 PE:EA (1:1) |
| 211 | 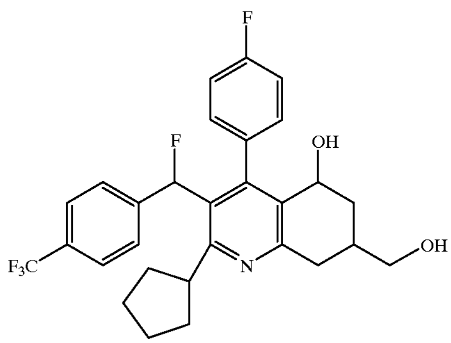 | Isomer B | 0.23 PE:EA (1:1) |
| 212 | 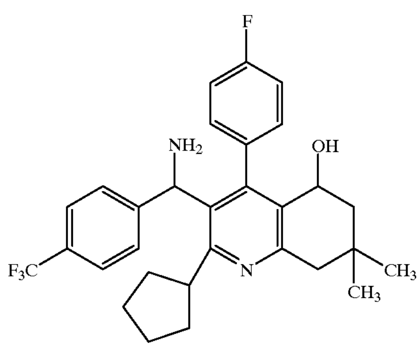 | Isomer I | 0.29 EA:PE (1:2) |
| 213 | 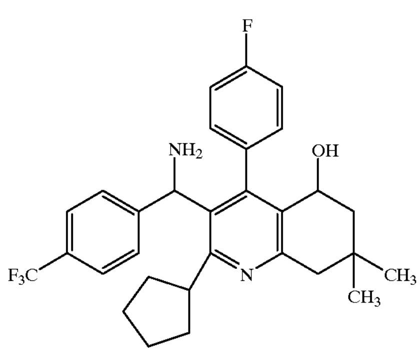 | Isomer II | 0.48 EA:PE (1:2) |

-continued

| Ex. No. | Structure | Isomer | R_f value |
|---|---|---|---|
| 214 | 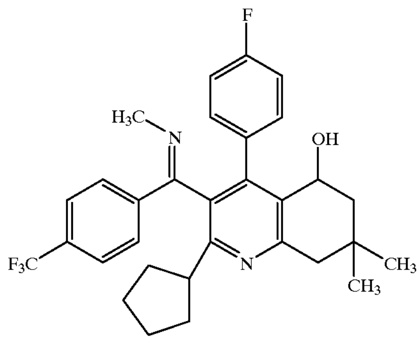 | Isomer I | 0.38 EA:PE (1:5) |
| 215 | 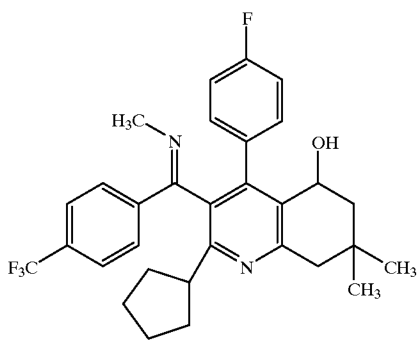 | Isomer II | 0.17 EA:PE (1:5) |
| 216 | 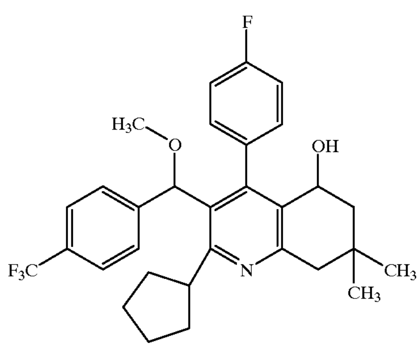 | | 0.10 EA:PE (1:10) |
| 217 | 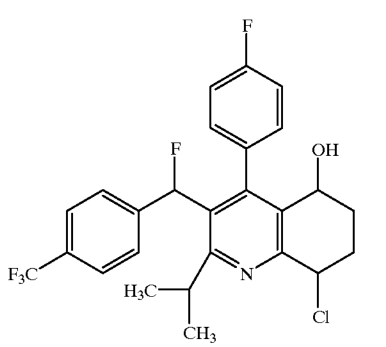 | diastereomer 2 | 0.17 Cy:EA (9:1) |

-continued

| Ex. No. | Structure | Isomer | $R_f$ value |
|---|---|---|---|
| 218 | 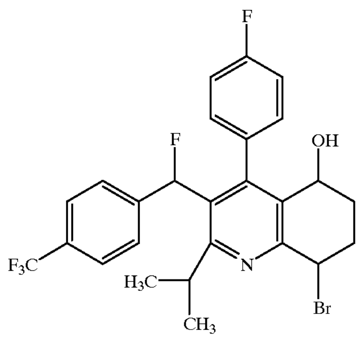 | diastereomer 2 | 0.12 Cy:EA (9:1) |
| 219 | 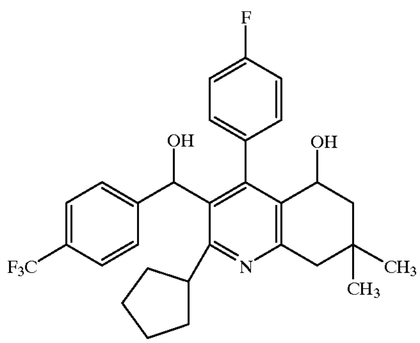 | Isomer I | 0.36 Tol:EA (8:2) |
| 220 | 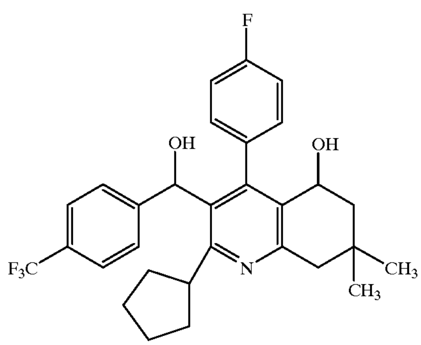 | Isomer II | 0.303 Tol:EA (9:1) |
| 221 | 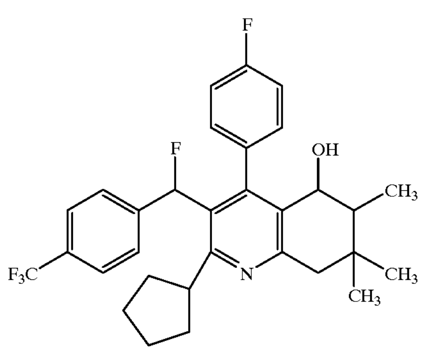 | diastereomer mixture | 0.23 Cy:EA (9:1) |

-continued

| Ex. No. | Structure | Isomer | $R_f$ value |
|---|---|---|---|
| 222 | 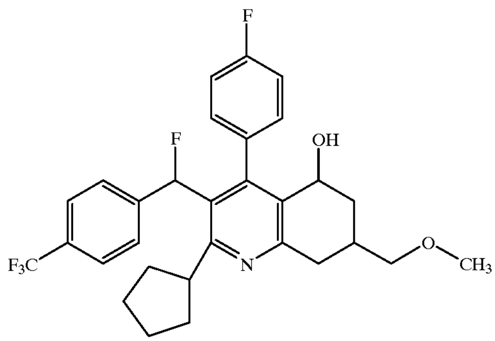 | Isomer I | 0.27 PE:EA (7:3) |
| 223 | 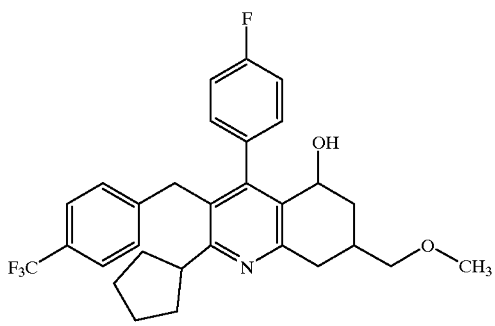 | Isomer I | 0.10 PE:EA (8:2) |
| 224 | 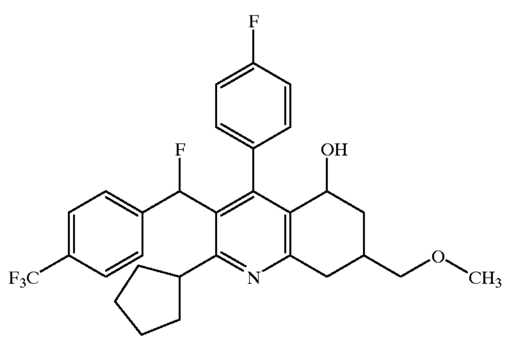 | Isomer II | 0.28 PE:EA (7:3) |
| 225 | 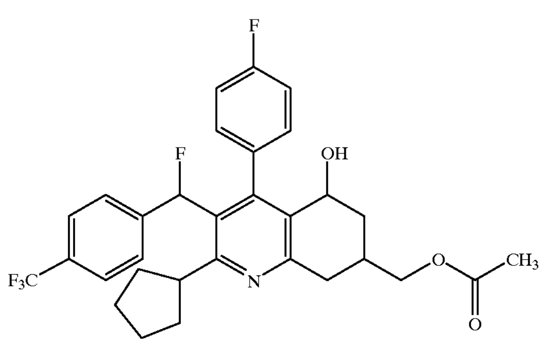 | Isomer I | 0.33 PE:EA (7:3) |

-continued

| Ex. No. | Structure | Isomer | $R_f$ value |
|---|---|---|---|
| 226 | 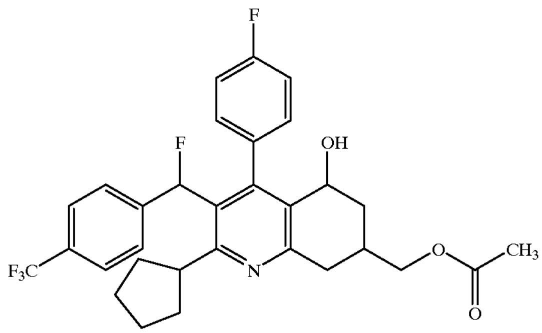 | Isomer II | 0.31<br>PE:EA<br>(7:3) |
| 227 | 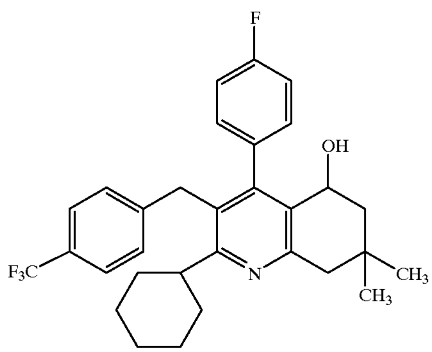 | | 0.22<br>$CH_2Cl_2$ |
| 228 | 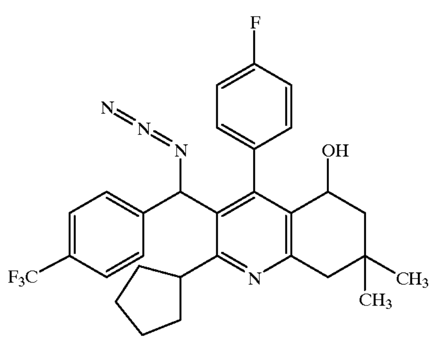 | Isomer I | 0.18<br>EA:PE<br>(1:10) |
| 229 | 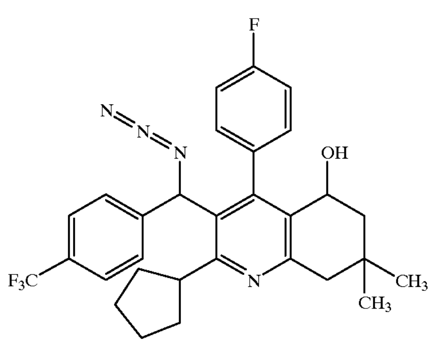 | Isomer II | 0.26<br>EA:PE<br>(1:10) |

-continued

| Ex. No. | Structure | Isomer | $R_f$ value |
|---|---|---|---|
| 230 | 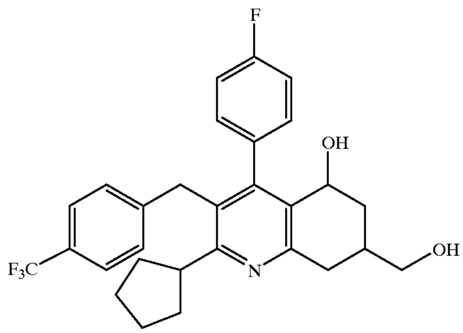 | | 0.19 PE:EA (1:1) |
| 231 | 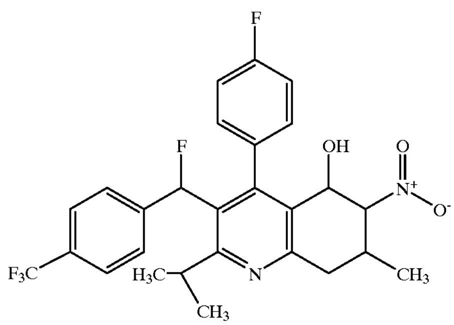 | diastereomer 1 | 0.2 Tol:EA (9:1) |
| 232 | 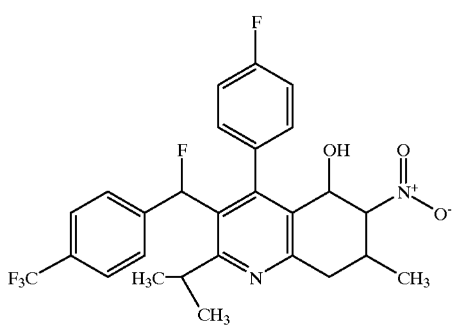 | diastereomer 2 | 0.121 Toluene |
| 233 | 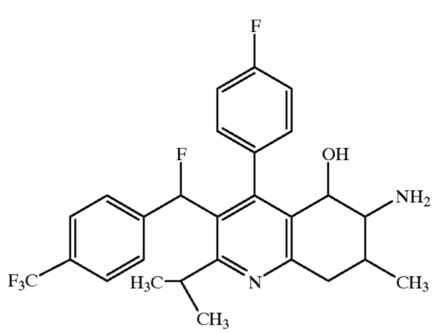 | diastereomer 2 | 0.18 EA:MeOH (8:2) |

| Ex. No. | Structure | Isomer | R_f value |
|---|---|---|---|
| 234 | 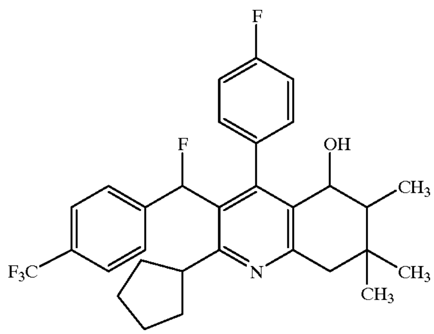 | diastereomer 1 | 0.26 Cy:EA (9:1) |
| 235 | 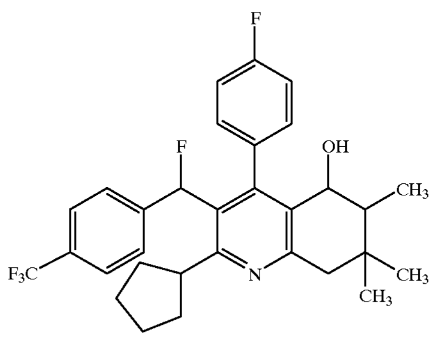 | diastereomer 2 | 0.22 Cy:EA (9:1) |
| 236 | 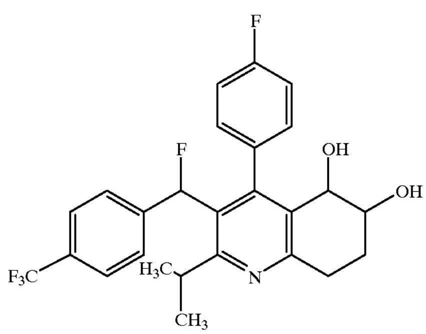 | | 0.2 Cy:EA (6:4) |
| 237 | 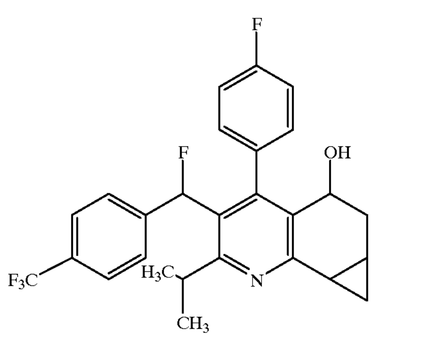 | diastereomer 2 | |

-continued

| Ex. No. | Structure | Isomer | $R_f$ value |
|---|---|---|---|
| 238 | 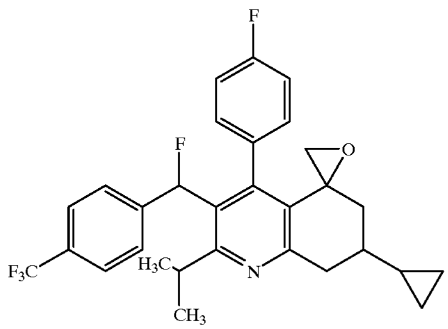 | Isomer mixture | MS:m/z 514 (M + H) |
| 239 | 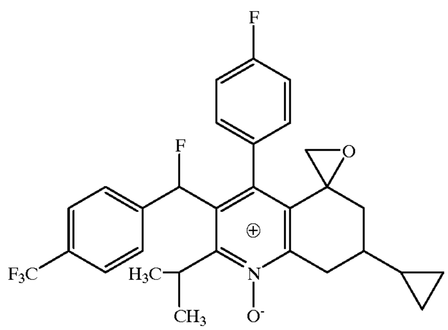 | Isomer mixture | MS:m/z 530 (M + H) |
| 240 | 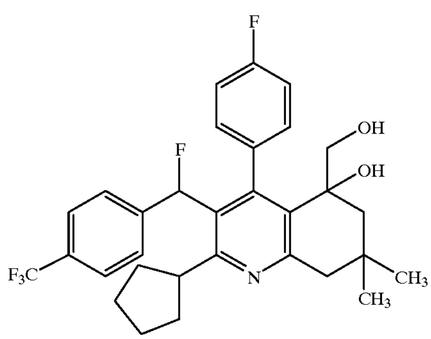 | Isomer I | 0.70 Tol:EA (9:1) |
| 241 | 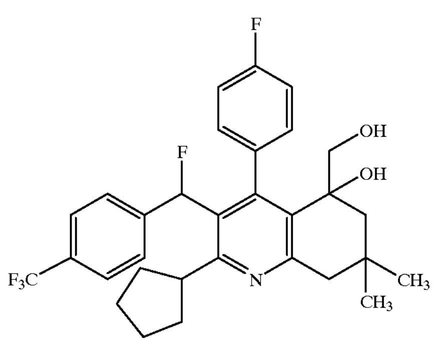 | Isomer II | 0.23 Tol:EA (9:1) |

-continued

| Ex. No. | Structure | Isomer | $R_f$ value |
|---|---|---|---|
| 242 | 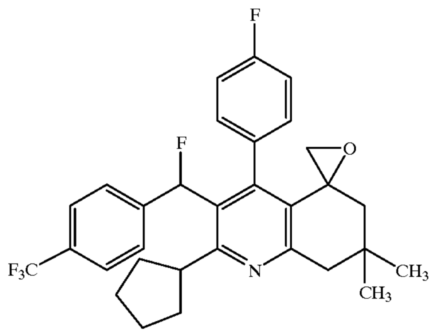 | Isomer mixture | 0.39 Tol:EA (9:1) |
| 243 | 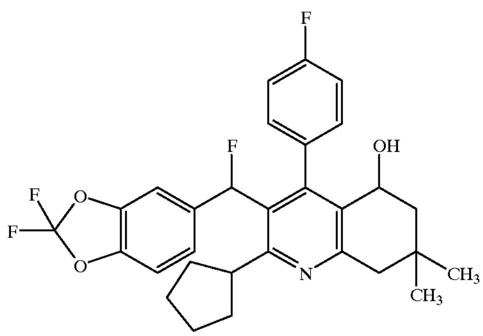 | Isomer I | 0.37 Tol:EA (9:1) |
| 244 | 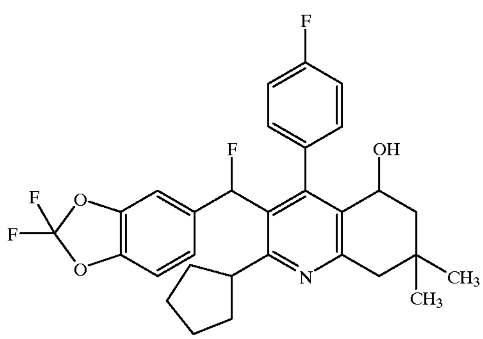 | Isomer II | 0.48 Tol:EA (9:1) |
| 245 | 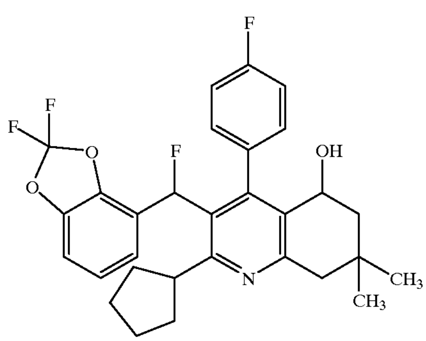 | diastereomer mixture | 0.5/0.56 Tol:EA (9:1) |

-continued

| Ex. No. | Structure | Isomer | R_f value |
|---|---|---|---|
| 246 | 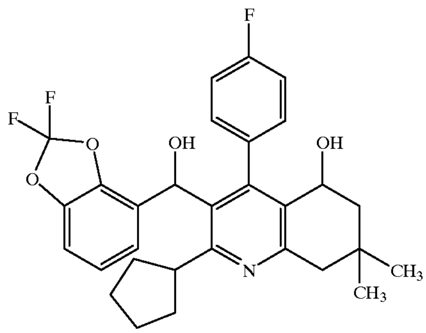 | Isomer I | 0.31 Tol:EA (9:1) |
| 247 | 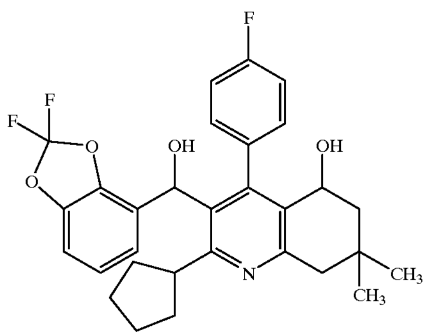 | Isomer II | 0.12 Tol:EA (9:1) |
| 248 | 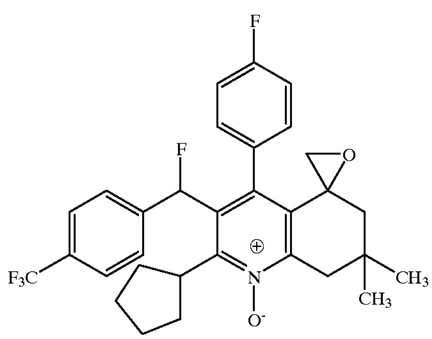 | Isomer mixture | 0.16 Tol:EA (9:1) |
| 249 | 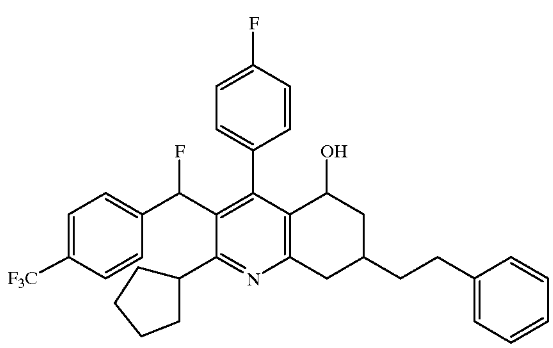 | Isomer I1 | 0.26 PE:EA (9:1) |

-continued

| Ex. No. | Structure | Isomer | $R_f$ value |
|---|---|---|---|
| 250 | 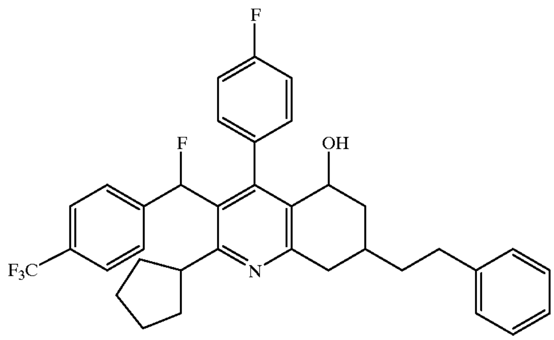 | Isomer I2 | 0.19 PE:EA (9:1) |
| 251 | 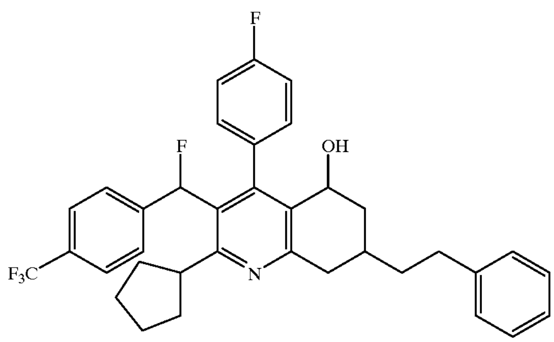 | Isomer I1 | 0.23 PE:EA (9:1) |
| 252 | 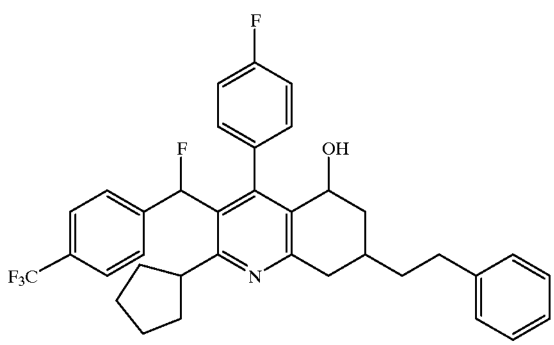 | Isomer II2 | 0.17 PE:EA (9:1) |
| 253 | 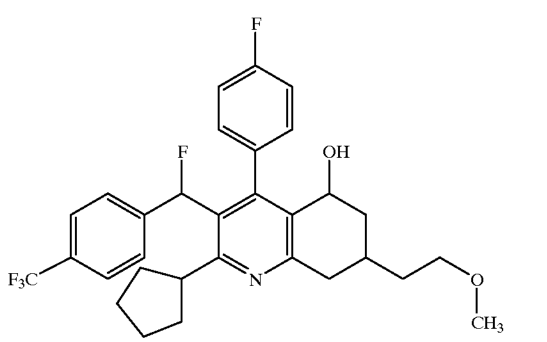 | Isomer I, racemic | 0.20 PE:EA (4:1) |

| Ex. No. | Structure | Isomer | $R_f$ value |
|---|---|---|---|
| 254 | 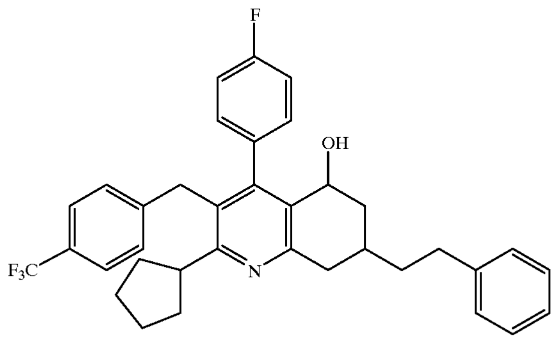 | racemic mixture | 0.36 PE:EA (9:1) |
| 255 | 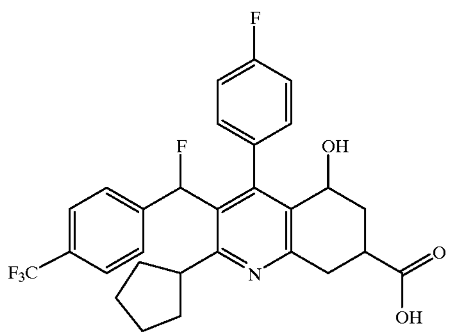 | Isomer II | 0.68 $CH_2Cl_2$:MeOH (8:1) |
| 256 | 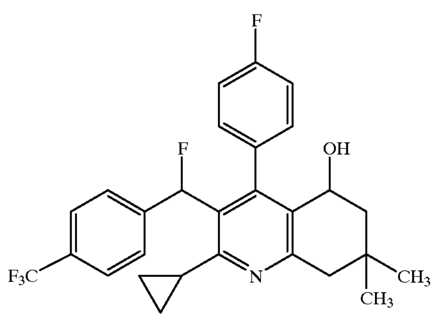 | Isomer I | 0.32 PE:EA (9:1) |
| 257 | 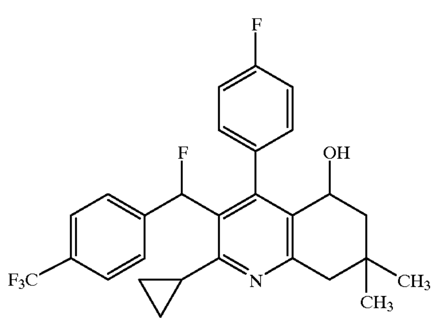 | Isomer II | 0.29 PE:EA (9:1) |

-continued
| Ex. No. | Structure | Isomer | $R_f$ value |
|---|---|---|---|
| 258 | 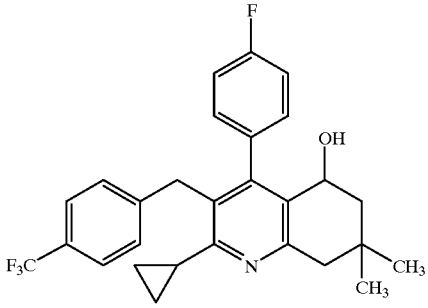 | | 0.22 PE:EA (9:1) |
| 259 | 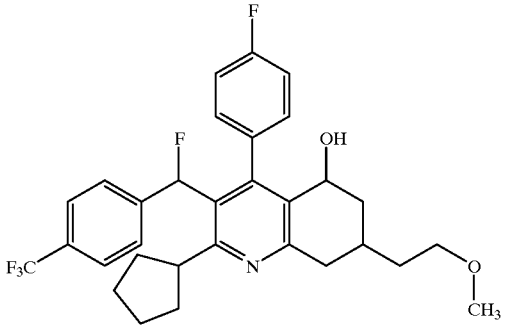 | Isomer II | 0.15 PE:EA (4:1) |
| 260 | 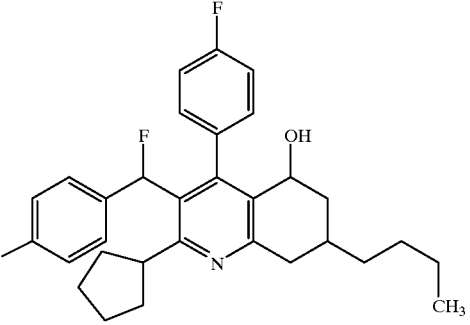 | Isomer II | 043 PE:EA (9:1) |
| 261 | 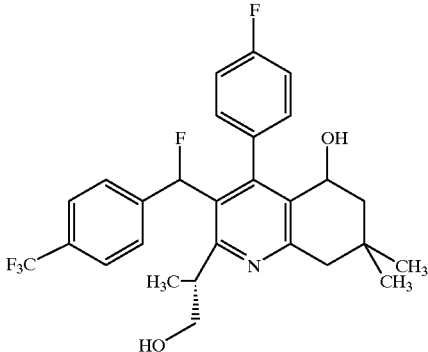 | diastereomer 1 | 0.44 PE:EA (7:3) |

| Ex. No. | Structure | Isomer | $R_f$ value |
|---|---|---|---|
| 262 | 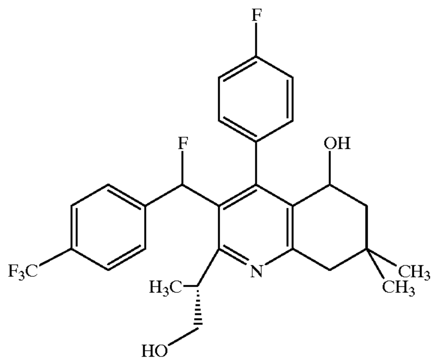 | diastereomer 2 | 0.37 PE:EA (7:3) |
| 263 | 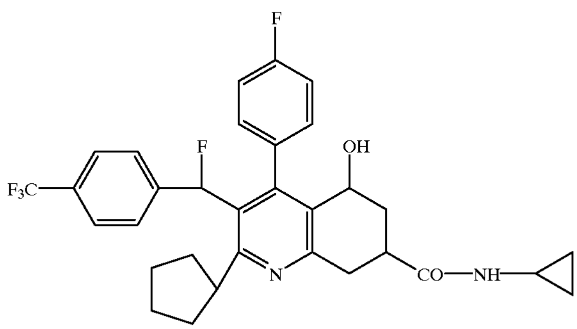 | | 0.15 PE:EA (1:1) |
| 264 | 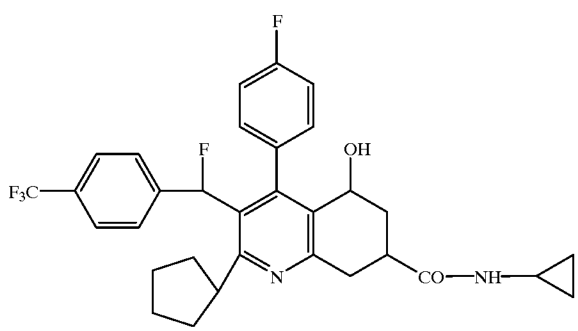 | | 0.16 PE:EA (1:1) |
| 265 | 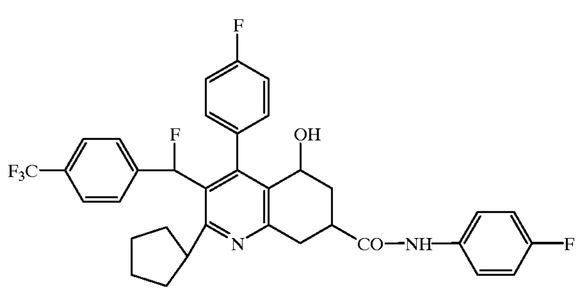 | | 0.44 PE:EA (3:2) |

-continued

| Ex. No. | Structure | Isomer | $R_f$ value |
|---|---|---|---|
| 266 | 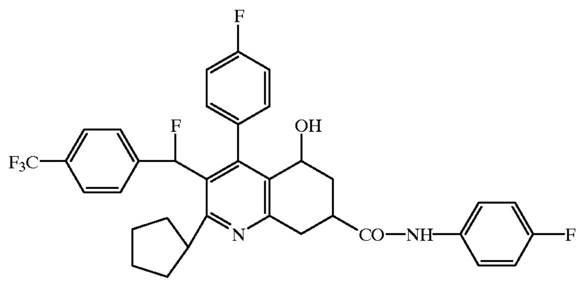 | | 0.48 PE:EA (3:2) |
| 267 | 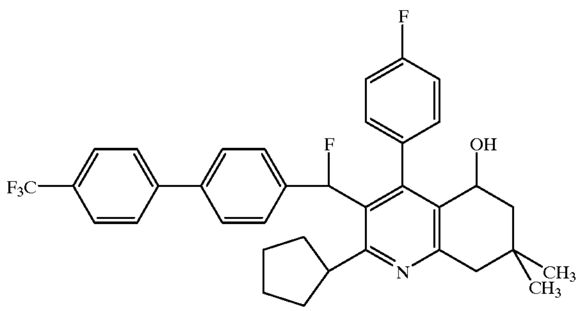 | Isomer I | 0.57 Tol:EA (9:1) |
| 268 | 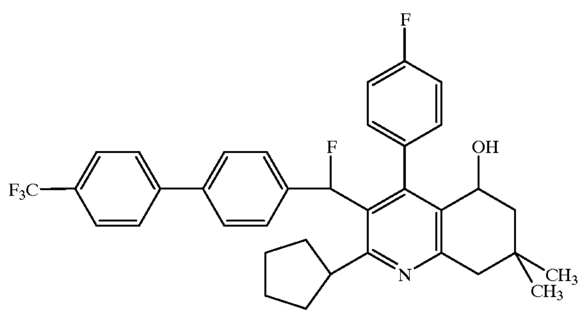 | Isomer II | 0.53 Tol:EA (9:1) |
| 269 | 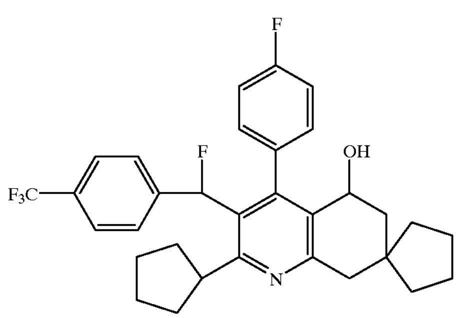 | Isomer I | 0.35 Cyc/THF (9:1) |
| 270 | 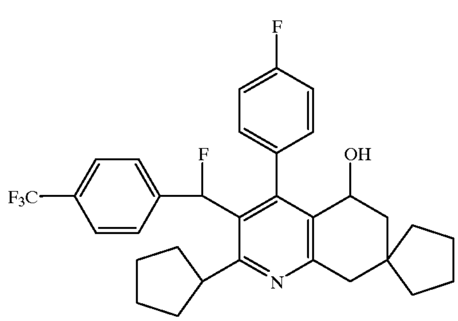 | Isomer II | 0.30 Cyc:THF (9:1) |

| Ex. No. | Structure | Isomer | $R_f$ value |
|---|---|---|---|
| 271 | 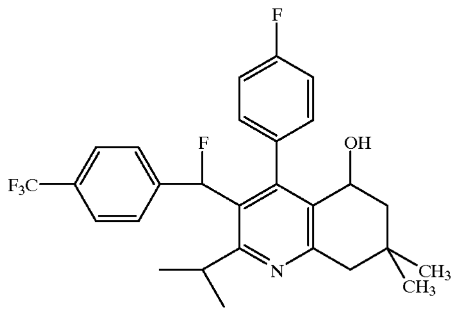 | Enantiomer I | 0.52 Tol:EA (9:1) |
| 272 | 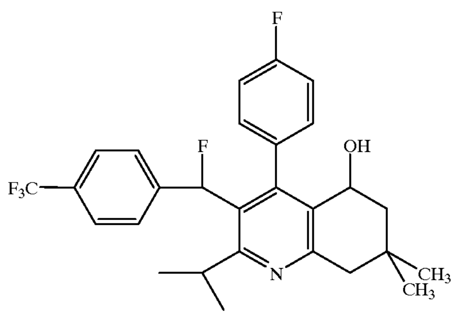 | Enantiomer II | 0.51 Tol:EA (9:1) |
| 273 | 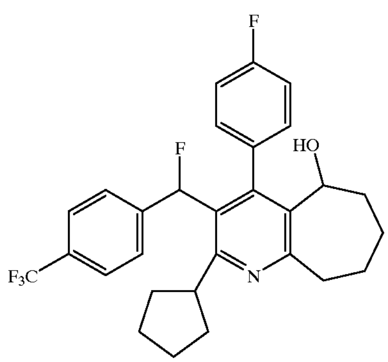 | | |
| 274 | 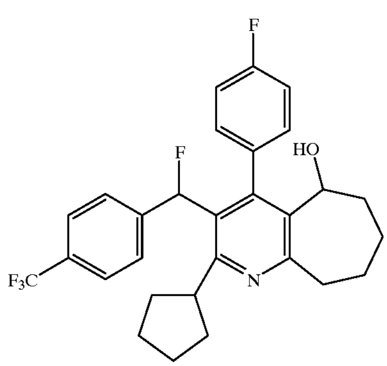 | diastereomer 1 | |

-continued

| Ex. No. | Structure | Isomer | R_f value |
|---|---|---|---|
| 275 | 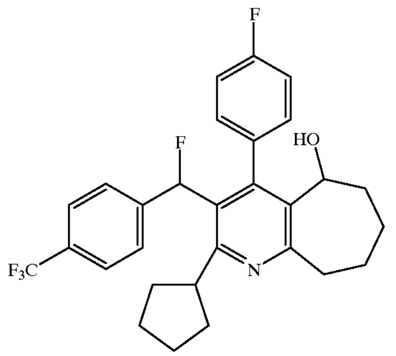 | diastereomer 2 | |
| 276 | 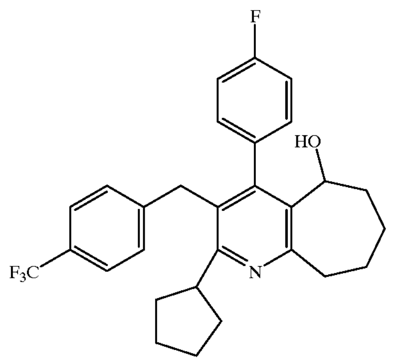 | | |
| 277 | 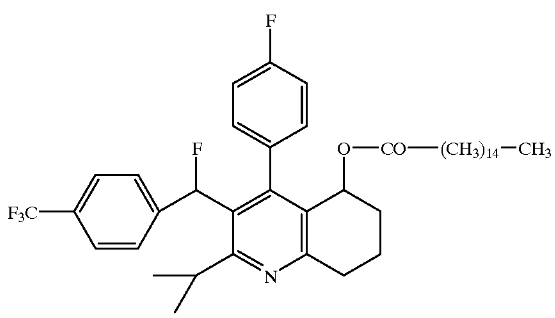 | diastereomer 2 | 0.37 PE:EA (10:1) |
| 278 | 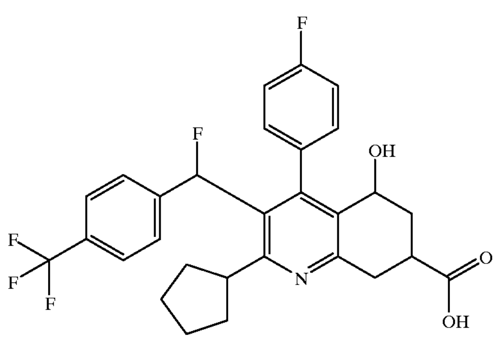 | Isomer I | 0.35 CH$_2$Cl$_2$/MeOH (20:1) |

-continued

| Ex. No. | Structure | Isomer | $R_f$ value |
|---|---|---|---|
| 279 | 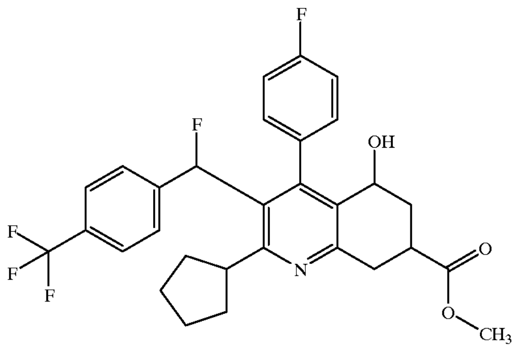 | Isomer I | 0.25 PE/EA (4:1) |
| 280 | 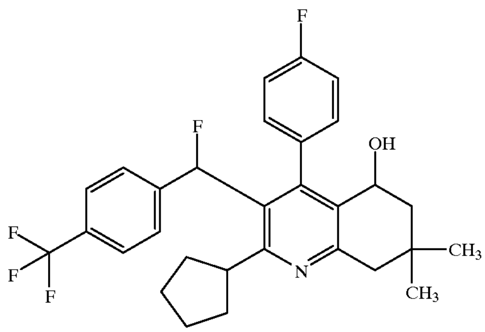 | Enantiomer I from Isomer I of Ex. No. 78 | 0.586 Tol/EA (9:1) |
| 281 | 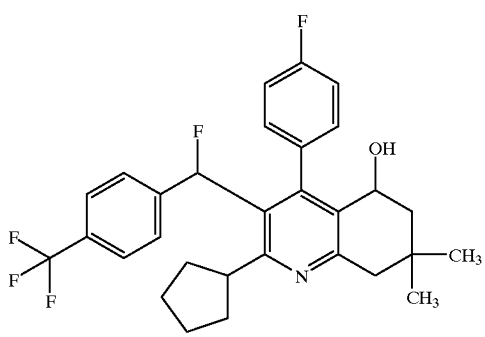 | Enantiomer II from Isomer I of Ex. No. 78 | 0.55 Tol/EA (9:1) |
| 282 | 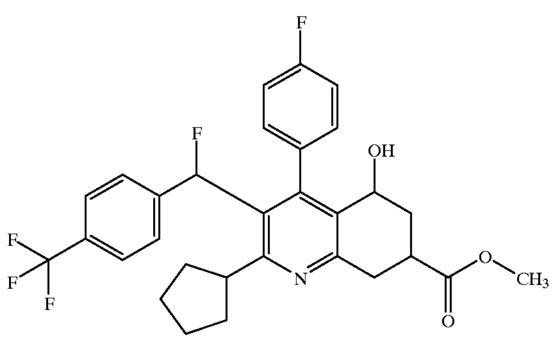 | Isomer II | 0.23 PE/EA (4:1) |

-continued

| Ex. No. | Structure | Isomer | $R_f$ value |
|---|---|---|---|
| 283 | 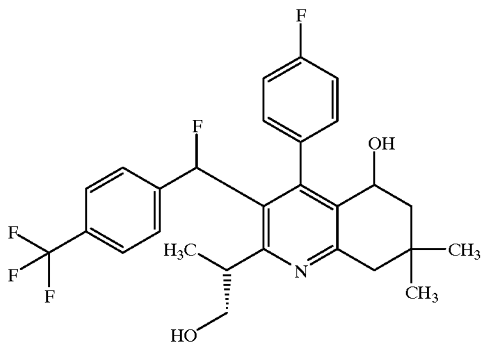 | IIa | 0.17 PE/EA (4:1) |
| 284 | 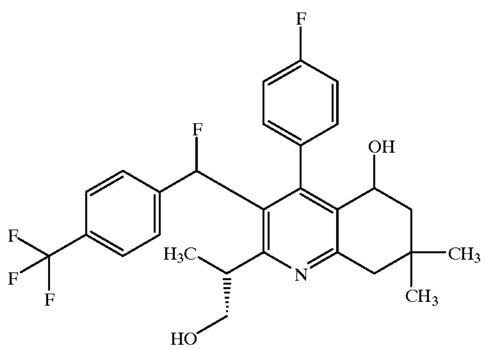 | IIb | 0.11 PE/EA (4:1) |
| 285 | 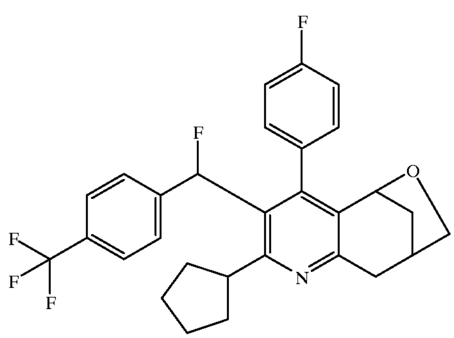 | Isomer II | 0.21 PE/EA (9:1) |
| 286 | 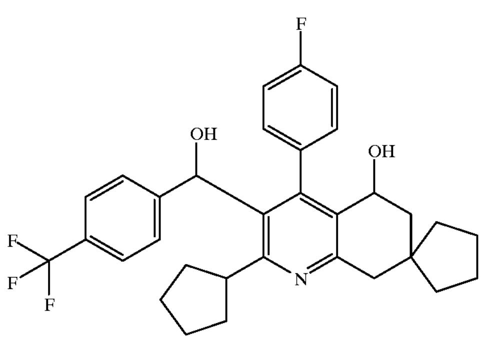 | diastereomer 1 | 0.16 Tol/EA (9:1) |

-continued

| Ex. No. | Structure | Isomer | $R_f$ value |
|---|---|---|---|
| 287 | 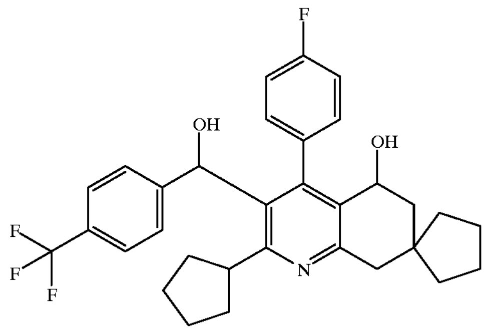 | diastereomer 2 | 0.4 Tol/EA (9:1) |
| 288 | 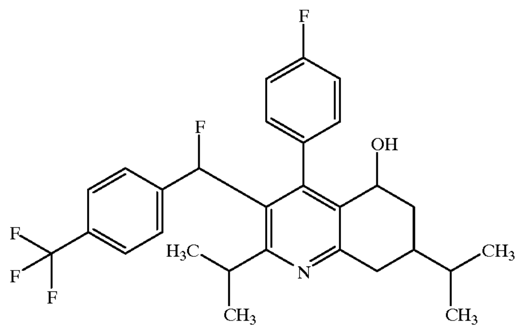 | diastereomer 1 | 0.59 Tol/EA (9:1) |
| 289 | 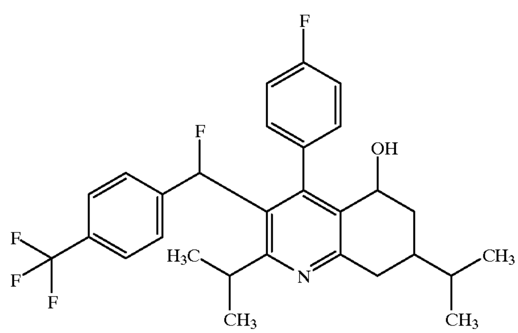 | diastereomer 2 | 0.67 Tol/EA (9:1) |
| 290 | 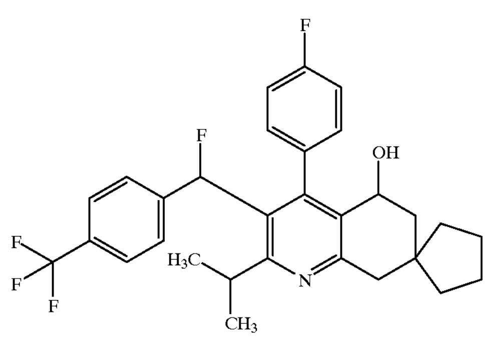 | diastereomer 1 | 0.22 (9:1) |

-continued
| Ex. No. | Structure | Isomer | $R_f$ value |
|---|---|---|---|
| 291 | 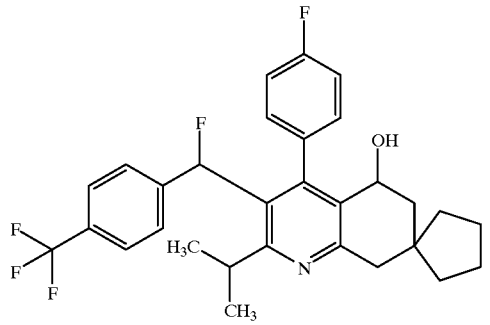 | diastereomer 2 | 0.15 Cyclohex/THF (9:1) |
| 292 | 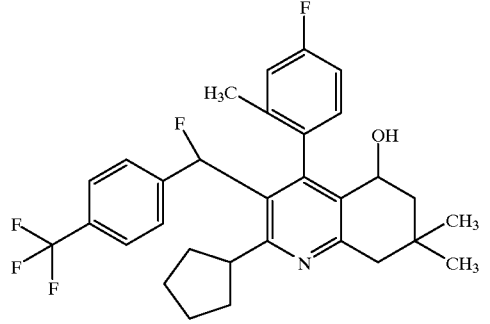 | diastereomer B-2 | 0.18 PE/EA (9:1) |
| 293 | 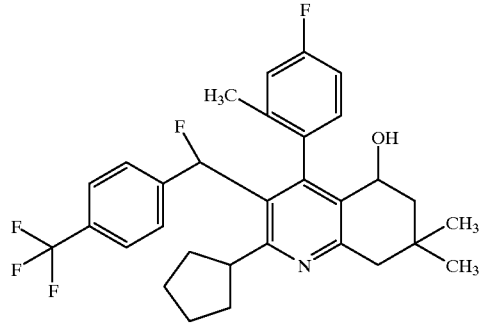 | diastereomer B-1 | 0.25 PE/EA (9:1) |
| 294 | 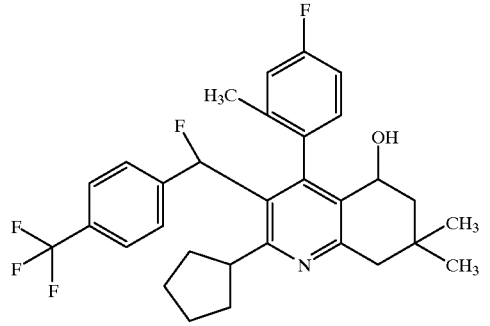 | diastereomer A-½ | 0.26 PE/EA (9:1) |

-continued
| Ex. No. | Structure | Isomer | $R_f$ value |
|---|---|---|---|
| 295 | 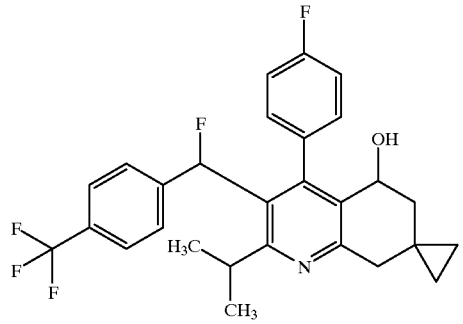 | diastereomer 1 | 0.31 Cyclohex/THF (9:1) |
| 296 | 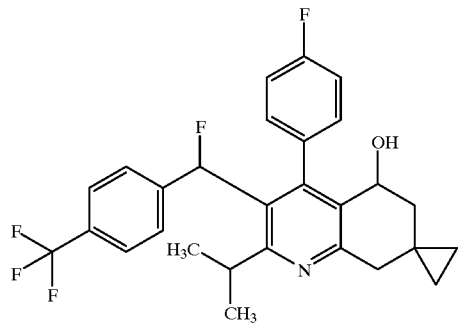 | diastereomer 2 | 0.23 Cyclohex/THF (9:1) |
| 297 | 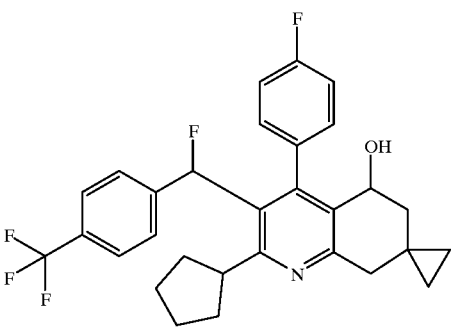 | diastereomer 1 | 0.355 Cyclohex/THF (9:1) |
| 298 | 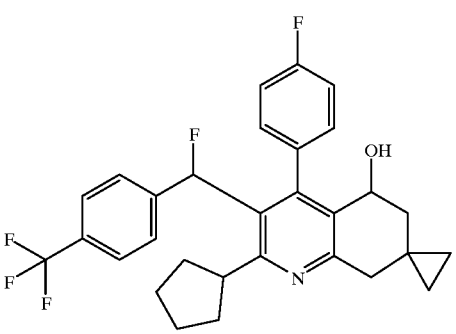 | diastereomer 2 | 0.29 Cyclohex/THF (9:1) |

| Ex. No. | Structure | Isomer | $R_f$ value |
|---|---|---|---|
| 299 | 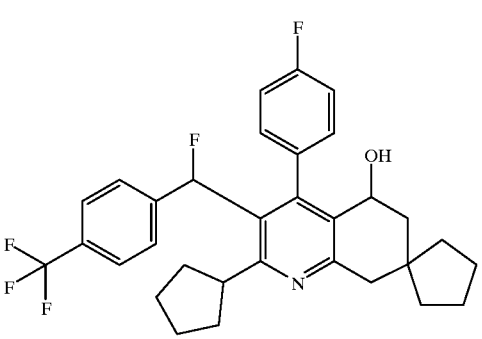 | Enantiomer I from Ex. No. 270 | 0.66 Toluol/EA (9:1) |
| 300 | 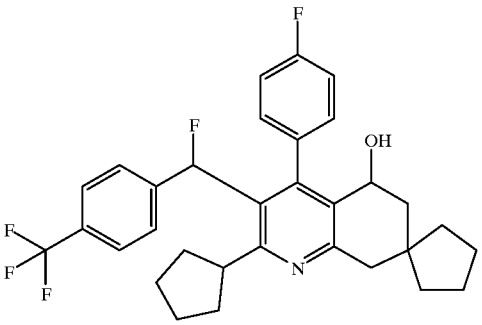 | Enantiomer II from Ex. No. 270 | 0.60 Tol/EA (9:1) |
| 301 | 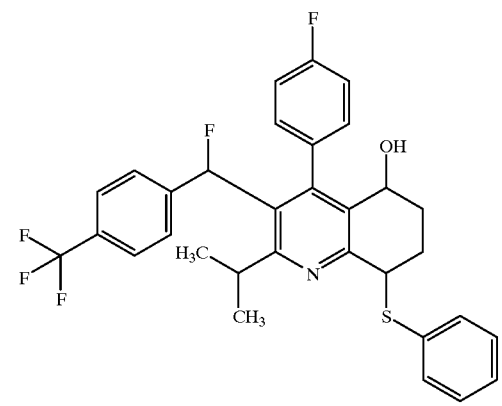 | diastereomer 1 | 0.33 Cy/EA (8:2) |
| 302 | 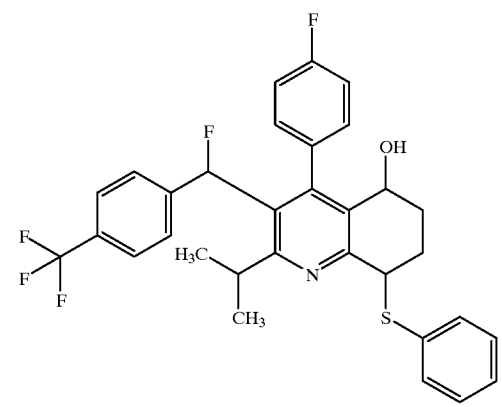 | diastereomer 2 | 0.28 Cy/EA (8:2) |

-continued

| Ex. No. | Structure | Isomer | $R_f$ value |
|---|---|---|---|
| 303 | 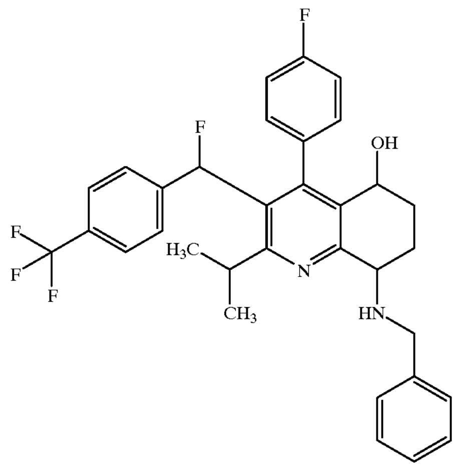 | diastereomer 2 | 0.25 EA |
| 304 | 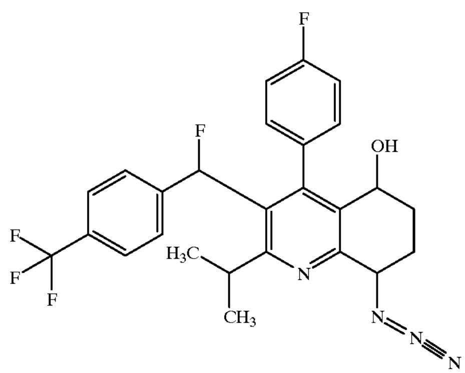 | diastereomer 3 | 0.2 Cy/EA (8:2) |
| 305 | 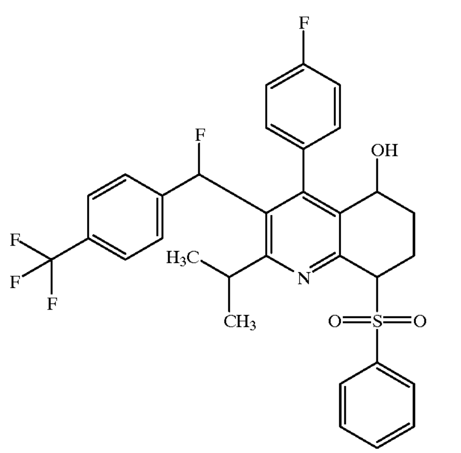 | diastereomer mixture | 0.37 Cy/EA (8:2) |

-continued
| Ex. No. | Structure | Isomer | $R_f$ value |
|---|---|---|---|
| 306 | 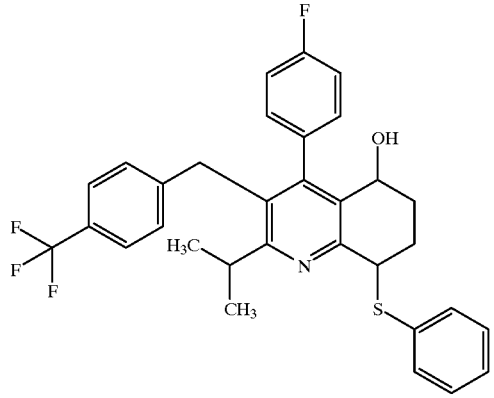 | Racemate | 0.25 Cy/EA (8:2) |
| 307 | 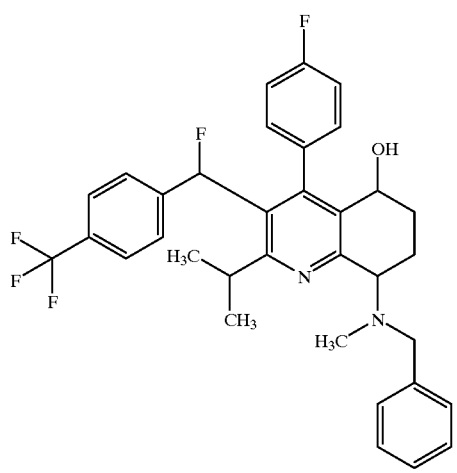 | diastereomer 2 | 0.2 Cy/EA (6:4) |
| 308 | 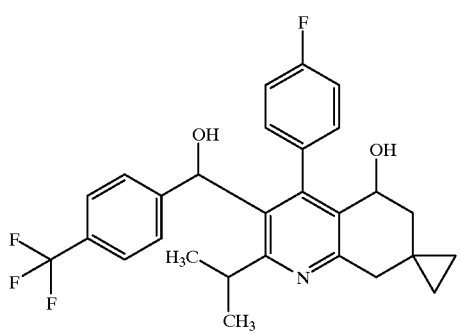 | diastereomer 2 | 0.56 Cyclohex/THF (7:3) |
| 309 | 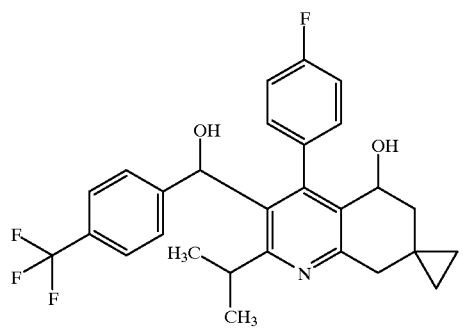 | diastereomer 1 | 0.43 Cyclohex/THF (7:3) |

| Ex. No. | Structure | Isomer | $R_f$ value |
|---|---|---|---|
| 310 | 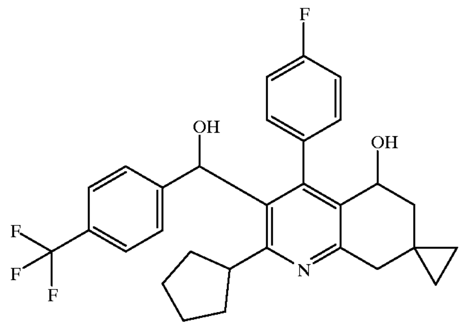 | diastereomer 1 | 0.485 Cyclohex/THF (7:3) |
| 311 | 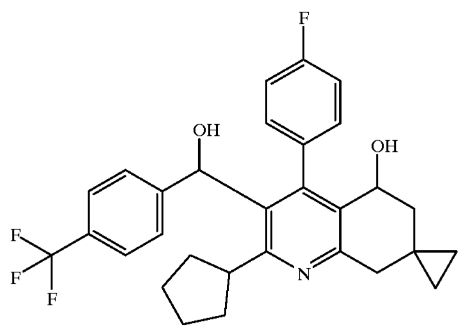 | diastereomer 2 | 0.60 Cyclohex/THF (7:3) |
| 312 | 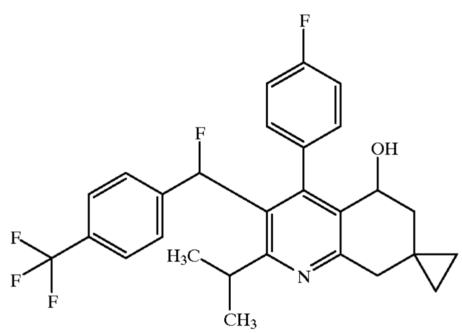 | Enantiomer I from Ex. No. 296 | 0.29 Cyclohex/THF (7:3) |
| 313 | 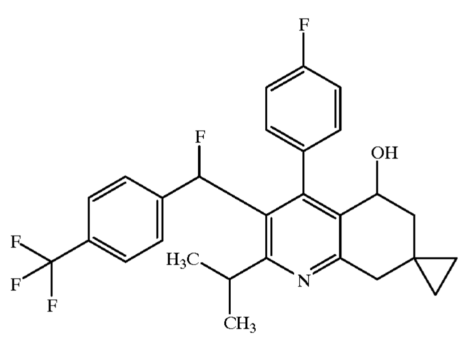 | Enantiomer II from Ex. No. 296 | 0.25 Cyclohex/THF (9:1) |

-continued

| Ex. No. | Structure | Isomer | $R_f$ value |
|---|---|---|---|
| 314 | 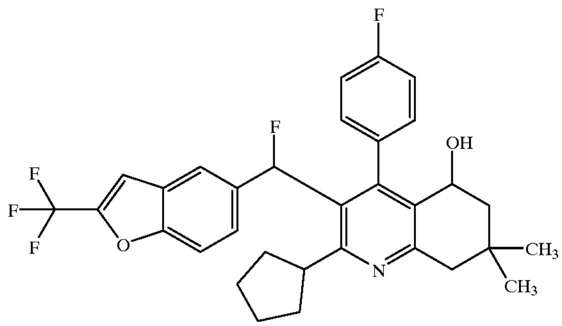 | diastereomer 1 | 0.57 Tol/EA (9:1) |
| 315 | 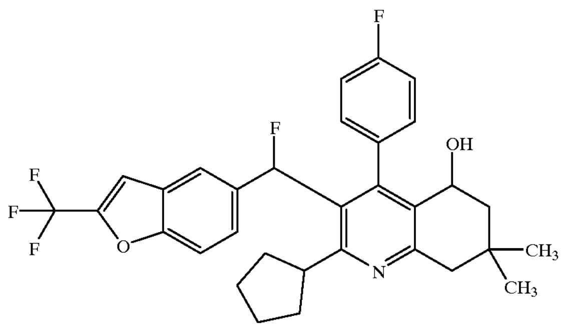 | diastereomer 2 | 0.59 Tol/EA (9:1) |
| 316 | 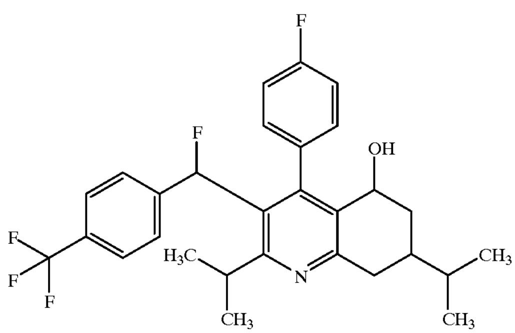 | Enantiomer I from Ex. No. 289 | 0.75 Tol/EA (9:1) |
| 317 | 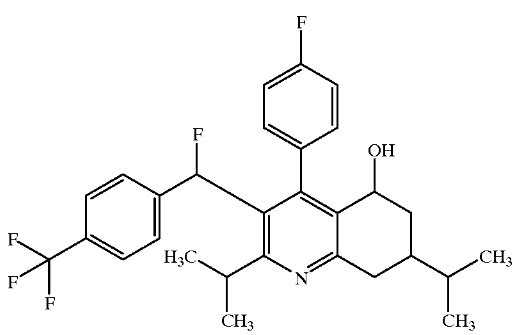 | Enantiomer II from Ex. No. 289 | 0.60 Tol/EA (9:1) |

-continued
| Ex. No. | Structure | Isomer | $R_f$ value |
|---|---|---|---|
| 318 | 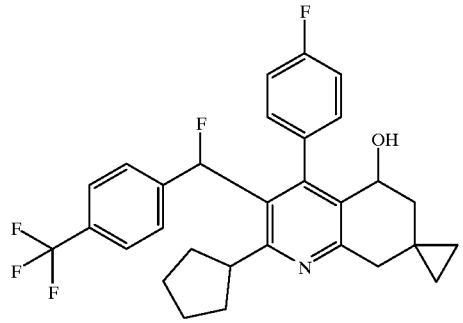 | Enantiomer I from Ex. No. 298 | 0.33 Cyclohex/THF (9:1) |
| 319 | 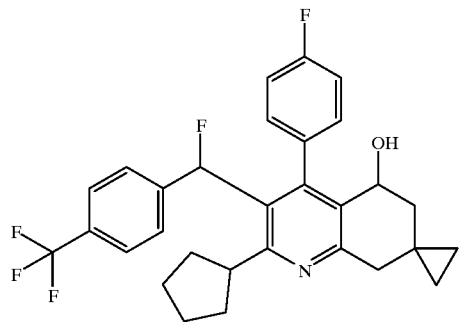 | Enantiomer II from Ex. No. 298 | 0.29 Cyclohex/THF (9:1) |
| 320 | 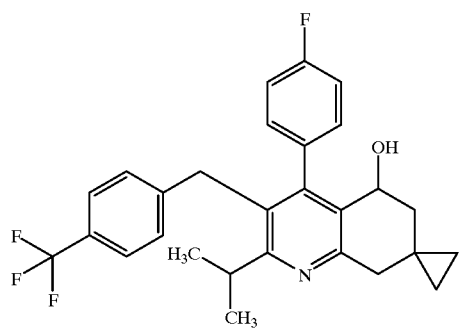 | Isomer from Ex. No. 295 | 0.45 Tol/EA (9:1) |
| 321 | 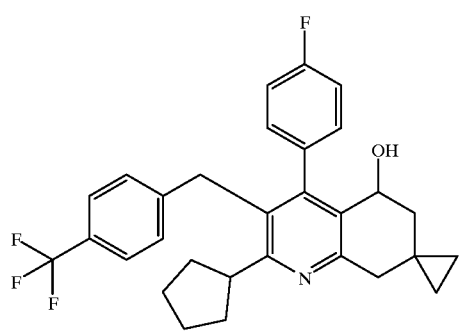 | Isomer from Ex. No. 297 | 0.53 Tol/EA (9:1) |

-continued

| Ex. No. | Structure | Isomer | $R_f$ value |
|---|---|---|---|
| 322 | 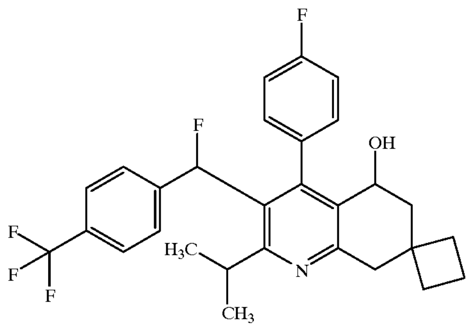 | diastereomer A | Lichrosorb Si60:4.89 n-heptane:Ethanol (99.4/0.6) |
| 323 | 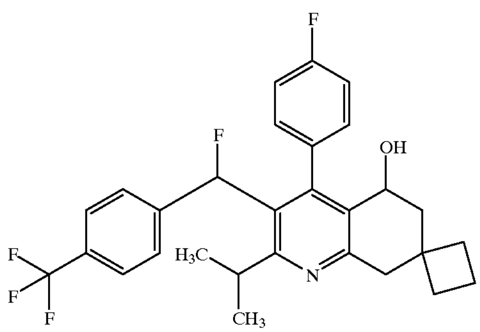 | diastereomer B | Lichrosorb Si60:5.106 n-Heptane:Ethanol (99.4/0.6) |
| 324 | 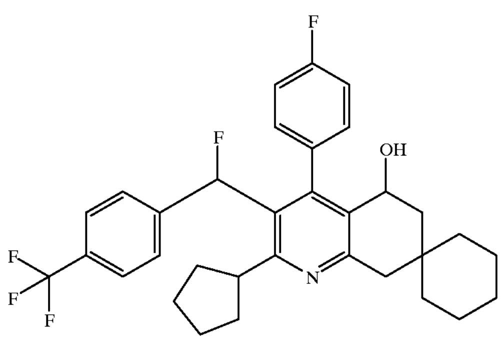 | diastereomer A | Lichrosorb Si60:5.877 n-Heptane:Ethanol (99.7/0.3) |
| 325 | 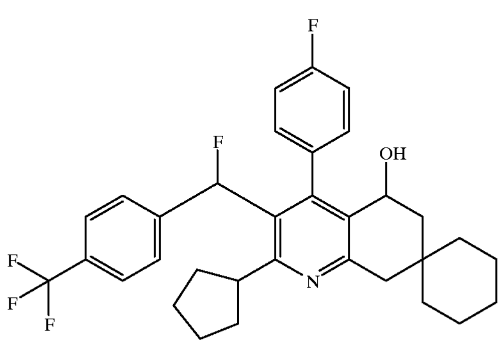 | diastereomer B | Lichrosorb n-Heptane:Ethanol (99.7/0.3) |

-continued
| Ex. No. | Structure | Isomer | $R_f$ value |
|---|---|---|---|
| 326 | 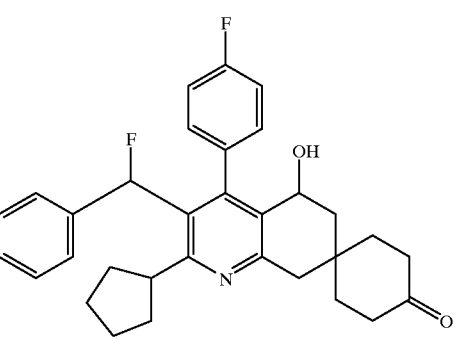 | diastereomer A | 0.15<br>Tol/EA<br>(9:1) |
| 327 | 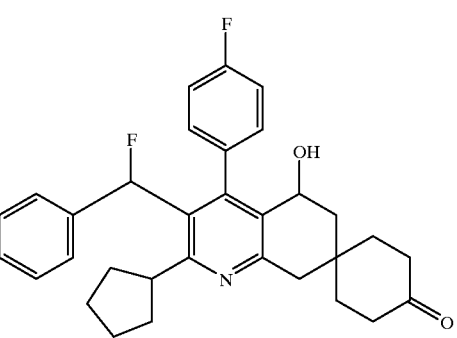 | diastereomer B | 0.35<br>Cyclohex/THF<br>(7:3) |
| 328 | 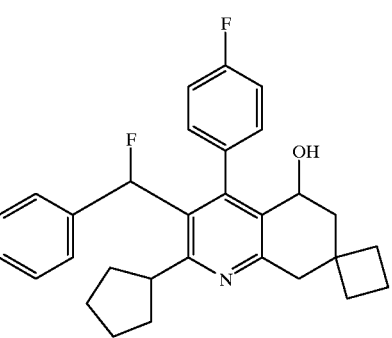 | Enantiomer B1 | Chiral<br>AD:8.096<br>n-Heptane:2-Propanol<br>(98.5/1.5) |
| 329 | 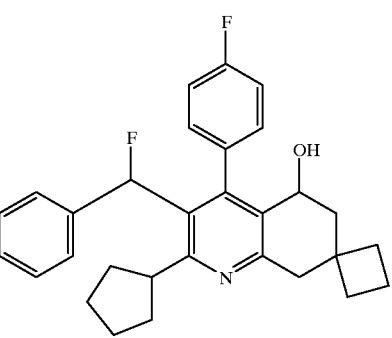 | Enantiomer B2 | Chiral<br>AD:10.037<br>n-Heptane:2-Propanol<br>(98.5/1.5) |

-continued

| Ex. No. | Structure | Isomer | $R_f$ value |
|---|---|---|---|
| 330 | 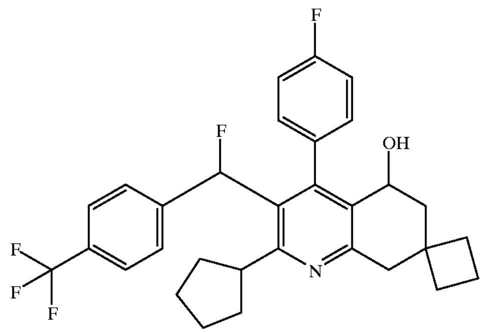 | diastereomer A | Lichrosorb Si60:6.780 n-Heptane:Diethyl ether (90/10) |
| 331 | 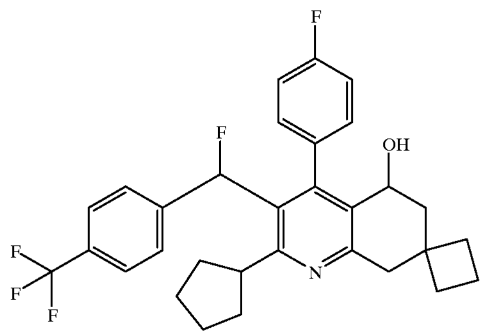 | diastereomer B | Lichrosorb Si100:12.655 n-Heptane:Ethanol (97:3) |
| 332 | 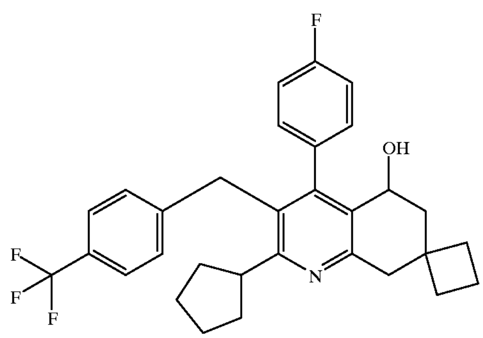 | Racemate | 0.58 Tol/EA (9:1) |
| 333 | 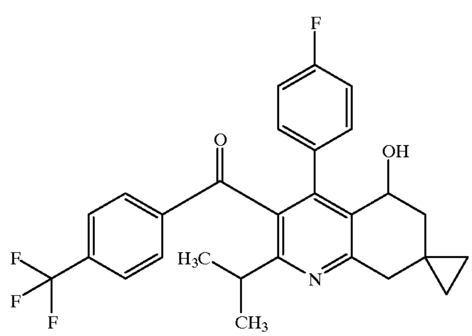 | R,S-Isomer | 0.34 Tol/EA (9:1) |

-continued

| Ex. No. | Structure | Isomer | $R_f$ value |
|---|---|---|---|
| 334 | 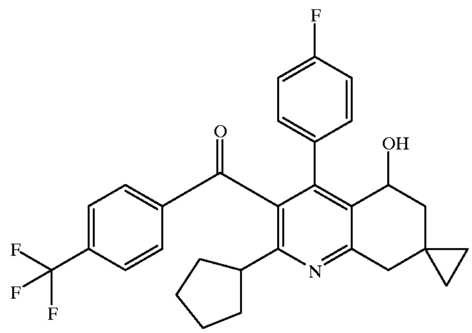 | R,S-Isomer | 0.42 Tol/EA (9:1) |
| 335 | 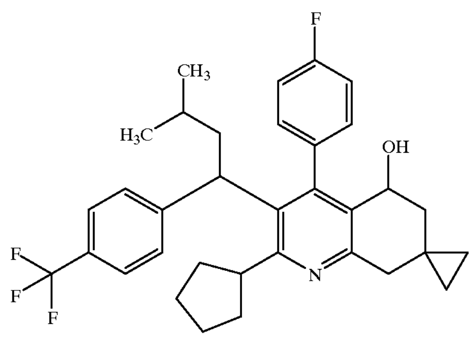 | Isomer 1 | 0.56 Tol/EA (9:1) |
| 336 | 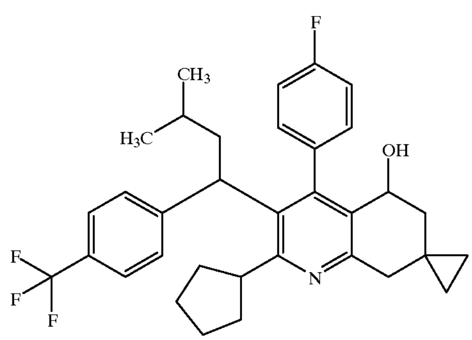 | Isomer 2 | 0.6 Tol/EA (9:1) |
| 337 | 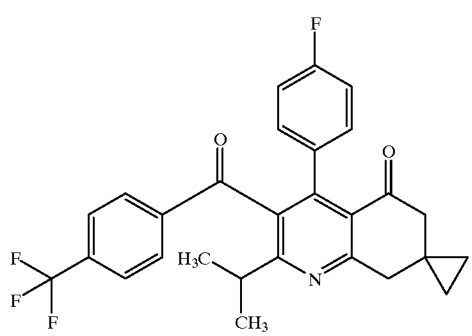 | | 0.42 Tol/EA (9:1) |

-continued

| Ex. No. | Structure | Isomer | $R_f$ value |
|---|---|---|---|
| 338 | 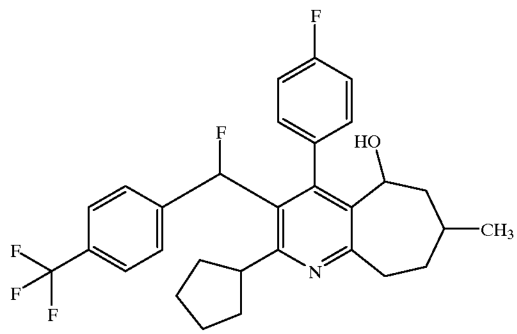 | Mixture of diastereomeres RS | 0.36 Cy/EA 8:2 |
| 339 | 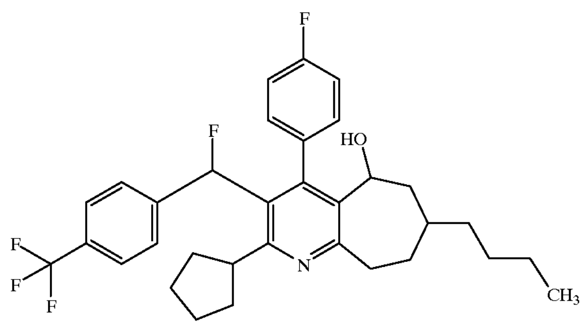 | Mixture of diastereomers RS | 0.45 CY/EA 8:2 |
| 340 | 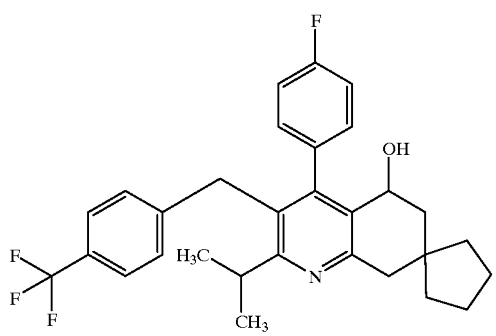 | | 0.57 Tol/EA (9:1) |
| 341 | 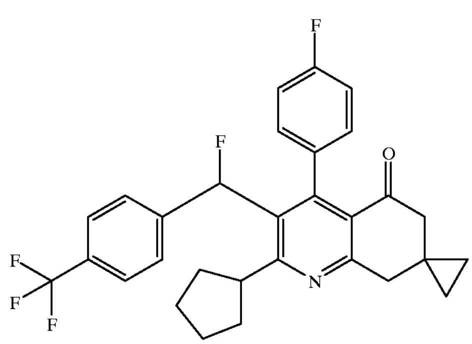 | Enantiomer 1 | 0.33 Cyclohex/EA (9:1) |

| Ex. No. | Structure | Isomer | $R_f$ value |
| --- | --- | --- | --- |
| 342 | 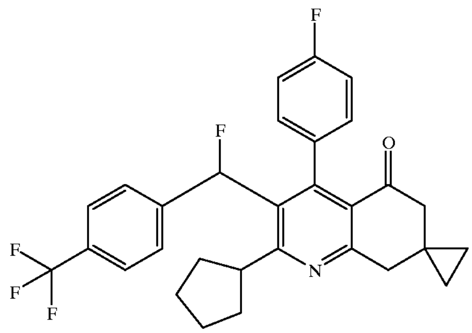 | Enantiomer 2 | 0.36 Cyclohex/EA (9:1) |
| 343 | 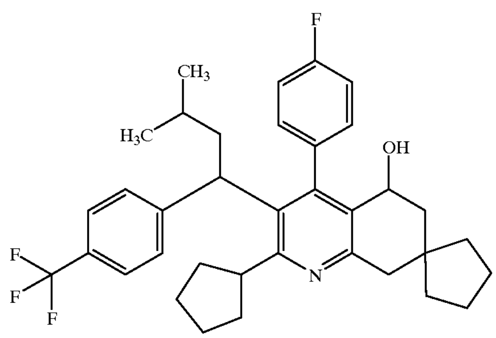 | Isomerengemisch | 0.69 Tol/EA (9:1) |
| 344 | 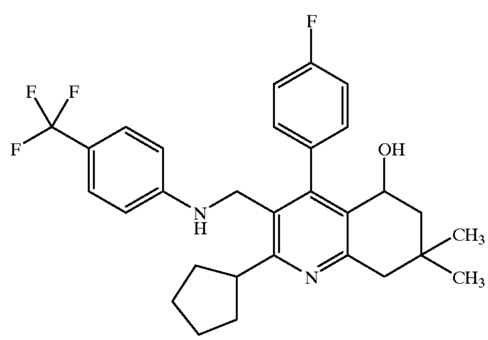 | | |
| 345 | 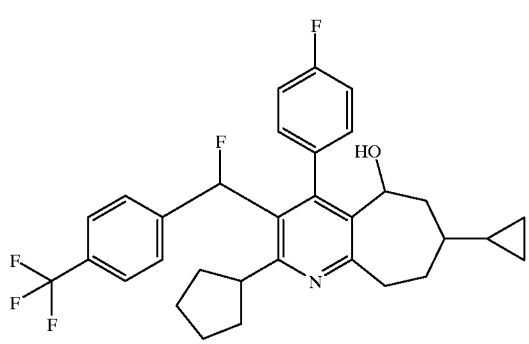 | Mixture of diastereomers RS | 0.20 Cy/EA (9:1) |

-continued

| Ex. No. | Structure | Isomer | $R_f$ value |
|---|---|---|---|
| 346 | 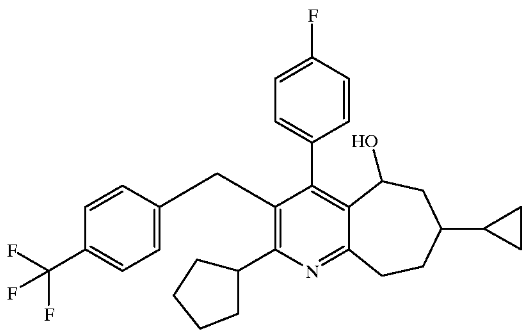 | Mixture of diastereomers RS | 0.38 Cy:EA (8:2) |
| 347 | 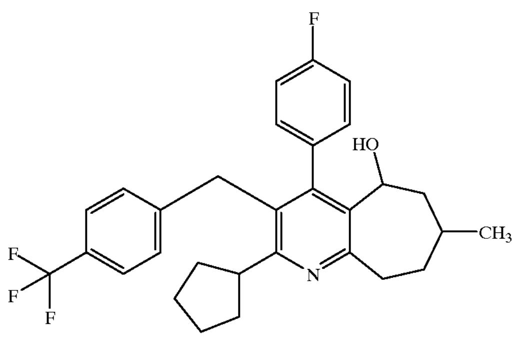 | Mixture of diastereomers RS | 0.18 Cy/EA (9:1) |
| 348 | 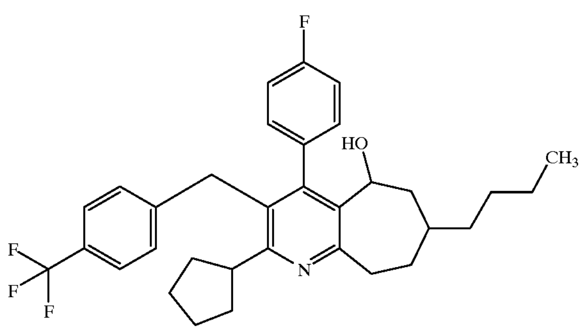 | Mixture of diastereomers RS | 0.19 Cy/EA (9:1) |
| 349 | 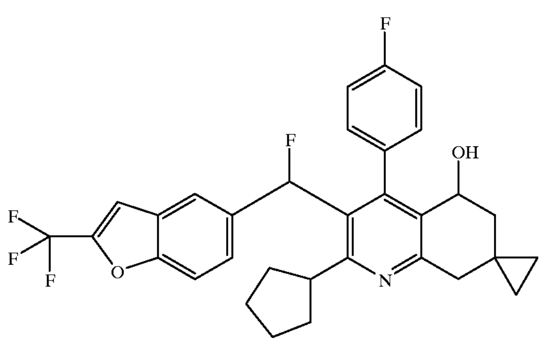 | diastereomer A | Lichrosorb Si60:4.641 n-Heptane:ethyl ether (80/20) |

-continued

| Ex. No. | Structure | Isomer | $R_f$ value |
|---|---|---|---|
| 350 | 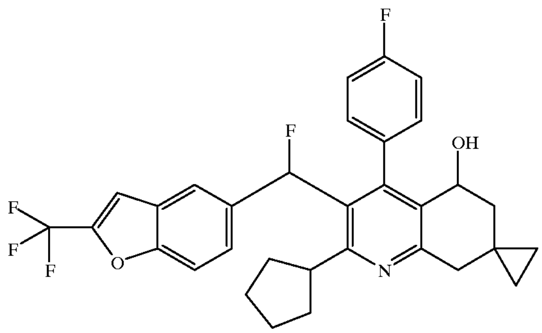 | diastereomer B | Lichrosorb Si60:5.363 n-Heptane:Ethyl ether (80/20) |
| 351 | 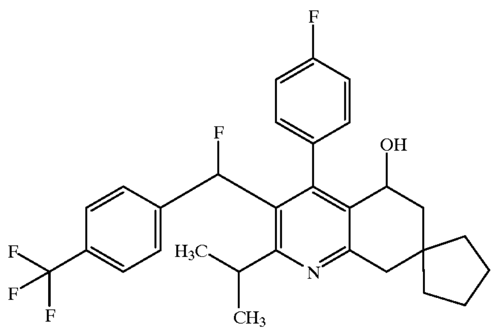 | Enantiomer A | Chiralpak AD:15.76 n-Heptane:2-Propanol (99/1) |
| 352 | 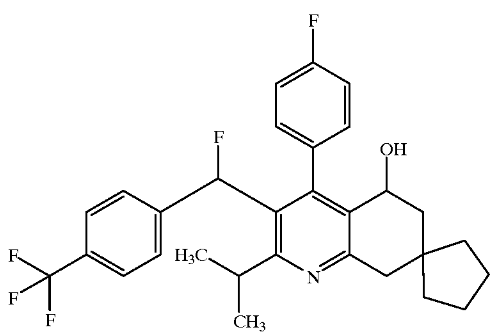 | Enantiomer B | Chiralpak AD:25.57 n-Heptane:2-Propanol (99/1) |
| 353 | 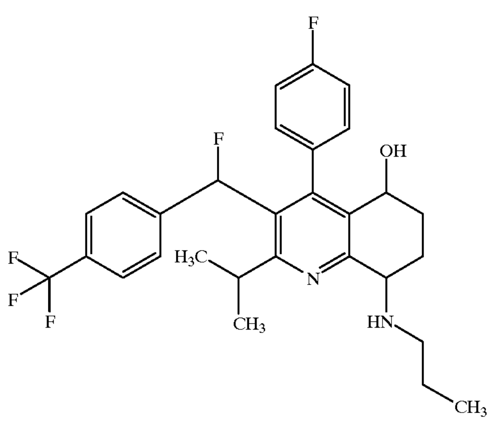 | | 0.17 EA:EtOH (9:1) |

-continued

| Ex. No. | Structure | Isomer | R$_f$ value |
|---|---|---|---|
| 354 | 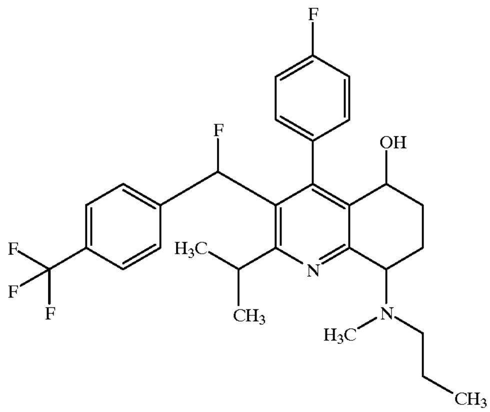 | | 0.18 EA:EtOH (9:1) |
| 355 | 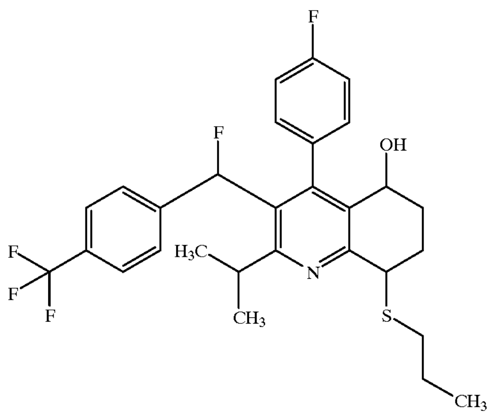 | | 0.39 Cy:EA (8:2) |
| 356 | 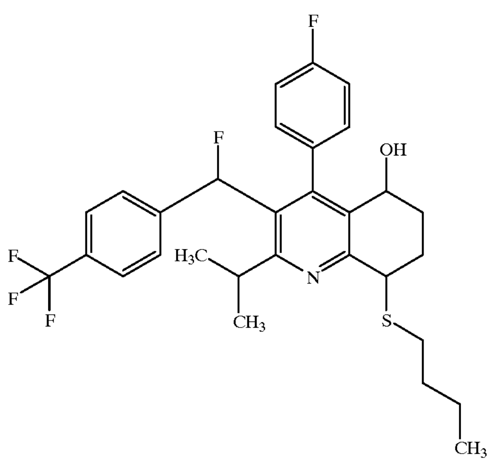 | | 0.42 Cy:EA (8:2) |

-continued

| Ex. No. | Structure | Isomer | $R_f$ value |
|---|---|---|---|
| 357 | 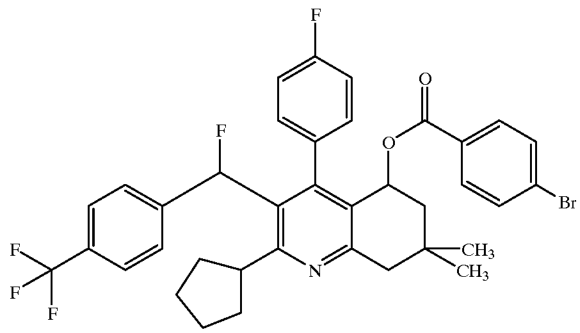 | | 0.94<br>Cyclohex/EA<br>(8.5:1.5) |
| 358 | 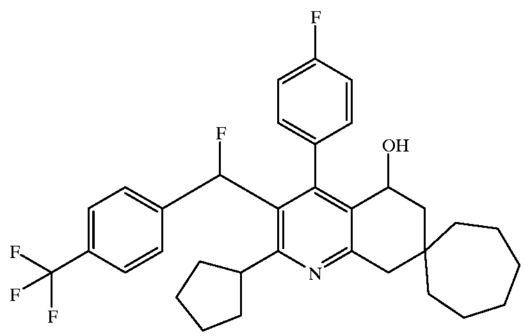 | diastereomer B | Lichrosorb<br>Si60:1.737<br>n-Heptane:Ethanol<br>(98.5/1.5) |
| 359 | 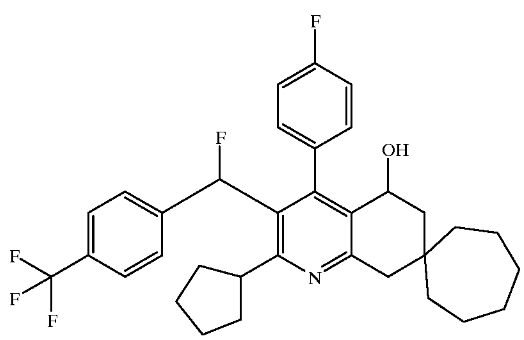 | diastereomer A | Lichrosorb<br>Si60:2.443<br>n-Heptane:Ethanol<br>(98:2) |
| 360 | 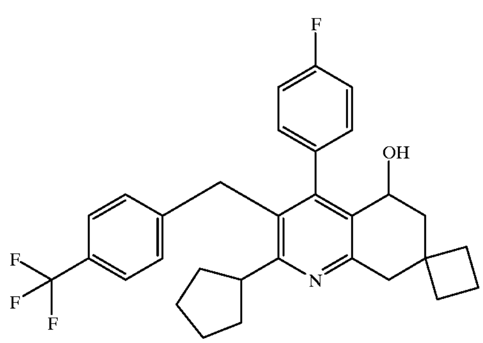 | Enantiomer 1 | Chiracel<br>AD:6.212<br>n-Heptane:2-propanol<br>(98/2) |

-continued

| Ex. No. | Structure | Isomer | R_f value |
|---|---|---|---|
| 361 | 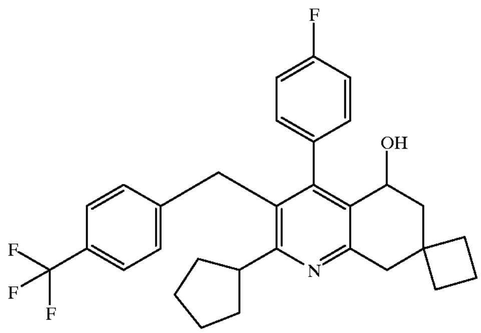 | Enantiomer 2 | Chiracel AD:7.062 n-Heptane:2-Propanol (98/2) |
| 362 | 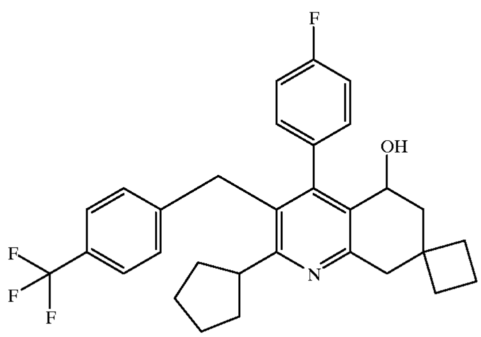 | Racemate | Gromsil ODSB:6.232 0.01 m $H_3PO_4$ 10% Acetonitrile (Gradient) |
| 363 | 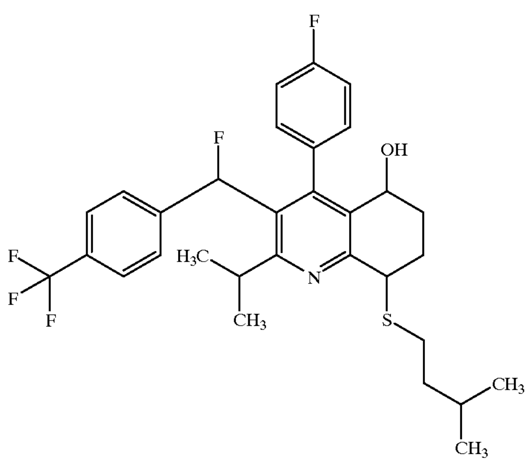 | | 0.42 Cy:EA (8:2) |

| Ex. No. | Structure | Isomer | $R_f$ value |
|---|---|---|---|
| 364 | 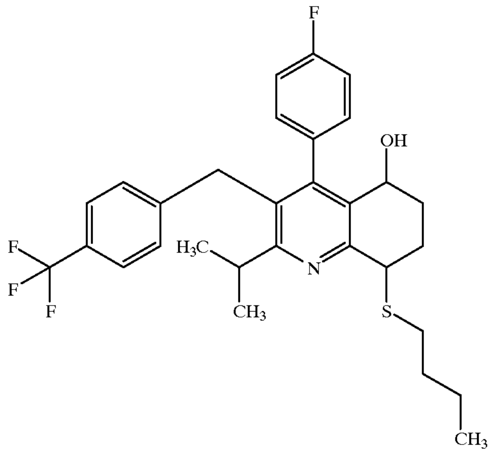 | | 0.25 CH$_2$Cl$_2$ |
| 365 | 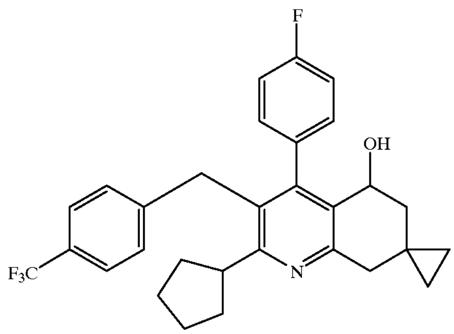 | | Lichrosorb Si60:7.00 n-Heptane:diethyl ether (85/15) |
| 366 | 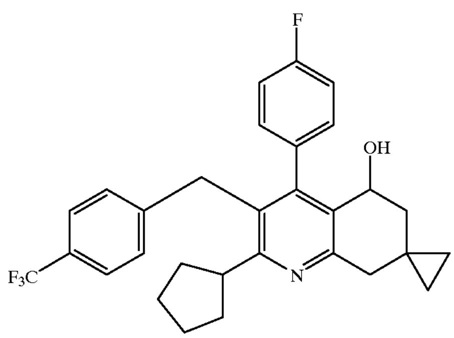 | | Lichrosorb Si60:6.858 n-heptane:Diethyl ether (85/15) |
Example 367
2-Cyclopentyl-4-(4-fluorophenyl)-7,7-dimethyl-3-(4-trifluoromethylbenzoyl)-7,8-dihydro-6H-quinolin-5-one
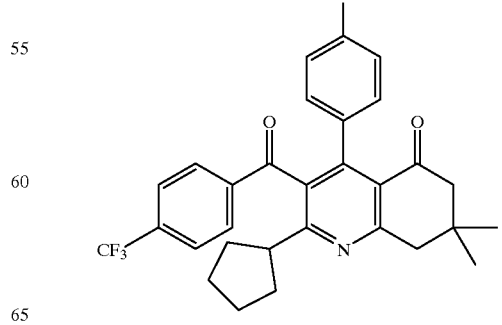

843 g of 2-cyclopentyl-4-(4-fluorophenyl)-7,7-dimethyl-3-(4-trifluoromethylbenzoyl)-4,6,7,8-tetrahydro-1H-quinolin-5-one were oxidized to the pyridine at room temperature in the course of one hour using 7021.3 g of manganese dioxide (activated) in 28 liters of methylene chloride. After separating off the manganese dioxide and distilling off the methylene chloride, the residue was recrystallized from petroleum ether. 618 g of crystals having a purity of 99.3% according to HPLC resulted. By chromatography on silica gel, it was possible to obtain from the mother liquor of the crystallization, using toluene/ethyl acetate 4:1, a further 168 g of the same quality.

TLC: $R_f$=0.8 (toluene/ethyl acetate 4:1)

Melting point: 186° C.

Example 368

[2-Cyclopentyl-4-(4-fluorophenyl)-5-hydroxy-7,7-dimethyl-5,6,7,8-tetrahydroquinolin-3-yl]-(4-trifluoromethylphenyl)-methanone

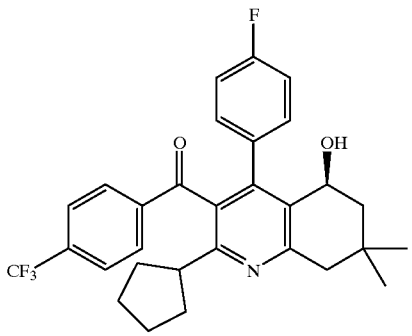

625.3 g of 2-cyclopentyl-4-(4-fluorophenyl)-7,7-dimethyl-3-(4-trifluoromethylbenzoyl)-7,8-dihydro-6H-quinolin-5-one were reduced at 0° to −5° C. in 6 liters of tetrahydrofuran using 56.4 g of IR,2S-aminoindanol and 800 g of boranediethylaniline complex. Quenching of the reaction was carried out after approximately 20 hours using 500 ml of 1,2-ethanediol. The tetrahydrofuran was distilled off, the resulting oil was taken up in ethyl acetate and the organic phase was dried and concentrated after washing with 2 N hydrochloric acid and saturated sodium hydrogen carbonate solution. The residue was recrystallized hot from cyclohexane. A total of 574 g of colorless crystals having a purity of 99.4% according to HPLC (e.e. 97.4%) resulted.

Melting point: 114° C.

TLC: $R_f$=0.2 (petroleum ether/ethyl acetate 9:1)

Example 369

[5-(tert-Butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone

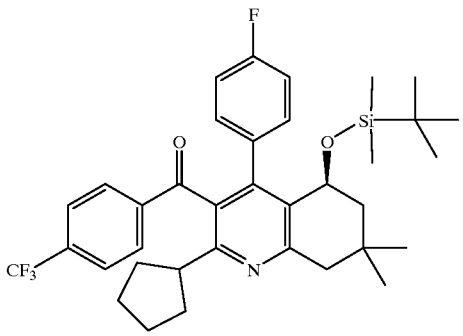

a) 574 g of [2-cyclopentyl-4-(4-fluorophenyl)-5-hydroxy-7,7-dimethyl-5,6,7,8-tetrahydroquinolin-3-yl]-(4-trifluoromethylphenyl)-methanone and 522 ml of lutidine dissolved in 5.4 liters of toluene were reacted at −5° C. to room temperature with a mixture of 593.2 g of tert-butyldimethylsilyl trifluoromethanesulphonate and 1 liter of toluene in the course of 2.5 hours. The reaction was quenched with 10% strength aqueous ammonium chloride solution, and the organic phase was washed with 0.1 N hydrochloric acid and saturated aqueous sodium hydrogencarbonate solution and dried. After distilling off the solvent in vacuo, the residue was recrystallized from ethanol. A total of 633 g of colorless crystals having a purity of 99.2% according to HPLC (e.e. 98.7%) resulted.
Melting point: 108° C.
TLC: $R_f$=0.8 (petroleum ether/ethyl acetate 9:1)
b) 320 mg of manganese dioxide (Merck Order No. 805958, 90%, precipitated, active) were added in portions to 50 mg of syn- and 50 mg of anti-[5-(tert-butyldimethylsilanyloxy-2-cyclopentyl-4-(4-fluorophenyl)-7,7-dimethyl-5,6,7, 8-tetrahydroquinolin-3-yl]-(4-trifluoro-methylphenyl)-methanol dissolved in 2 ml of dichloromethane and the mixture was stirred for 7 h. The solvent was removed in vacuo and the residue was applied directly to a flash silica gel column. Chromatography using petroleum ether/ethyl acetate 15:1 afforded 93 mg of the product.
TLC: $R_f$=0.6 (petroleum ether/ethyl acetate 9:1)

Example 370

[5-(tert-Butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol

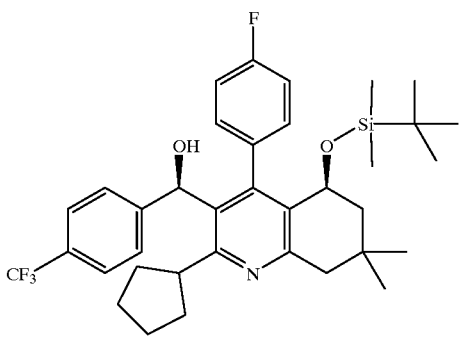

16.5 ml of sodium bis-(2-methoxyethoxy)-dihydroaluminate solution (65% strength in toluene) were added dropwise to 9 g of [5-(tert-butyldimethylsilanyloxy)-

2-cyclopentyl-4(4-fluorophenyl)-7,7-dimethyl-5,6,7,8tetrahydroquinolin-3-yl]-4-trifluoromethylphenyl)-methanone dissolved in 60 ml of toluene. The reaction was quenched after 3.5 hours using methanol, the mixture was extracted with ethyl acetate and the organic phase was washed with potassium sodium tartrate solution and saturated aqueous sodium hydrogencarbonate solution and dried. After distilling off the solvent in vacuo, the residue was recrystallized from petroleum ether. A total of 4.8 g of colorless crystals having a purity of 99.4% according to HPLC (e.e. 99.0%) resulted. By chromatography on silica gel, it was possible to obtain from the mother liquor of the crystallization, using petroleum ether/ethyl acetate 9:1, a further 1.8 g of the same quality.

Melting point: 142° C.

TLC: $R_f$=0.5 (petroleum ether/ethyl acetate 9:1)

Example 371

5-(tert-Butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline

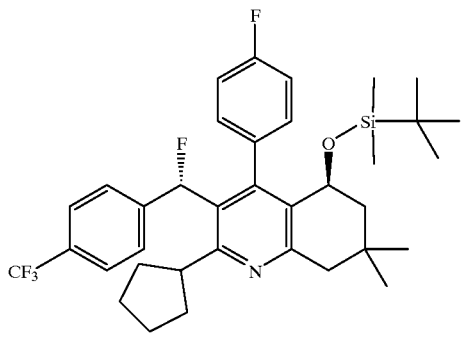

1.46 g of diethylaminosulphur trifluoride dissolved in 10 ml of toluene were added dropwise at −5° C. to 3.8 g of [5-(tert-butyldimethylsilanyloxy)-2-cyclopentyl-4-(4-fluorophenyl)-7,7-dimethyl-5,6,7, 8-tetrahydroquinolin-3-yl]-(4-trifluoromethylphenyl)-methanol dissolved in 37.8 ml of toluene. The reaction was quenched after 30 minutes using saturated aqueous sodium hydrogencarbonate solution and the organic phase was washed again using saturated aqueous sodium hydrogencarbonate solution and dried. After distilling off the solvent in vacuo, the residue was recrystallized from ethanol. A total of 3.33 g of colorless crystals having a purity of 99.4% according to HPLC resulted. By chromatography on silica gel, it was possible from the mother liquor of the crystallization, using petroleum ether/ethyl acetate 10:1, to obtain a further 0.26 g of the same quality.

Melting point: 128° C.

TLC: $R_f$=0.8 (petroleum ether/ethyl acetate 9:1)

Example 372

[-5-(tert-Butyldimethylsilanyloxy)-2-cyclopentyl-4-(4-fluorophenyl)-3-[fluoro-(4-trifluoro-methylphenyl)-methyl]-7,7-dimethyl-5,6,7,8-tetrahydroquinoline

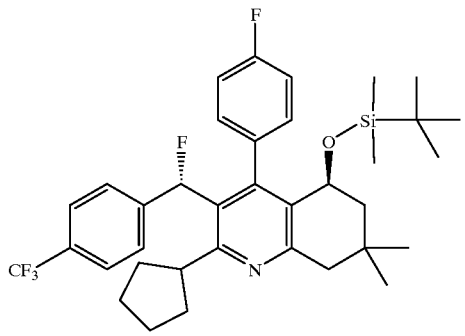

2 g of [5-(tert-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol and 2.14 ml of N,N-diethyl-1,1,2,3,3,3-hexafluoropropylamine were stirred at 60° C. under argon in 25 ml of toluene for 18 hours. Working up was carried out by pouring into saturated sodium hydrogencarbonate solution, separating off the organic phase, fresh extraction with saturated sodium hydrogencarbonate solution, drying and concentration in vacuo. The residue was recrystallized from hot ethanol and after drying yielded 1.3 g of colorless crystals having a purity of 99.4% according to HPLC. By chromatography on silica gel, it was possible from the mother liquor of the crystallization, using petroleum ether/ethyl acetate 10:1, to obtain a further 0.3 g of the same quality.

Example 373

2-Cyclopentyl-4-(4-fluorophenyl)-3-[fluoro-(4-trifluoromethylphenyl)-methyl]-7,7-dimethyl-5,6,7,8-tetrahydroquinolin-5-ol

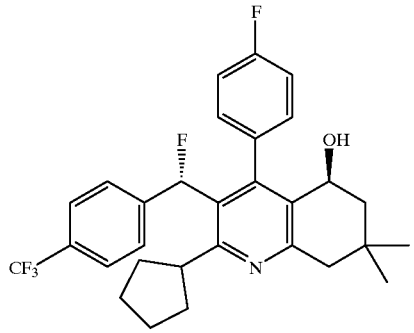

110 g of 5-(tert-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline were stirred at 40° C. for 2 hours in a mixture of 913 ml of 5 N hydrochloric acid, 1364 ml of methanol and 902 ml of tetrahydrofuran. Working up was carried out by pouring into saturated aqueous sodium hydrogencarbonate solution and extraction with ethyl acetate. The organic phases were dried after fresh washing with saturated aqueous sodium hydrogencarbonate solution. After distilling off the solvent in vacuo, the residue was recrystallized from cyclohexane. After drying in an oil-pump vacuum, a total of 71.1 g of colorless crystals having a purity of 99.4% according to HPLC (e.e. 99.5%) resulted. By chromatography on silica gel, it was possible from the mother liquor of the crystallization, using petroleum ether/ethyl acetate 7:1, to obtain a further 10.8 g of the same quality.

Melting point: 140° C.
TLC: $R_f$=0.2 (petroleum ether/ethyl acetate 9:1)

Example 374

S,S-Enantiomer (EN B I)

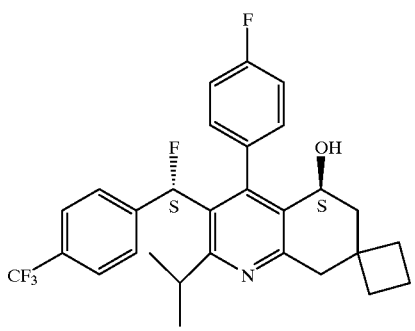

(5'S)-2'-(1-methyl-ethyl)-4'-(4-fluoro-phenyl)-3'-[(S)-fluoro-(4-trifluoromethyl-phenyl)-methyl]-5',8'-dihydro-6'H-spiro [cyclobutane-1,7'-quinolin]-5'-ol
$C_{29}H_{28}F_5NO$ (501.5)

Example 375

R,R-Enantiomer (EN B II)

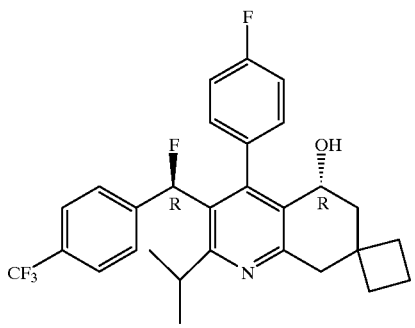

(5'R)-2'-(1-methyl-ethyl)-4'-(4-fluoro-phenyl)-3'-[(R)-fluoro-(4-trifluoromethyl-phenyl)-methyl]-5',8'-dihydro-6'H-spiro[cyclobutane-1,7'-quinolin]-5'-ol
$C_{29}H_{28}F_5NO$ (501.5)

Example 376

R,S-Enantiomer (EN A I)

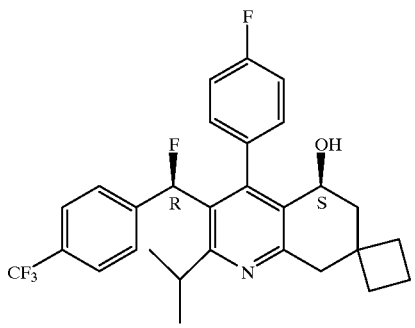

(5'S)-2'-(1-methyl-ethyl)-4'-(4-fluoro-phenyl)-3'-[(R)-fluoro-(4-trifluoromethyl-phenyl)-methyl]-5',8'-dihydro-6'H-spiro[cyclobutane-1,7'-quinolin]-5'-ol
$C_{29}H_{28}F_5NO$ (501.5)

Example 377

S,R-Enantiomer (EN A II)

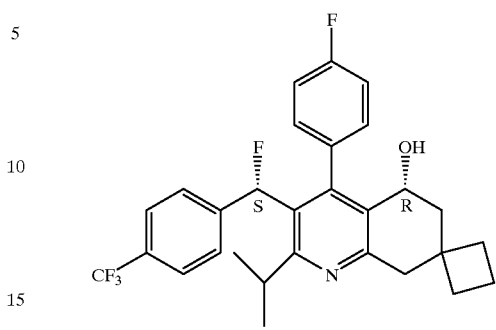

(5'R)-2'-(1-methyl-ethyl)4'-(4-fluoro-phenyl)-3'-[(S)-fluoro-(4-trifluoromethyl-phenyl)-methyl]-5',8'-dihydro-6'H-spiro[cyclobutane-1,7'-quinolin]-5'-ol
$C_{29}H_{28}F_5NO$ (501.5)

Examples 374/375

(Preparative method for the 5,5- and R,R-isomer)

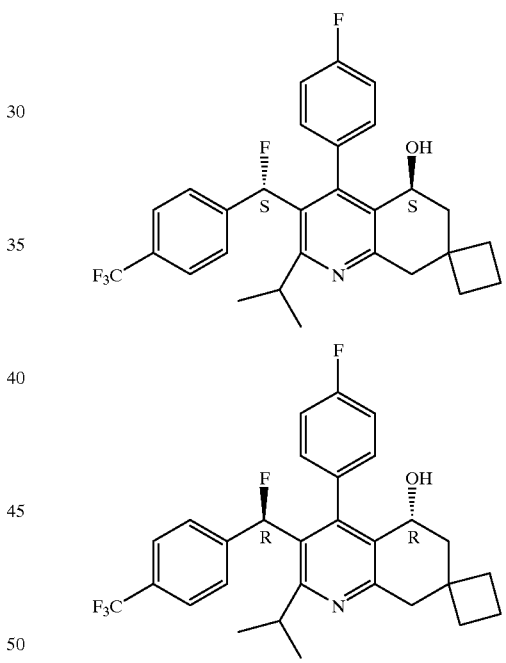

2.23 g (3.62 mmol) of 5'S-(tert.butyl-dimethylsilanyloxy-2'-(1-methyl-ethyl)-4'(4-fluorophenyl)-3'-[(S)-fluoro(4-trifluoromethylphenyl)-methyl]-5',8'-dihydro-6'H-spiro [cyclobutane-1,7'-quinoline] (the Dia B isomer, can be synthesized in analogy to examples I to X starting from 5-Cyclobutylspirocyclohexane-1,3-dione) are stirred—dissolved in 26.5 ml of THF and 36.5 ml of methanol—analogously to Example 1, with 26.5 ml of 6-molar hydrochloric acid for 90 minutes at 60° C. Then 100 ml of a saturated sodium bicarbonate solution and 200 ml of ethyl acetate are added to the reaction solution, the organic phase is separated off and the aqueous phase is extracted two more times with ethyl acetate. The combined organic phases are dried over sodium sulphate and concentrated by evaporation.

Yield: 1.785 g (the racemate)

MS (DCI, NH$_3$): 502 [M+H]+; 100%

The separation of the racemate is carried out in two steel columns (each measuring 300×30 mm) connected in series and packed with a chiral silica gel phase (CSP, see Agnew. Chem. 103 (1991), 1685).

The mobile phase used is a mixture of n-heptane and tetrahydrofuran (9/1; vol/vol) at a flow rate of 25 ml/min. The detection is carried out by UV photometry at 280 nm. 60 mg of product were applied per cycle time of 20 minutes. The S,S enantiomer is eluted first of all, followed by the R,R-enantiomer (Example 375).

The two compounds are then isolated by concentrating the corresponding eluates by evaporation.

For ultrapurification 670 mg of the S,S-enantiomer are chromatographed on 500 ml of silica gel 60 (0.04–0.063 mm) with cyclohexane with the addition of ethyl acetate by the gradient mode. Yield: 591 mg The corresponding R,R-enantiomer is obtained in a yield of 700 mg.

Analytical data:

Example 374

HPLC:rt-10.08, Chiracel AD (250×2 mm) n-heptane 98%/2-propanole 2% flow rate: 0.2 ml/min; 200 nm

Example 375

HPLC:rt-15.14, Chiracel AD (250×2mm) n-heptane 98%/2-propanole 2% flow rate: 0.2 ml/min; 200 nm Examples 376/377

(R,S- and S/R-isomer)

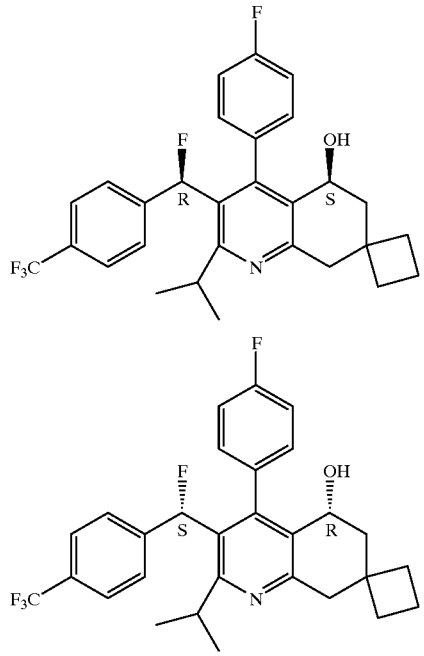

Examples 376/377 were prepared in analogy to examples 374 and 375. Racemic example 322 was separated into its enantiomers by chromatography on chiral phases.

What is claimed is:

1. Cycloalkano-pyridines of the general formula (I)

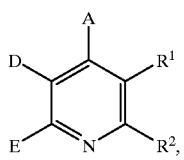

in which

A represents aryl having 6 to 10 carbon atoms, which is optionally substituted up to 5 times in an identical or different manner by halogen, nitro, hydroxyl, trifluoromethyl, trifluoromethoxy, or by straight-chain or branched alkyl, acyl, hydroxyalkyl or alkoxy each having up to 7 carbon atoms, or by a group of the formula —NR$^3$R$^4$, in which
R$^3$ and R$^4$ are identical or different and denote hydrogen, phenyl or straight-chain or branched alkyl having up to 6 carbon atoms, D represents aryl having 6 to 10 carbon atoms, which is optionally substituted by phenyl, nitro, halogen, trifluoromethyl or trifluoromethoxy, or represents a radical of the formula

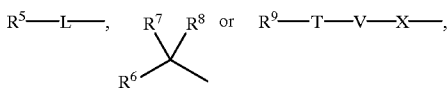

in which
R$^5$ and R$^6$ and R$^9$ independently of one another denote cycloalkyl having 3 to 6 carbon atoms, or denote aryl having 6 to 10 carbon atoms, or a 5- to 7-membered, optionally benzo-fused, saturated or unsaturated, mono-, bi- or tricyclic heterocycle having up to 4 heteroatoms from the series S, N and/or O, where the cycles are substituted, if appropriate, in the case of the nitrogen-containing rings also via the N function, up to 5 times in an identical or different manner by halogen, trifluoromethyl, nitro, hydroxyl, cyano, carboxyl, trifluoromethoxy, straight-chain or branched acyl, alkyl, alkylthio, alkylalkoxy, alkoxy or alkoxycarbonyl each having up to 6 carbon atoms, by aryl- or trifluoromethyl-substituted aryl each having 6 to 10 carbon atoms or by an optionally benzo-fused, aromatic 5- to 7-membered heterocycle having up to 3 heteroatoms from the series S, N and/or O, and/or are substituted by a group of the formula —OR$^{10}$, —SR$^{11}$, —SO$_2$R$^{12}$ or —NR$^{13}$R$^{14}$, in which
R$^{10}$, R$^{11}$ and R$^{12}$ independently of one another denote aryl having 6 to 10 carbon atoms, which for its part is substituted up to 2 times in an identical or different manner by phenyl, halogen or by straight-chain or branched alkyl having up to 6 carbon atoms, R$^{13}$ and R$^{14}$ are identical or different and have the meaning of R$^3$ and R$^4$ indicated above, or $R^5$ and/or $R^6$ denote a radical of the formula

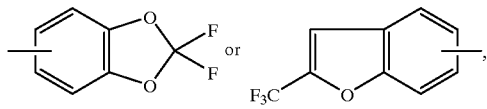

$R^7$ denotes hydrogen or halogen
and
$R^8$ denotes hydrogen, halogen, azido, trifluoromethyl, hydroxyl, trifluoromethoxy, straight-chain or branched alkoxy or alkyl each having up to 6 carbon atoms or a radical of the formula —$NR^{15}R^{16}$,
in which
$R^{15}$ and $R^{16}$ are identical or different and have the meaning of $R^3$ and $R^4$ indicated above,
or
$R^7$ and $R^8$ together form a radical of the formula =O or =$NR^{17}$,
in which
$R^{17}$ denotes hydrogen or straight-chain or branched alkyl, alkoxy or acyl each having up to 6 carbon atoms,
L denotes a straight-chain or branched alkylene or alkenylene chain each having up to 8 carbon atoms, each of which is optionally substituted up to 2 times by hydroxyl,
T and X are identical or different and denote a straight-chain or branched alkylene chain having up to 8 carbon atoms,
or
T or X denotes a bond,
V represents an oxygen or sulphur atom or an —$NR^{18}$ group,
in which
$R^{18}$ denotes hydrogen or straight-chain or branched alkyl having up to 6 carbon atoms or phenyl,
E represents cycloalkyl having 3 to 8 carbon atoms, or represents straight-chain or branched alkyl having up to 8 carbon atoms, which is optionally substituted by cycloalkyl having 3 to 8 carbon atoms or hydroxyl, or represents phenyl which is optionally substituted by halogen or trifluoromethyl,
$R^1$ and $R^2$ together form a straight-chain or branched alkylene chain having up to 7 carbon atoms, which must be substituted by a carbonyl group and/or by a radical of the formula

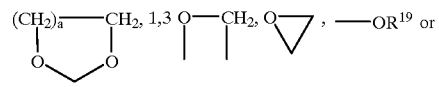

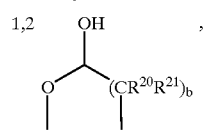

in which
a and b are identical or different and denote a number 1, 2 or 3,
$R^{19}$ denotes hydrogen, cycloalkyl having 3 to 7 carbon atoms, straight-chain or branched silylalkyl having up to 8 carbon atoms or straight-chain or branched alkyl having up to 8 carbon atoms, which is optionally substituted by hydroxyl, straight-chain or branched alkoxy having up to 6 carbon atoms or by phenyl, which for its part can be substituted by halogen, nitro, trifluoromethyl, trifluoromethoxy or by phenyl- or tetrazole-substituted phenyl,
and alkyl is optionally substituted by a group of the formula —$OR^{22}$,
in which
$R^{22}$ denotes straight-chain or branched acyl having up to 4 carbon atoms or benzyl,
or
$R^{19}$ denotes straight-chain or branched acyl having up to 20 carbon atoms or benzoyl which is optionally substituted by halogen, trifluoromethyl, nitro or trifluoromethoxy, or
denotes straight-chain or branched fluoroacyl having up to 8 carbon atoms and 9 fluorine atoms,
$R^{20}$ and $R^{21}$ are identical or different, and denote hydrogen, phenyl or straight-chain or branched alkyl having up to 6 carbon atoms,
or
$R^{20}$ and $R^{21}$ together form a 3 to 6-membered carbocycle,
and, if appropriate also geminally, the carbocycles formed are optionally substituted up to 6 times in an identical or different manner by trifluoromethyl, hydroxyl, halogen, carboxyl, nitro, azido, cyano, cycloalkyl or cycloalkyloxy each having 3 to 7 carbon atoms, by straight-chain or branched alkoxycarbonyl, alkoxy or alkylthio each having up to 6 carbon atoms or by straight-chain or branched alkyl having up to 6 carbon atoms, which for its part is substituted up to 2 times in an identical or different manner by hydroxyl, benzyloxy, trifluoromethyl, benzoyl, straight-chain or branched alkoxy, oxyacyl or carboxyl each having up to 4 carbon atoms and/or phenyl, which for its part can be substituted by halogen, trifluoromethyl or trifluoromethoxy,
and/or the carbocycles formed, also geminally, are optionally substituted up to 5 times in an identical or different manner by phenyl, benzoyl, thiophenyl or sulphonylbenzyl, which for their part are optionally substituted by halogen, trifluoromethyl, trifluoromethoxy or nitro,
and/or are optionally substituted by a radical of the formula

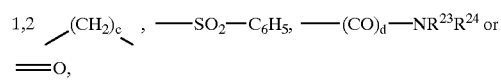

in which
c denotes a number 1, 2, 3 or 4,
d denotes a number 0 or 1,
$R^{23}$ and $R^{24}$ are identical or different and denote hydrogen, cycloalkyl having 3 to 6 carbon atoms, straight-chain or branched alkyl having up to 6 carbon atoms, benzyl or phenyl, which is optionally substituted up to 2 times in an identical or different manner by halogen, trifluoromethyl, cyano, phenyl or nitro,
and/or the carbocycles formed are optionally substituted by a spiro-linked radical of the formula

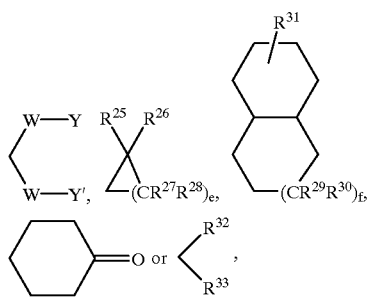

in which
W either denotes an oxygen or a sulphur atom,
Y and Y' together form a 2- to 6-membered straight-chain or branched alkylene chain,
e denotes a number 1, 2, 3, 4, 5, 6 or 7,
f denotes a number 1 or 2,
$R^{25}$, $R^{26}$, $R^{27}$, $R^{28}$, $R^{29}$, $R^{30}$ and $R^{31}$ are identical or different and denote hydrogen, trifluoromethyl, phenyl, halogen or straight-chain or branched alkyl or alkoxy each having up to 6 carbon atoms,
or
$R^{25}$ and $R^{26}$ or $R^{27}$ and $R^{28}$ in each case together form a straight-chain or branched alkyl chain having up to 6 carbon atoms,
or
$R^{25}$ and $R^{26}$ or $R^{27}$ and $R^{28}$ in each case together form a radical of the formula

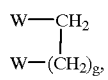

in which
W has the meaning indicated above,
g denotes a number 1, 2, 3, 4, 5, 6 or 7,
$R^{32}$ and $R^{33}$ together form a 3- to 7-membered heterocycle which contains an oxygen or sulphur atom or a group of the formula SO, $SO^2$ or $—NR^{34}$,
in which
$R^{34}$ denotes hydrogen, phenyl, benzyl or straight-chain or branched alkyl having up to 4 carbon atoms,
and their salts and N-oxides, with the exception of 5(6H)-quinolone, 3-benzoyl-7,8-dihydro-2,7,7-trimethyl-4-phenyl.

2. Cycloalkano-pyridines of the formula according to claim 1
in which

A represents naphthyl or phenyl, each of which is optionally substituted up to 2 times in an identical or different manner by fluorine, chlorine, bromine, amino, hydroxyl, trifluoromethyl, trifluoromethoxy or by straight-chain or branched alkyl or alkoxy each having up to 6 carbon atoms, D represents phenyl which is optionally substituted by nitro, fluorine, chlorine, bromine, phenyl, trifluoromethyl or trifluoromethoxy, or represents a radical of the formula

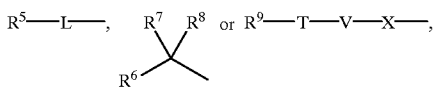

in which
$R^5$, $R^6$ and $R^9$ independently of one another denote cyclopropyl, cyclopentyl or cyclohexyl, or denote phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl, where the cycles are also substituted via the N function, optionally up to 3 times in the case of the nitrogen-containing rings, in an identical or different manner by fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl each having up to 4 carbon atoms, triazolyl, tetrazolyl, benzoxathiazolyl, or trifluoromethyl-substituted phenyl or phenyl, and/or are substitued by a group of the formula $—OR^{10}$, $—SR^{11}$ or $—SO_2R^{12}$,
in which
$R^{10}$, $R^{11}$ and $R^{12}$ are identical or different and denote phenyl, which for its part is substitued up to 2 times in an identical or different manner by phenyl, fluorine, chlorine or by straight-chain or branched alkyl having up to 4 carbon atoms,
$R^5$ and/or $R^6$ denotes a radical of the formula

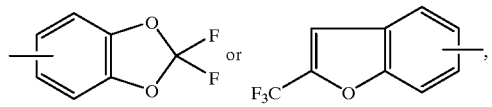

$R^7$ denotes hydrogen, fluorine, chlorine or bromine
and
$R^8$ denotes hydrogen, fluorine, chlorine, bromine, azido, trifluoromethyl, hydroxyl, trifluoromethoxy, straight-chain or branched alkoxy or alkyl having up to 5 carbon atoms in each case or a radical of the formula $—NR^{15}R^{16}$,
in which
$R^{15}$ and $R^{16}$ are identical or different and denote hydrogen, phenyl or straight-chain or branched alkyl having up to 4 carbon atoms,
or
$R^7$ and $R^8$ together form a radical of the formula =O or $=NR^{17}$,
in which
$R^{17}$ denotes hydrogen or straight-chain or branched alkyl, alkoxy or acyl each having up to 4 carbon atoms,
L denotes a straight-chain or branched alkylene or alkenylene chain each having up to 6 carbon atoms, each of which is optionally substituted up to 2 times by hydroxyl,
T and X are identical or different and denote a straight-chain or branched alkylene chain having up to 6 carbon atoms,
or
T or X denotes a bond,
V represents an oxygen or sulphur atom or a group of the formula $—NR^{18}$, in which R$^{18}$ denotes hydrogen or straight-chain or branched alkyl having up to 4 carbon atoms or phenyl, E represents cyclopropyl, -butyl, -pentyl, -hexyl or -heptyl, or represents straight-chain or branched alkyl having up to 6 carbon atoms, which is optionally substituted by cyclopropyl, -butyl, -hexyl, -pentyl, -heptyl or by hydroxyl, or represents phenyl which is optionally substituted by fluorine, chlorine or trifluoromethyl, R$^1$ and R$^2$ together form a straight-chain or branched alkylene chain having up to 6 carbon atoms, which must be substituted by a carboxyl group and/or by a radical of the formula $$(CH_2)_a\!\!-\!\!CH_2,\ 1,3\ O\!\!-\!\!CH_2,\ O\!\!\bigtriangleup,\ -\!\!OR^{19}\ or$$

$$\underset{O}{\overset{1,2\ \ OH}{|}}\underset{|}{(CR^{20}R^{21})_b}\ ,$$

in which a and b are identical or different and denote a number 1, 2 or 3,

R$^{19}$ denotes hydrogen, cyclopropyl, cyclopentyl, cyclohexyl, straight-chain or branched silylalkyl having up to 7 carbon atoms or straight-chain or branched alkyl having up to 6 carbon atoms, which is optionally substituted by hydroxyl, straight-chain or branched alkoxy having up to 4 carbon atoms or by phenyl which for its part can be substituted by fluorine, chlorine, bromine, nitro, trifluoromethyl, trifluoromethoxy or by phenyl- or tetrazole-substituted phenyl, and alkyl is optionally substituted by a group of the formula —OR$^{22}$, in which R$^{22}$ denotes straight-chain or branched acyl having up to 3 carbon atoms or benzyl, or R$^{19}$ denotes straight-chain or branched acyl having up to 18 carbon atoms or benzoyl which is optionally substituted by fluorine, chlorine, bromine, trifluoromethyl, nitro or trifluoromethoxy, or denotes straight-chain or branched fluoroacyl having up to 6 carbon atoms, R$^{20}$ and R$^{21}$ are identical or different, and denote hydrogen, phenyl or straight-chain or branched alkyl having up to 4 carbon atoms, or R$^{20}$ and R$^{21}$ together form a cyclopropyl, cyclobutyl, cyclopentyl, cyclohexyl or cycloheptyl ring, and the carbocycles formed are optionally substituted up to 5 times in an identical or different manner, optionally also geminally, by trifluoromethyl, hydroxyl, carboxyl, azido, fluorine, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio each having up to about 5 carbon atoms or straight-chain or branched alkyl having up to 5 carbon atoms, which for its part is substituted up to 2 times in an identical or different manner by hydroxyl, benzyloxy, benzoyl, straight-chain or branched alkoxy or oxyacyl each having up to 3 carbon atoms, trifluoromethyl and/or phenyl, which for its part can be substituted by fluorine, chlorine, bromine, trifluoromethyl or trifluoromethoxy, and/or the carbocycles formed, also geminally, are optionally substituted up to 4 times in an identical or different manner by phenyl, benzoyl, thiophenyl or sulphonylbenzyl, which for their part are optionally substituted by fluorine, chlorine, bromine, trifluoromethyl, trifluoromethoxy or nitro, and/or are optionally substituted by a radical of the formula $$1,2\ \diagup\!\!(CH_2)_c\!\!\diagdown\ ,\ -\!\!SO_2\!-\!\!C_6H_5,\ -\!\!(CO)_d\!\!-\!\!NR^{23}R^{24}\ or$$

$$=\!\!O,$$

in which c denotes a number 1, 2, 3 or 4, d denotes a number 0 or 1,

R$^{23}$ and R$^{24}$ are identical or different and denote hydrogen, cyclopropyl, cyclobutyl, cyclopentyl, cyclohexyl, straight-chain or branched alkyl having up to 5 carbon atoms, benzyl or phenyl, which is optionally substituted by fluorine, chlorine, bromine, phenyl or trifluoromethyl, and/or the carbocycles formed are optionally substituted by a spiro-linked radical of the formula in which W denotes either an oxygen or a sulphur atom, Y and Y' together form a 2- to 5-membered straight-chain or branched alkyl chain, e denotes a number 1, 2, 3, 4, 5 or 6, f denotes a number 1 or 2, R$^{25}$, R$^{26}$, R$^{27}$, R$^{28}$, R$^{29}$, R$^{30}$ and R$^{31}$ are identical or different and denote hydrogen, trifluoromethyl, phenyl, fluorine, chlorine, bromine or straight-chain or branched alkyl or alkoxy each having up to 5 carbon atoms, or R$^{25}$ and R$^{26}$ or R$^{27}$ and R$^{28}$ in each case together form a straight-chain or branched alkyl chain having up to 5 carbon atoms or R$^{25}$ and R$^{26}$ or R$^{27}$ and R$^{28}$ in each case together form a radical of the formula $$\begin{array}{c} W-CH_2 \\ | \\ W-(CH_2)_g, \end{array}$$

in which

W has the meaning indicated above, g denotes a number 1, 2, 3, 4, 5 or 6, and their salts and N-oxides with the exception of 5(6H)-quinolone, 3-benzoyl-7,8-dihydro-2,7,7-trimethyl-4-phenyl.

3. Cycloalkano-pyridines of the formula according to claim 1 in which

A represents phenyl which is optionally substituted up to 2 times in an identical or different manner by fluorine, chlorine, bromine, hydroxyl, trifluoromethyl, trifluoromethoxy or by straight-chain or branched alkyl or alkoxy each having up to 5 carbon atoms, D represents phenyl which is optionally substituted by nitro, trifluoromethyl, phenyl, fluorine, chlorine or bromine or represents a radical of the formula $$R^5\text{—}L\text{—}, \quad \underset{R^6}{\overset{R^7}{\diagdown}}\!\!\!\diagup\!\!\overset{R^8}{} \quad \text{or} \quad R^9\text{—}T\text{—}V\text{—}X\text{—},$$

in which

R$^5$, R$^6$ and R$^9$ independently of one another denote cyclopropyl, cyclopentyl or cyclohexyl, or denote phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl, where the cycles are substituted, optionally up to 3 times, in the case of the nitrogen-containing rings also via the N function in an identical or different manner by fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl each having up to 4 carbon atoms, triazolyl, tetrazolyl, benzothiazolyl, trifluoromethyl-substituted phenyl or phenyl and/or are substituted by a group of the formula —OR$^{10}$, —SR$^{11}$ or —SO$_2$R$^{12}$, in which R$^{10}$, R$^{11}$ and R$^{12}$ are identical or different and denote phenyl, which for its part is substituted up to 2 times in an identical or different manner by phenyl, fluorine, chlorine or by straight-chain or branched alkyl having up to 3 carbon atoms, or R$^5$ and/or R$^6$ denotes a radical of the formula R$^7$ denotes hydrogen or fluorine and R$^8$ denotes hydrogen, fluorine, chlorine, bromine, azido, trifluoromethyl, hydroxyl, trifluoromethoxy, or straight-chain or branched alkoxy or alkyl each having up to 4 carbon atoms or a radical of the formula —NR$^{15}$R$^{16}$, in which R$^{15}$ and R$^{16}$ are identical or different and denote hydrogen or straight-chain or branched alkyl having up to 3 carbon atoms, or R$^7$ and R$^8$ together form a radical of the formula =O or =NR$^{17}$, in which R$^{17}$ denotes hydrogen or straight-chain or branched alkyl, alkoxy or acyl each having up to 4 carbon atoms, L denotes a straight-chain or branched alkylene or alkenylene chain each having up to 5 carbon atoms, each of which is optionally substituted up to 2 times by hydroxyl, T and X are identical or different and denote a straight-chain or branched alkylene chain having up to 3 carbon atoms, or T or X denotes a bond, V represents an oxygen or sulphur atom or a group of the formula —NR$^{18}$, in which R$^{18}$ denotes hydrogen or straight-chain or branched alkyl having up to 3 carbon atoms, E represents cyclopropyl, cyclopentyl or cyclohexyl or phenyl, which is optionally substituted by fluorine or trifluoromethyl, or represents straight-chain or branched alkyl having up to 4 carbon atoms, which is optionally substituted by hydroxyl, R$^1$ and R$^2$ together form a straight-chain or branched alkylene chain having up to 5 carbon atoms, which must be substituted by a carbonyl group and/or a radical of the formula in which a and b are identical or different and denote a number 1, 2 or 3, R$^{19}$ denotes hydrogen, cyclopropyl, cyclopentyl, cyclohexyl, straight-chain or branched silylalkyl having up to 6 carbon atoms or straight-chain or branched alkyl having up to 4 carbon atoms, which is optionally substituted by hydroxyl, straight-chain or branched alkoxy having up to 3 carbon atoms or by phenyl, which for its part can be substituted by fluorine, chlorine, bromine, nitro, trifluoromethyl, trifluoromethoxy or by phenyl- or tetrazole-substituted phenyl, and alkyl is optionally substituted by a group of the formula —OR$^{22}$, in which R$^{22}$ denotes straight-chain or branched acyl having up to 3 carbon atoms or benzyl, or R$^{19}$ denotes straight-chain or branched acyl having up to 15 carbon atoms or benzoyl, which is optionally substituted by fluorine, chlorine, bromine, trifluoromethyl, nitro or trifluoromethoxy, or denotes straight-chain or branched fluoroacyl having up to 4 carbon atoms, $R^{20}$ and $R^{21}$ are identical or different, and denote hydrogen, phenyl or straight-chain or branched alkyl having up to 3 carbon atoms or $R^{20}$ and $R^{21}$ together form a cyclopropyl, cyclopentyl or cyclohexyl ring, and the carbocycles formed are optionally substituted up to 4 times in an identical or different manner, optionally also geminally, by fluorine, hydroxyl, trifluoromethyl, carboxyl, azido, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio each having up to 4 carbon atoms or straight-chain or branched alkyl having up to 4 carbon atoms, which for its part is substituted up to 2 times in an identical or different manner by hydroxyl, benzyloxy, trifluoromethyl, benzoyl, methoxy, oxyacetyl and/or phenyl, which for its part can be substituted by fluorine, chlorine, bromine, trifluoromethyl or trifluoromethoxy, and/or the carbocycles formed, are optionally substituted, also geminally, up to 4 times in an identical or different manner by phenyl, benzoyl, thiophenyl or sulphonylbenzoyl, which for their part are optionally substituted by fluorine, trifluoromethyl, trifluoromethoxy or nitro, and/or are optionally substituted by a radical of the formula

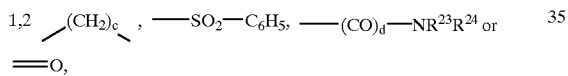

in which c denotes a number 1, 2, 3 or 4, d denotes a number 0 or 1, $R^{23}$ and $R^{24}$ are identical or different and denote hydrogen, cyclopropyl, cyclopentyl, benzyl, straight-chain or branched alkyl having up to 4 carbon atoms or phenyl which is optionally substituted by fluorine, chlorine or bromine, and/or the carbocycles formed are optionally substituted by a spiro-linked radical of the formula

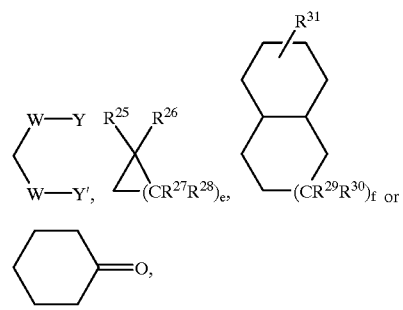

in which

W denotes either an oxygen or a sulphur atom,

Y and Y' together form a 2- to 6-membered straight-chain or branched alkyl chain, e denotes a number 1, 2, 3, 4 or 5, f denotes a number 1 or 2, $R^{25}$, $R^{26}$, $R^{27}$, $R^{28}$, $R^{29}$, $R^{30}$ and $R^{31}$ are identical or different and denote hydrogen, trifluoromethyl, phenyl, fluorine, chlorine, bromine or straight-chain or branched alkyl or alkoxy each having up to 4 carbon atoms, or $R^{25}$ and $R^{26}$ or $R^{27}$ and $R^{28}$ each together form a straight-chain or branched alkylene chain having up to 4 carbon atoms, or $R^{25}$ and $R^{26}$ or $R^{27}$ and $R^{28}$ each together form a radical of the formula

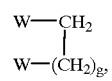

in which

W has the meaning indicated above, g denotes a number 1, 2, 3, 4, 5, 6 or 7, and their salts and N-oxides, with the exception of 5(6H)-quinolone, 3-benzoyl-7,8-dihydro-2, 7, 7-trimethyl-4-phenyl.

4. Cycloalkano-pyridine according to claim 1, which is 2'-(1-methylethyl)-4'-(4-fluorophenyl)-3'[fluoro-(4-trifluoromethyl-phenyl)-methyl]-5',8'-dihydro-6'H-spiro[cyclobutane-1,7'-quinolin]-5'ol of the formula:

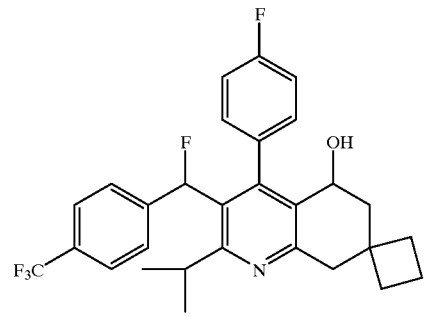

or a salt or N-oxide thereof.

5. Cycloalkano-pyridine according to claim 4, which is (5'S)-2'-(1-methylethyl)-4'-(4-fluorophenyl)-3'[(S)-fluoro-(4-trifluoromethyl-phenyl)-methyl]-5',8'-dihydro-6'H-spiro[cyclobutane-1,7'-quinolin]-5'ol of the formula:

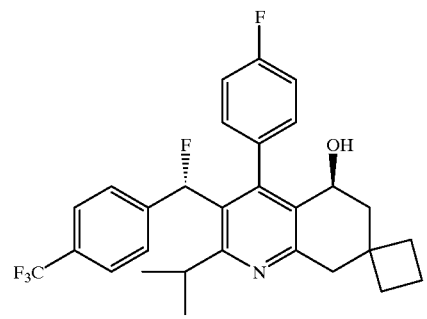

or a salt or N-oxide thereof.

6. Process for the preparation of cycloalkano-pyridines according to claim 1, characterized in that

[A] if D≠aryl, in compounds of the general formula (II)

(II)

[structure: pyridine with OHC, A, R¹, E, N, R²]

in which
A, E, R¹ and R² have the meaning indicated above,
the substituent D is synthesized in inert solvents using organometallic reagents in the sense of a Grignard, Wittig or organolithium reaction,
or if D represents the radical of the formula $R^9$—T—V—X, in which V denotes an oxygen atom,
[B] either compounds of the general formula (III)

(III)

[structure: pyridine with HO—X, A, R¹, E, N, R²]

in which
A, E, X, R¹ and R² have the meaning indicated above, are reacted with compounds of the general formula (IV)

$R^9$—T—Z in which
$R^9$ and T have the meaning indicated above
and
Z represents halogen, preferably chlorine or bromine, in inert solvents, if appropriate in the presence of a base and/or auxiliary,
or
[C] compounds of the general formula (III) are first converted by reaction with compounds of the general formula (V)

(V)

$R^{35}$—S(=O)(=O)—Cl, in which
$R^{35}$ represents straight-chain alkyl having up to 4 carbon atoms,
into the compounds of the general formula (VI)

(VI)

[structure: $R^{35}$—O₂SO—X, A, R¹, E, N, R²]

in which
A, E, X, R¹, R² and $R^{35}$ have the meaning indicated above, and then reacted with compounds of the general formula (VII)

$R^9$—T—V—H          (VII), in which
$R^9$, T and V have the meaning indicated above,
and, if appropriate, protective groups are removed,
or
[D] in the case of the compounds of the general formula (Ia)

(Ia)

[structure: tetrahydroquinoline with F, A, OH, $R^6$, E, N, $R^{36}$, $R^{37}$]

in which
A and $R^6$ have the meaning indicated above,
$R^{36}$ and $R^{37}$ are identical or different and represent trifluoromethyl, halogen, nitro, azido, cyano, cycloalkyl or cycloalkyloxy each having 3 to 7 carbon atoms, or represent straight-chain or branched alkoxycarbonyl, alkoxy or alkylthio each having up to 6 carbon atoms or straight-chain or branched alkyl having up to 6 carbon atoms, or represent phenyl, benzoyl, thiophenyl or sulphonylbenzyl, which for their part are optionally substituted by halogen, trifluoromethyl, trifluoromethoxy or nitro, or
$R^{36}$ and $R^{37}$ represent one of the abovementioned spiro-linked radicals of the formula

[structures with W, Y, Y', $R^{25}$, $R^{26}$, $R^{27}$, $R^{28}$, e, $R^{29}$, $R^{30}$, $R^{31}$, cyclohexanone, $R^{32}$, $R^{33}$]

in which
W, Y, Y', $R^{25}$, $R^{26}$, $R^{27}$, $R^{28}$, e, $R^{29}$, $R^{30}$, $R^{31}$, $R^{32}$ and $R^{33}$ have the meaning indicated above
compounds of the general formula (VIII)

(VIII)

[structure: tetrahydroquinolinone with O, A, O, $R^6$, E, N—H, $R^{36}$, $R^{37}$]

in which
$R^6$, $R^{36}$, $R^{37}$, A and E have the meaning indicated above, are first oxidized to the compounds of the general formula (IX)

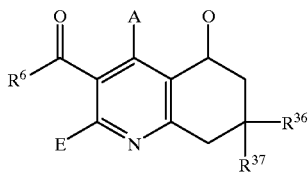
(IX)

in which
$R^6$, $R^{36}$, $R^{37}$, A and E have the meaning indicated above,
these are reacted in a next step by means of an asymmetric reduction to give the compounds of the general formula (X)

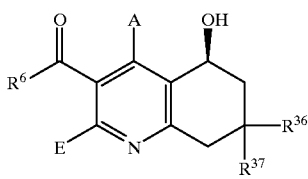
(X)

in which
$R^6$, $R^{36}$, $R^{37}$, A and E have the meaning indicated above,
these are then converted by the introduction of a hydroxyl protective group into the compounds of the general formula (XI)

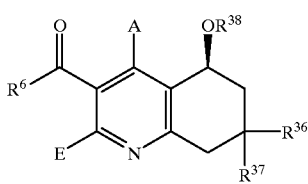
(XI)

in which
$R^6$, $R^{36}$, $R^{37}$, A and E have the meaning indicated above and
$R^{38}$ represents a hydroxyl protective group, preferably a radical of the formula —$SiR^{39}R^{40}R^{41}$,
in which
$R^{39}$, $R^{40}$ and $R^{41}$ are identical or different and denote $C_1$–$C_4$-alkyl, the compounds of the general formula (XII)

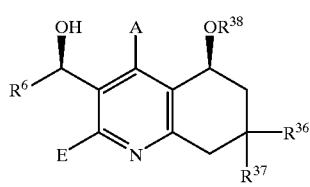
(XII)

in which
$R^6$, $R^{36}$, $R^{37}$, $R^{38}$, A and E have the meaning indicated above, are prepared from these in a subsequent step by diastereoselective reduction, and then by introduction of the fluorine substituent using fluorinating reagents $SF_4$ derivatives the compounds of the general formula (XIII)

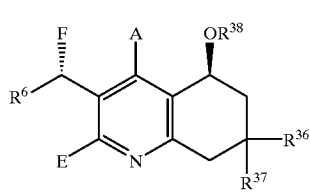
(XIII)

in which
$R^6$, $R^{36}$, $R^{37}$, $R^{38}$, A and E have the meaning indicated above,
are prepared, and then the hydroxyl protective group is removed according to customary methods, and if appropriate the substituents mentioned under D, E and/or $R^1$ and $R^2$ are varied or introduced according to customary methods.

7. A pharmaceutical composition comprising at least one cycloalkano pyridine according to claim 1 and a pharmacologically tolerable formulation auxiliary.

8. A method of treating arteriosclerosis and/or dyslipidaemia comprising administering to a patient in need thereof an effective amount thereof of at least one cycloalkanopyridine according to claim 1.

* * * * *

UNITED STATES PATENT AND TRADEMARK OFFICE
CERTIFICATE OF CORRECTION

PATENT NO. : 6,207,671 B1
DATED : March 27, 2001
INVENTOR(S) : Schmidt et al.

It is certified that error appears in the above-identified patent and that said Letters Patent is hereby corrected as shown below:

<u>Title page,</u>
ABSTRACT, line 8, delete "hypertipoproteinaemia" and substitute
-- Hyperlipoproteinaemia --

Signed and Sealed this

Twelfth Day of March, 2002

Attest:

JAMES E. ROGAN
*Attesting Officer*    *Director of the United States Patent and Trademark Office*